(12) United States Patent
Rennie et al.

(10) Patent No.: US 11,752,169 B2
(45) Date of Patent: Sep. 12, 2023

(54) TREATMENT OF PAIN WITH POLYSULFATED POLYSACCHARIDES

(71) Applicant: PARADIGM BIOPHARMACEUTICALS LTD., Melbourne (AU)

(72) Inventors: Paul Rennie, West Beach (AU); Ravi Krishnan, Royston Park (AU)

(73) Assignee: PARADIGM BIOPHARMACEUTICALS LTD., Melbourne (AU)

( * ) Notice: Subject to any disclaimer, the term of this patent is extended or adjusted under 35 U.S.C. 154(b) by 0 days.

(21) Appl. No.: 17/284,071

(22) PCT Filed: Oct. 10, 2019

(86) PCT No.: PCT/AU2019/051094
§ 371 (c)(1),
(2) Date: Apr. 9, 2021

(87) PCT Pub. No.: WO2020/073089
PCT Pub. Date: Apr. 16, 2020

(65) Prior Publication Data
US 2021/0330695 A1 Oct. 28, 2021

(30) Foreign Application Priority Data

Oct. 10, 2018 (AU) ................................ 2018903820
Feb. 4, 2019 (AU) ................................ 2019900326
Sep. 24, 2019 (AU) ................................ 2019903556

(51) Int. Cl.
*A61K 31/737* (2006.01)
*A61P 19/02* (2006.01)
*A61P 25/04* (2006.01)
*A61K 31/7032* (2006.01)
*A61K 31/727* (2006.01)

(52) U.S. Cl.
CPC ........ *A61K 31/737* (2013.01); *A61K 31/7032* (2013.01); *A61K 31/727* (2013.01); *A61P 19/02* (2018.01); *A61P 25/04* (2018.01)

(58) Field of Classification Search
CPC ... A61K 31/737; A61P 19/00–10; A61P 25/04
See application file for complete search history.

(56) References Cited

U.S. PATENT DOCUMENTS

| 8,293,722 | B2 * | 10/2012 | Cullis-Hill | ........... A61K 31/737 536/118 |
| 9,101,650 | B2 | 8/2015 | Ghosh | |
| 2015/0297633 | A1 * | 10/2015 | Ghosh | ..................... A61P 19/08 514/59 |

OTHER PUBLICATIONS

Starr, A. et al "Bone marrow edema . . . " Acta Radiologica, vol. 7, pp. 771-786. (Year: 2008).*

Ghosh, P. et al., Effects of pentosan polysulfate in osteoarthritis of the knee: A randomized, double-blind, placebo-controlled pilot study. Curr Ther Res. Nov. 2005;66(6):552-71. doi: 10.1016/j. curtheres.2005.12.012., Abstract; p. 555, "Study Drugs"; Figures 1 and 2a; p. 553, "Conclusions".
Hwang, P. et al. Efficacy ofpentosan polysulfate in the treatment of interstitial cystitis: a meta-analysis. Urology. Jul. 1997; 50(1):39-43. p. 41, col. 1, paragraph 2; Table 2; Conclusions; Whole document.
Jiang, YH et al., Decrease of urinary nerve growth factor but not brain-derived neurotrophic factor in patients with interstitial cystitis/ bladder pain syndrome treated with hyaluronic acid., PLOS One. Mar. 10, 2014;9(3):e91609. doi: 10.1371/journal.pone.0091609. eCollection 2014. Abstract; Table 1 and 2; Figure 1.
Kumar, V. et al., BA. NGF—the TrkA to successful pain treatment. J Pain Res.2012;5:279-87. doi: 10.2147/JPR.S33408. Epub Aug. 17, 2012. Whole document.
Liu, HT et al., Urinary nerve growth factor level is increased in patients with interstitial cystitis/bladder pain syndrome and decreased in responders to treatment. BJU Int. Nov. 2009;I 04(10):1476-81. doi:10.111 1/j.1464-410X.2009.08675.x., pub Jun. 12, 2009. p. 1477. middle column, paragraph 3; Table I; p. 1479, third column, paragraphs 1 and 2.
McCaffrey, G. et al., NGF blockade at early times during bone cancer development attenuates bone destruction and increases limb use., Cancer Res. Dec. 1, 2014;74(23):7014-23. doi:10.1158/0008-5472.CAN-14-1220. Epub Oct. 6, 2014. Abstract; Figures 2, 4, and 6; p. 2, paragraph 2.
McMahon, SB , NGF as a mediator of inflammatory pain. Philos Trans R Soc Lond B Biol Sci. Mar. 29, 1996;351(1338):431-40. Review Whole document.
Samson, MJ et al., Improved clinical outcome measures of knee pain and function with concurrent resolution of subchondral Bone Marrow Edema Lesion and joint effusion in an osteoarthritic patient following Pentosan Polysulphate Sodium treatment: a case report., BMC Musculoskelet Disord. Sep. 12, 20172; 18(1 ):396. doi: 1 O. 11 86/sl2891-01 7-1754-3., Abstract; p. 2, col. 2, paragraph 3; p. 3, col. 1, paragraph I; Figure 1.
Extended European Search Report for European Patent Application No. 19871048.5, dated May 27, 2022, 11 pages.
Matthew J. Sampson et al: "Improved clinical outcome measures of knee pain and function with concurrent resolution of subchondral Bone Marrow Edema Lesion and joint effusion in an osteoarthritic patient following Pentosan Polysulphate Sodium treatment: a case report", BMC Musculoskeletal Disorders, vol. 18, No. 1, Sep. 12, 2017 (Sep. 12, 2017), pp. 1-5.
Kumar, V. et al., BA. NGF—the TrkA to successful pain treatment. Journal of Pain Research 2012:5, Aug. 1, 2012, pp. 279-287.

* cited by examiner

*Primary Examiner* — Leigh C Maier
(74) *Attorney, Agent, or Firm* — Dorsey & Whitney LLP

(57) ABSTRACT

The present disclosure relates to the medical use of polysulfated polysaccharides and compositions thereof for the treatment of pain or pain conditions. In particular, the disclosure relates to use of polysulfated polysaccharides and compositions thereof for the treatment of pain or pain conditions mediated by mature Nerve Growth Factor (NGF) or its precursor pro-Nerve Growth Factor (pro-NGF).

7 Claims, 29 Drawing Sheets

Specification includes a Sequence Listing.

A.

B.

C.

A.

B.

C.

A.

B.

C.

A.

B.

C.

A.

B.

C.

A.

B.

C.

D.

A.

B.

C.

D.

A.

B.

C.

D.

A.

B.

C.

D.

A.

B.

C.

D.

A.

B.

A.

B.

A.

B.

A.

B.

C.

D.

A.

B.

TREATMENT OF PAIN WITH POLYSULFATED POLYSACCHARIDES

CROSS-REFERENCE TO RELATED APPLICATIONS

This application is a national stage application under 35 U.S.C. § 371 of International Application No. PCT/AU2019/051094, filed Oct. 10, 2019, entitled "TREATMENT OF PAIN WITH POLYSULFATED POLYSACCHARIDES," which claims the benefit of Australian Patent Application Serial Number 2018903820, filed Oct. 10, 2018; Australian Patent Application Serial Number 2019900326, filed Feb. 4, 2019; and Australian Patent Application Serial Number 2019903556, the entire disclosures of which are hereby incorporated herein by reference.

TECHNICAL FIELD

This disclosure relates to the medical use of polysulfated polysaccharides and compositions thereof for the treatment of pain or pain conditions. In particular, the disclosure relates to use of polysulfated polysaccharides and compositions thereof for the treatment of pain or pain conditions mediated by mature Nerve Growth Factor (NGF) or its precursor pro-Nerve Growth Factor (pro-NGF).

SEQUENCE LISTING

A sequence listing submitted in computer readable format is hereby incorporated by reference it its entirety. The computer readable file (ASCII text file) is named "185383US Sequence Listing_ST25.txt" created on Jun. 19, 2023, and is 8,478 bytes in size.

BACKGROUND

Safe and effective pain medications continue to represent an unmet medical need. Pain is a symptom of disease and a disease unto itself. As examples of skeletal disease, osteoarthritis and osteoporosis result in significant physical disability, pain and reduced quality of life. Primary and secondary (metastatic) bone cancer cause excruciating bone pain. Chronic pain is reported to affect approximately 100 million Americans at an estimated annual cost of US$560-US$635 billion. The public health and economic burden of pain is enormous [1].

The mainstay for the treatment of pain typically involves administration of opioids and nonsteroidal anti-inflammatory drugs (NSAIDs). Despite dominating the clinal landscape these agents have limited effectiveness and considerable side-effect profiles and in the case of opioids, problems with addiction or morbidity [2]. NSAIDs have been found to exacerbate disease. For example, with regard to diseases such as bone cancer, osteoporosis and osteoarthritis, NSAIDS have negative effects on bone healing and the metabolism of cartilage ([3]-[6]). The risk of fracture, both traumatic and spontaneous, is increased in those subjects who require prolonged or continuous therapy.

Within this context, the neurotrophin Nerve Growth Factor (NGF) and related molecular targets such as the NGF precursor pro-NGF provide an alternative to NSAIDs and opioids in the treatment of malignant and non-malignant pain [7] and nociceptive and neuropathic pain conditions including arthritis, osteoarthritis, osteoporosis, interstitial cystitis, prostatitis, pancreatitis, chronic headache pain, cancer pain, non-cancer pain, back pain and diabetic neuropathy [1]. NGF and other related molecular targets, such as pro-NGF, also have potential in the treatment of other pain conditions, for example, fibromyalgia [1A] and inflammatory pain, such as that associated with endometriosis [1B]. Further, NGF has been found to play a role in the pathophysiology of central neuropathic pain. In this regard, high levels of NGF have been observed in the cerebrospinal fluid of patients suffering from multiple sclerosis [1C].

Agents that target NGF have been developed for treating pain conditions. Among these, anti-NGF antibodies have exhibited the most promise and NGF sequestering antibodies have been developed: TANEZUMAB® (Pfizer and Eli Lilly), FASINUMAB® (TEVA and Regeneron) and FULRANUMAB® (Janssen and Amgen). However, there have been some reports that anti-NGF antibodies may be associated with joint destruction leading to joint replacement and neural toxicity [1]. Further, the long term efficacy and safety profile of anti-NGF antibodies is still to be established. In light of the above, there is a need to expand the repertoire of pharmaceutical agents available to providing new and improved pain medications.

SUMMARY

Heparin and structurally related polysulfated polysaccharides such as pentosan polysulfate, chitosan polysulfate, the fucans etc have been used for a number of years as anticoagulants [8-13] and are safe. Pentosan polysulfate (PPS) has been used post-surgically and prophylactically as a thrombolytic agent [13], and PPS is the active agent in the drug ELMIRON® which is currently prescribed for interstitial cystitis. The potential use of PPS in treatment of inflammatory conditions such as asthma, allergic rhinitis, and/or chronic obstructive pulmonary disease (COPD) has also been described [14], as has the use of PPS in bone related pathologies, such as osteoporosis [15] and bone marrow edema [16].

The present disclosure is based, in part, on the surprising finding that PPS can act to inhibit or reduce NGF activity. Thus, PPS has been found to act through a mechanism of action that is distinct from the current anti-NGF antibodies, Tanezumab, Fasinumab and Fulranumab, which all act as NGF-sequestering agents. In addition, it has been surprisingly found that PPS can act to inhibit or reduce pro-NGF activity. Experimental data demonstrates that, for example, PPS can inhibit or reduce the expression of NGF at both the mRNA and protein level and that PPS can inhibit or reduce the expression of pro-NGF, which consequently affects the level of NGF and its activity. Further, the experimental data demonstrates that PPS may exert its pharmacological effects by targeting NGF producing osteocytes as mediators of pain and pain related conditions. Whilst the experimental data uses osteocytes as an example of cells that may mediate pain and pain related conditions, the present disclosure contemplates the use of other targets cells that secrete NGF or pro-NGF as mediators of pain and pain related conditions. Examples of such target cells are immune cells and cancer cells including primary cancer cells and secondary cancer cells.

According to one aspect, there is provided a method of inhibiting or reducing Nerve Growth Factor (NGF) activity in a mammal, the method comprising the step of administering a polysulfated polysaccharide or an acceptable salt thereof, to the mammal.

According to another aspect, there is provided a method of inhibiting or reducing pro-Nerve Growth Factor (pro-NGF) activity in a mammal, the method comprising the step of administering a polysulfated polysaccharide or an acceptable salt thereof, to the mammal.

According to another aspect, there is provided a method of treating pain mediated by Nerve Growth Factor (NGF), the method comprising the step of administering a polysulfated polysaccharide or an acceptable salt thereof, to a mammal in need of such treatment.

According to another aspect, there is provided a method of treating pain mediated by pro-Nerve Growth Factor (NGF), the method comprising the step of administering a polysulfated polysaccharide or an acceptable salt thereof, to a mammal in need of such treatment.

According to another aspect, there is provided a composition comprising a polysulfated polysaccharide or an acceptable salt thereof, and an acceptable excipient for inhibiting or reducing Nerve Growth Factor (NGF) activity in a mammal.

According to another aspect, there is provided a composition comprising a polysulfated polysaccharide or an acceptable salt thereof, and an acceptable excipient for inhibiting or reducing pro-Nerve Growth Factor (pro-NGF) activity in a mammal.

According to another aspect, there is provided a composition comprising a polysulfated polysaccharide or an acceptable salt thereof, and an acceptable excipient for use in inhibiting or reducing Nerve Growth Factor (NGF) activity in a mammal.

According to another aspect, there is provided a composition comprising a polysulfated polysaccharide or an acceptable salt thereof, and an acceptable excipient for use in inhibiting or reducing pro-Nerve Growth Factor (pro-NGF) activity in a mammal.

According to another aspect, there is provided a composition comprising a polysulfated polysaccharide or an acceptable salt thereof, and an acceptable excipient for treating pain mediated by Nerve Growth Factor (NGF) in a mammal.

According to another aspect, there is provided a composition comprising a polysulfated polysaccharide or an acceptable salt thereof, and an acceptable excipient for treating pain mediated by pro-Nerve Growth Factor (pro-NGF) in a mammal.

According to another aspect, there is provided a composition comprising a polysulfated polysaccharide or an acceptable salt thereof, and an acceptable excipient for use in treating pain mediated by Nerve Growth Factor (NGF) in a mammal.

According to another aspect, there is provided a composition comprising a polysulfated polysaccharide or an acceptable salt thereof, and an acceptable excipient for use in treating pain mediated by pro-Nerve Growth Factor (pro-NGF) in a mammal.

According to another aspect, there is provided use of a polysulfated polysaccharide or an acceptable salt thereof, in inhibiting or reducing Nerve Growth Factor (NGF) activity in a mammal.

According to another aspect, there is provided use of a polysulfated polysaccharide or an acceptable salt thereof, in inhibiting or reducing pro-Nerve Growth Factor (NGF) activity in a mammal.

According to another aspect, there is provided use of a polysulfated polysaccharide or an acceptable salt thereof, in the manufacture of a medicament for inhibiting or reducing Nerve Growth Factor (NGF) activity in a mammal.

According to another aspect, there is provided use of a polysulfated polysaccharide or an acceptable salt thereof, in the manufacture of a medicament for inhibiting or reducing pro-Nerve Growth Factor (pro-NGF) activity in a mammal.

According to another aspect, there is provided use of a polysulfated polysaccharide or an acceptable salt thereof, in treating pain mediated by Nerve Growth Factor (NGF) in a mammal.

According to another aspect, there is provided use of a polysulfated polysaccharide or an acceptable salt thereof, in treating pain mediated by pro-Nerve Growth Factor (pro-NGF) in a mammal.

According to another aspect, there is provided use of a polysulfated polysaccharide or an acceptable salt thereof, in the manufacture of a medicament for treating pain mediated by Nerve Growth Factor (NGF) in a mammal.

According to another aspect, there is provided use of a polysulfated polysaccharide or an acceptable salt thereof, in the manufacture of a medicament for treating pain mediated by pro-Nerve Growth Factor (pro-NGF) in a mammal.

Definitions

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular. Thus, as used in this specification and the appended claims, the singular forms "a", "an" and "the" include plural referents unless the context clearly indicates otherwise. For example, reference to "a cell" includes populations of a plurality of cells.

With regards to the definitions provided herein, unless stated otherwise, or implicit from context, the defined terms and phrases include the provided meanings. Unless explicitly stated otherwise, or apparent from context, the terms and phrases below do not exclude the meaning that the term or phrase has acquired by a person skilled in the relevant art. The definitions are provided to aid in describing particular embodiments, and are not intended to limit the claimed invention, because the scope of the invention is limited only by the claims.

Throughout the present specification, various aspects and components of the invention can be presented in a range format. The range format is included for convenience and should not be interpreted as an inflexible limitation on the scope of the invention. Accordingly, the description of a range should be considered to have specifically disclosed all the possible sub-ranges as well as individual numerical values within that range, unless specifically indicated. For example, description of a range such as from 1 to 5 should be considered to have specifically disclosed sub-ranges such as from 1 to 2, from 1 to 3, from 1 to 4, from 2 to 3, from 2 to 4, from 2 to 5, from 3 to 4 etc., as well as individual and partial numbers within the recited range, for example, 1, 2, 3, 4, and 5. This applies regardless of the breadth of the disclosed range. Where specific values are required, these will be indicated in the specification.

The term "acceptable excipient" includes excipients or agents such as solvents, diluents, dispersion media, coatings, antibacterial and antifungal agents, isotonic and absorption delaying agents and the like that are physiologically compatible and are not deleterious to a compound as described herein or use thereof. The use of such carriers and agents to prepare compositions of pharmaceutically active substances is well known in the art (see, for example Remington: The Science and Practice of Pharmacy, 21st Edition; Lippincott Williams & Wilkins: Philadelphia, PA, 2005).

The term "acceptable salts" include, but are not limited to, inorganic acid salts such as hydrochloride, hydrobromide, sulfate, phosphate and the like; organic acid salts such as formate, acetate, trifluoroacetate, maleate, tartrate and the like; sulfonates such as methanesulfonate, benzenesulfonate, p-toluenesulfonate and the like; amino acid salts such as arginate, asparaginate, glutamate and the like; metal salts such as sodium salt, potassium salt, cesium salt and the like; alkaline earth metals such as calcium salt, magnesium salt and the like; and organic amine salts such as triethylamine salt, pyridine salt, picoline salt, ethanolamine salt, triethanolamine salt, discyclohexylamine salt, N,N'-dibenzylethylenediamine salt and the like.

Base salts include, but are not limited to, those formed with pharmaceutically acceptable cations, such as sodium, potassium, lithium, calcium, magnesium, zinc, ammonium, alkylammonium such as salts formed from triethylamine, alkoxyammonium such as those formed with ethanolamine and salts formed from ethylenediamine, choline or amino acids such as arginine, lysine or histidine. General information on types of acceptable salts and their formation is known to those skilled in the art and is as described in general texts such as "Handbook of Pharmaceutical salts" P. H. Stahl, C. G. Wermuth, $1^{st}$ edition, 2002, Wiley-VCH.

The terms "administration of" and or "administering a" compound should be understood to mean providing a compound of the invention to the individual in need of treatment.

The term "composition" as used herein is intended to encompass a product comprising the specified ingredients in the specified amounts, as well as any product which results, directly or indirectly, from combination of the specified ingredients in the specified amounts.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

This disclosure is directed to treatments of mammal subjects. The treatment of a "mammal" subject may also be referred to the treatment of a "patient" or an "individual". A "mammal" subject has presented a clinical manifestation of a particular symptom or symptoms suggesting the need for treatment, is treated for a condition, or who has been diagnosed with a condition to be treated.

As used herein, "malignant pain" refers to pain related to cancer: "non-malignant pain" refers to pain that is not related to cancer.

Thus, the invention is to be understood to be applicable to humans and other non-human mammals unless specifically indicated otherwise. The human can be male or female. Other non-human mammals may be a primate, livestock and farm animals (e.g. sheep, horses, cattle, pigs), domestic pets, such as cats and dogs, performance animal (e.g. racehorses, camels, greyhounds), laboratory test animal (e.g. mice, rabbits, rats, guinea pigs) as well as those mammals that usually exist in the wild but may be susceptible to treatment by virtue of such mammals being situated in zoos, wildlife parks and the like.

As used herein, the terms "treating", "treat" or "treatment" and variations thereof, refer to clinical intervention designed to alter the natural course of the subject during the course of clinical pathology, as compared to not administering a polysulfated polysaccharide or acceptable salt thereof or a composition composition comprising a polysulfated polysaccharide or acceptable salt thereof. Desirable effects of treatment include decreasing the rate of disease progression, ameliorating or palliating the disease state, and remission or improved prognosis. A subject is successfully "treated", for example, if one or more of the above treatment outcomes is achieved. As used herein, the terms "treating", "treat" or "treatment" and variations thereof encompass "preventing", "prevent" or "prevention" which would be understood to refer to clinical intervention designed to avert the development of a course of clinical pathology.

An "effective amount" encompasses a "therapeutically effective" amount which refers to at least the minimum concentration or amount required to effect a measurable improvement of a particular disease (e.g., bone marrow edema). An effective amount herein may vary according to factors such as the disease state, age, sex, and weight of the patient, and the ability of the PPS to elicit a desired response in the individual. An effective amount is also one in which any toxic or detrimental effects of the PPS are outweighed by the therapeutically beneficial effects. An "effective amount" also encompasses a "prophylactically effective" amount which refers to the amount of drug or the rate of drug administration needed to produce the desired preventive result.

DESCRIPTION OF EMBODIMENTS

The present disclosure relates to a method of inhibiting or reducing Nerve Growth Factor (NGF) activity in a mammal, the method comprising the step of administering a polysulfated polysaccharide or an acceptable salt thereof, to the mammal.

The present disclosure also relates to a method of inhibiting or reducing pro-Nerve Growth Factor (pro-NGF) activity in a mammal, the method comprising the step of administering a polysulfated polysaccharide or an acceptable salt thereof, to the mammal.

In the above methods, the inhibiting or reducing of NGF activity or pro-NGF activity preferably treats pain in the mammal.

Experimental data shows that PPS can inhibit or reduce the expression of NGF at both the mRNA and protein level and that PPS can inhibit or reduce the expression of pro-NGF, which consequently affects the level of NGF and its activity. Further, the experimental data demonstrates that PPS may exert its pharmacological effects by targeting NGF producing osteocytes as mediators of pain and pain related conditions. Whilst the experimental data uses osteocytes as an example of cells that may mediate pain and pain related conditions, the present disclosure contemplates the use of other targets cells that secrete NGF or pro-NGF as mediators of pain and pain related conditions. Examples of such target cells are immune cells and cancer cells including primary cancer cells and secondary cancer cells.

Thus, in examples of the methods, composition or uses described herein, the inhibiting or reducing Nerve Growth Factor (NGF) activity in a mammal is by inhibiting or reducing the expression of NGF. In one example, the inhibiting or reducing of expression of NGF is by inhibiting or reducing the transcription of mRNA. In one example, the inhibiting or reducing of expression of NGF is by inhibiting or reducing the translation of mRNA to protein.

Thus, in examples of the methods, composition or uses described herein, the inhibiting or reducing pro-Nerve Growth Factor (pro-NGF) activity in a mammal is by inhibiting or reducing the expression of pro-NGF. In one example, the inhibiting or reducing of expression of pro-NGF is by inhibiting or reducing the transcription of mRNA.

In one example, the inhibiting or reducing of expression of pro-NGF is by inhibiting or reducing the translation of mRNA to protein.

The present disclosure further contemplates the inhibition and reduction of NGF activity as a consequence of the inhibition and reduction of pro-NGF activity.

The present disclosure also relates to a method of treating pain mediated by Nerve Growth Factor (NGF), the method comprising the step of administering a polysulfated polysaccharide or an acceptable salt thereof, to a mammal in need of such treatment.

The present disclosure also relates to a method of treating pain mediated by pro-Nerve Growth Factor (pro-NGF), the method comprising the step of administering a polysulfated polysaccharide or an acceptable salt thereof, to a mammal in need of such treatment.

In the above methods, the pain is non-malignant pain or malignant pain.

In the above methods, the pain is preferably musculoskeletal pain. Preferably, the musculoskeletal pain is non-malignant musculoskeletal pain. Preferably, the musculoskeletal pain is malignant musculoskeletal pain. Preferably, the musculoskeletal pain is skeletal pain. Preferably, the skeletal pain is non-malignant skeletal pain. Preferably, the skeletal pain is malignant skeletal pain.

Preferably, the skeletal pain is back pain. Preferably, the back pain is low back pain. Preferably, the skeletal pain is bone and/or joint pain. Preferably, the skeletal pain is joint pain. Preferably, the skeletal pain is bone pain. Preferably, the bone pain is non-malignant bone pain. Preferably, the non-malignant bone pain is pain associated with osteoporosis.

Preferably, the non-malignant bone pain is pain associated with an arthritic condition. Preferably, the arthritic condition is selected from rheumatoid arthritis or osteoarthritis. Preferably, the arthritic condition is rheumatoid arthritis. Preferably, the arthritic condition is osteoarthritis. Preferably, the osteoarthritis is in an articulating joint selected from the group consisting of: an ankle, a hip, knee, shoulder, spine and wrist. Preferably, the osteoarthritis is in the hip. Preferably, the osteoarthritis is in the knee. Preferably, the osteoarthritis is in the spine (spondylosis). Preferably, the bone pain is malignant bone pain. Preferably, the malignant bone pain is pain associated with primary bone cancer. Preferably, the malignant bone pain is pain associated with secondary (metastatic) bone cancer.

Preferably, the pain is selected from the group consisting of: acute pain; cancer pain; chronic pain; general pain; non-cancer pain and persistent pain. Preferably, the pain is a nociceptive pain condition or a neuropathic pain condition. Preferably, the pain is an acute pain condition; chronic pain condition; general pain condition and persistent pain condition. Preferably, the pain condition is a non-malignant pain condition. Preferably, the pain condition is a malignant pain condition.

Preferably, the pain is associated with a condition selected from the group consisting of: arthritis; osteoarthritis; rheumatoid arthritis; prostatitis; interstitial cystitis; osteoporosis; abdominal pain; arthralgia; endometriosis; pancreatitis; chronic headaches; primary cancer; secondary (metastatic) cancer; back pain; bone injury or fracture; diabetic neuropathy; fibromyalgia; migraine; multiple myeloma bone disease; multiple sclerosis; osteoporosis; neuralgia; herpetic neuralgia; postherpetic neuralgia; neoplasm; sciatica; and visceral pain.

Preferably, the pain is associated with a condition selected from the group consisting of: arthritis; osteoarthritis; rheumatoid arthritis; prostatitis and interstitial cystitis.

Preferably, the pain is associated with a condition selected from the group consisting of: abdominal pain; arthralgia; endometriosis; pancreatitis; chronic headaches; primary cancer; secondary (metastatic) cancer; back pain; bone injury or fracture; diabetic neuropathy; fibromyalgia; migraine; multiple myeloma bone disease; multiple sclerosis; osteoporosis; neuralgia; herpetic neuralgia; postherpetic neuralgia; neoplasm; sciatica; and visceral pain.

The present disclosure also relates to a composition comprising a polysulfated polysaccharide or an acceptable salt thereof, and an acceptable excipient for inhibiting or reducing Nerve Growth Factor (NGF) activity in a mammal.

The present disclosure also relates to a composition comprising a polysulfated polysaccharide or an acceptable salt thereof, and an acceptable excipient for inhibiting or reducing pro-Nerve Growth Factor (pro-NGF) activity in a mammal.

The present disclosure also relates to a composition comprising a polysulfated polysaccharide or an acceptable salt thereof, and an acceptable excipient for use in inhibiting or reducing Nerve Growth Factor (NGF) activity in a mammal.

The present disclosure also relates to a composition comprising a polysulfated polysaccharide or an acceptable salt thereof, and an acceptable excipient for use in inhibiting or reducing pro-Nerve Growth Factor (pro-NGF) activity in a mammal.

In the above compositions, the inhibiting or reducing treats pain in the mammal.

The present disclosure also relates a composition comprising a polysulfated polysaccharide or an acceptable salt thereof, and an acceptable excipient for treating pain mediated by Nerve Growth Factor (NGF) in a mammal.

The present disclosure also relates a composition comprising a polysulfated polysaccharide or an acceptable salt thereof, and an acceptable excipient for treating pain mediated by pro-Nerve Growth Factor (pro-NGF) in a mammal.

The present disclosure also relates a composition comprising a polysulfated polysaccharide or an acceptable salt thereof, and an acceptable excipient for use in treating pain mediated by Nerve Growth Factor (NGF) in a mammal.

The present disclosure also relates a composition comprising a polysulfated polysaccharide or an acceptable salt thereof, and an acceptable excipient for use in treating pain mediated by pro-Nerve Growth Factor (pro-NGF) in a mammal.

In the above compositions, the pain is non-malignant pain or malignant pain.

In the above compositions, the pain is preferably musculoskeletal pain. Preferably, the musculoskeletal pain is non-malignant musculoskeletal pain. Preferably, the musculoskeletal pain is malignant musculoskeletal pain. Preferably, the musculoskeletal pain is skeletal pain. Preferably, the skeletal pain is non-malignant skeletal pain. Preferably, the skeletal pain is malignant skeletal pain.

Preferably, the skeletal pain is back pain. Preferably, the back pain is low back pain. Preferably, the skeletal pain is bone and/or joint pain. Preferably, the skeletal pain is joint pain. Preferably, the skeletal pain is bone pain. Preferably, the bone pain is non-malignant bone pain. Preferably, the non-malignant bone pain is pain associated with osteoporosis.

Preferably, the non-malignant bone pain is pain associated with an arthritic condition. Preferably, the arthritic condition is selected from rheumatoid arthritis or osteoarthritis. Preferably, the arthritic condition is rheumatoid arthritis. Preferably, the arthritic condition is osteoarthritis. Preferably, the osteoarthritis is in an articulating joint selected from the group consisting of: an ankle, a hip, knee, shoulder, spine and wrist. Preferably, the osteoarthritis is in the hip. Preferably, the osteoarthritis is in the knee. Preferably, the osteoarthritis is in the spine (spondylosis). Preferably, the bone pain is malignant bone pain. Preferably, the malignant bone pain is pain associated with primary bone cancer. Preferably, the malignant bone pain is pain associated with secondary (metastatic) bone cancer.

Preferably, the pain is selected from the group consisting of: acute pain; cancer pain; chronic pain; general pain; non-cancer pain and persistent pain. Preferably, the pain is a nociceptive pain condition or a neuropathic pain condition. Preferably, the pain is an acute pain condition; chronic pain condition; general pain condition and persistent pain condition. Preferably, the pain condition is a non-malignant pain condition. Preferably, the pain condition is a malignant pain condition.

Preferably, the pain is associated with a condition selected from the group consisting of: arthritis; osteoarthritis; rheumatoid arthritis; prostatitis; interstitial cystitis; osteoporosis; abdominal pain; arthralgia; endometriosis; pancreatitis; chronic headaches; primary cancer; secondary (metastatic) cancer; back pain; bone injury or fracture; diabetic neuropathy; fibromyalgia; migraine; multiple myeloma bone disease; multiple sclerosis; osteoporosis; neuralgia; herpetic neuralgia; postherpetic neuralgia; neoplasm; sciatica; and visceral pain. Preferably, the bone fracture is a femur fracture. The femur fracture is preferably a neck of femur fracture.

Preferably, the pain is associated with a condition selected from the group consisting of: arthritis; osteoarthritis; rheumatoid arthritis; prostatitis and interstitial cystitis.

Preferably, the pain is associated with a condition selected from the group consisting of: abdominal pain; arthralgia; endometriosis; pancreatitis; chronic headaches; primary cancer; secondary (metastatic) cancer; back pain; bone injury or fracture; diabetic neuropathy; fibromyalgia; migraine; multiple myeloma bone disease; multiple sclerosis; osteoporosis; neuralgia; herpetic neuralgia; postherpetic neuralgia; neoplasm; sciatica; and visceral pain. Preferably, the bone fracture is a femur fracture. The femur fracture is preferably a neck of femur fracture.

The present disclosure also relates to use of a polysulfated polysaccharide or an acceptable salt thereof, in inhibiting or reducing Nerve Growth Factor (NGF) activity in a mammal.

The present disclosure also relates to use of a polysulfated polysaccharide or an acceptable salt thereof, in inhibiting or reducing pro-Nerve Growth Factor (pro-NGF) activity in a mammal.

The present disclosure also relates to use of a polysulfated polysaccharide or an acceptable salt thereof, in the manufacture of a medicament for inhibiting or reducing Nerve Growth Factor (NGF) activity in a mammal.

The present disclosure also relates to use of a polysulfated polysaccharide or an acceptable salt thereof, in the manufacture of a medicament for inhibiting or reducing pro-Nerve Growth Factor (pro-NGF) activity in a mammal.

In the uses above, the inhibiting or reducing treats pain in the mammal.

The present disclosure also relates to use of a polysulfated polysaccharide or an acceptable salt thereof, in treating pain mediated by Nerve Growth Factor (NGF) in a mammal.

The present disclosure also relates to use of a polysulfated polysaccharide or an acceptable salt thereof, in treating pain mediated by pro-Nerve Growth Factor (pro-NGF) in a mammal.

The present disclosure also relates to use of a polysulfated polysaccharide or an acceptable salt thereof, in the manufacture of a medicament for treating pain mediated by Nerve Growth Factor (NGF) in a mammal.

The present disclosure also relates to use of a polysulfated polysaccharide or an acceptable salt thereof, in the manufacture of a medicament for treating pain mediated by pro-Nerve Growth Factor (pro-NGF) in a mammal.

In the above uses, the pain is non-malignant pain or malignant pain.

In the above uses, the pain is preferably musculoskeletal pain. Preferably, the musculoskeletal pain is non-malignant musculoskeletal pain. Preferably, the musculoskeletal pain is malignant musculoskeletal pain. Preferably, the musculoskeletal pain is skeletal pain. Preferably, the skeletal pain is non-malignant skeletal pain. Preferably, the skeletal pain is malignant skeletal pain.

Preferably, the skeletal pain is back pain. Preferably, the back pain is low back pain. Preferably, the skeletal pain is bone and/or joint pain. Preferably, the skeletal pain is joint pain. Preferably, the skeletal pain is bone pain. Preferably, the bone pain is non-malignant bone pain. Preferably, the non-malignant bone pain is pain associated with osteoporosis.

Preferably, the non-malignant bone pain is pain associated with an arthritic condition. Preferably, the arthritic condition is selected from rheumatoid arthritis or osteoarthritis. Preferably, the arthritic condition is rheumatoid arthritis. Preferably, the arthritic condition is osteoarthritis. Preferably, the osteoarthritis is in an articulating joint selected from the group consisting of: an ankle, a hip, knee, shoulder, spine and wrist.

Preferably, the osteoarthritis is in the hip. Preferably, the osteoarthritis is in the knee. Preferably, the osteoarthritis is in the spine (spondylosis). Preferably, the bone pain is malignant bone pain. Preferably, the malignant bone pain is pain associated with primary bone cancer. Preferably, the malignant bone pain is pain associated with secondary (metastatic) bone cancer.

Preferably, the pain is selected from the group consisting of: acute pain; cancer pain; chronic pain; general pain; non-cancer pain and persistent pain. Preferably, the pain is a nociceptive pain condition or a neuropathic pain condition. Preferably, the pain is an acute pain condition; chronic pain condition; general pain condition and persistent pain condition. Preferably, the pain condition is a non-malignant pain condition. Preferably, the pain condition is a malignant pain condition.

Preferably, the pain is associated with a condition selected from the group consisting of: arthritis, osteoarthritis, rheumatoid arthritis, interstitial cystitis, abdominal pain; arthralgia; endometriosis, osteoporosis, prostatitis, pancreatitis, chronic headaches, primary cancer, secondary (metastatic) cancer, back pain, bone injury or fracture, diabetic neuropathy, fibromyalgia; migraine; multiple myeloma bone disease, multiple sclerosis; osteoporosis, neuralgia; herpetic neuralgia; postherpetic neuralgia; neoplasm; sciatica; and visceral pain. Preferably, the bone fracture is a femur fracture. The femur fracture is preferably a neck of femur fracture.

Preferably, the pain is associated with a condition selected from the group consisting of: arthritis; osteoarthritis; rheumatoid arthritis; prostatitis; and interstitial cystitis.

Preferably, the pain is associated with a condition selected from the group consisting of: abdominal pain; arthralgia; endometriosis; pancreatitis; chronic headaches; primary cancer; secondary (metastatic) cancer; back pain; bone injury or fracture; diabetic neuropathy; fibromyalgia; migraine; multiple myeloma bone disease; multiple sclerosis; osteoporosis, neuralgia; herpetic neuralgia; postherpetic neuralgia; neoplasm; sciatica; and visceral pain. Preferably, the bone fracture is a femur fracture. The femur fracture is preferably a neck of femur fracture.

The present disclosure also contemplates the methods, compositions and uses as described above, wherein the polysulfated polysaccharide is preferably selected from the group consisting of high molecular weight heparin, low molecular weight heparins, the heparan sulfates, pentosan polysulfate, chondroitin polysulfate, chitosan polysulfate, dermatan polysulfate sulodexide, dextran sulfate, polysulfated inulin, sulfated lactobionic acid amide, sulfated bisaldonic acid amide, sucrose octasulfate, fucoidan-1, fucoidan-2, sulfated beta-cyclodextrin, sulfated gamma-cyclodextrin and small sulfated compounds including, but are not limited to, inositol hexasulfate.

Preferably, the polysulfated polysaccharide is selected from the group consisting of high molecular weight heparin, low molecular weight heparins, pentosan polysulfate (PPS), chondroitin polysulfate and chitosan polysulfate.

The pentosan polysulfate (PPS) is preferably selected from the group consisting of: the sodium salt of pentosan polysulfate (NaPPS), the magnesium salt of pentosan polysulfate (MgPPS), the calcium salt of pentosan polysulfate (CaPPS), and the zinc salt of pentosan polysulfate (ZnPPS).

Preferably, the pentosan polysulfate (PPS) is sodium pentosan polysulfate (NaPPS).

In one preferred embodiment, NaPPS is manufactured to the specifications lodged with the US FDA and European Community EMEA by Bene-PharmaChem GmbH & Co KG, Geretsried, Germany.

It will be recognized by persons skilled in the art, that PPS and PPS compositions suitable for administration by a variety of routes may be formulated by reference to standard textbooks in this field, such as Remington: The Science and Practice of Pharmacy, 21st Edition; Lippincott Williams & Wilkins: Philadelphia, P A, 2005). These compositions include by injection, oral (including tablets and capsules containing gastro-intestinal drug absorption extenders and enhancers), intravenous and the like.

Preferably, the inhibiting or reducing, or treating is by administering an injection by the intra-muscular (IM) or sub-cutaneous (SC) routes, an intraventricular route, intracisternal route or intrathecal route, intra-venously (IV), intra-articularly (IA), peri-articularly, topically, via suppositories or orally.

The present disclosure contemplates inhibiting or reducing Nerve Growth Factor (NGF) or pro-Nerve Growth Factor (pro-NGF) activity in a mammal, or treating NGF or pro-NGF mediated pain in a mammal by administering a polysulfated polysaccharide or an acceptable salt thereof to the mammal in an effective amount in the range of about 10 ng to about 1000 ng as a fixed dose. In certain embodiments, the effective amount is in the range of about 50 ng to about 950 ng; about 100 ng to about 900 ng; about 150 ng to about 850 ng; about 200 ng to about 800 ng; about 250 ng to about 750 ng; about 300 ng to about 700 ng; about 350 ng to about 650 ng; about 400 ng to about 600 ng; about 450 ng to about 500 ng as a fixed dose. In certain embodiments, the effective amount is a fixed dose of about 10 ng, about 50 ng, about 100 ng, about 150 ng, about 200 ng, about 250 ng, about 300 ng, about 350 ng, about 400 ng, about 450 ng, about 500 ng, about 550 ng, about 600 ng, about 650 ng, about 700 ng, about 750 ng, about 800 ng, about 850 ng, about 900 ng, about 950 ng or about 1000 ng.

In regard to the above doses (i.e. those doses ranging from about 10 ng to about 1000 ng), the inhibiting or reducing, or treating is preferably by administering an injection of the polysulfated polysaccharide or the acceptable salt thereof by an intraventricular, intracisternal or intrathecal route.

The present disclosure contemplates inhibiting or reducing Nerve Growth Factor (NGF) or pro-Nerve Growth Factor (pro-NGF) activity in a mammal, or treating NGF or pro-NGF mediated pain in a mammal by administering the polysulfated polysaccharide or the acceptable salt thereof to the mammal in an effective amount in the range of about 10 μg to about 1000 μg as a fixed dose. In certain embodiments, the effective amount is about 50 μg to about 950 μg; about 100 μg to about 900 rig; about 150 μg to about 850 μg; about 200 μg to about 800 μg; about 250 μg to about 750 μg; about 300 μg to about 700 μs; about 350 μg to about 650 μg; about 400 μg to about 600 μg; about 450 μs to about 500 μg as a fixed dose. In certain embodiments, the effective amount is a fixed dose of about 10 μg, about 50 μg, about 100 μg, about 150 μg, about 200 μg, about 250 μg, about 300 μg, about 350 μg, about 400 μg, about 450 μg, about 500 μg, about 550 μg, about 600 μg, about 650 μg, about 700 μg, about 750 μg, about 800 μg, about 850 μg, about 900 μg, about 950 μs or about 1000 μg.

In regard to the above doses (i.e. those ranging from about 10 μg to about 1000 μg), the inhibiting or reducing, or treating is preferably by administering an injection of the polysulfated polysaccharide or the acceptable salt thereof by an intraventricular, intracisternal or intrathecal route.

Preferably, the inhibiting or reducing, or treating is by administering the polysulfated polysaccharide or the acceptable salt thereof to the mammal in an effective amount of about 1 mg/kg to about 2 mg/kg of the mammal per dose.

Preferably, the inhibiting or reducing, or treating is by administering the polysulfated polysaccharide or the acceptable salt thereof to the mammal in an effective amount of about 2 mg/kg of the mammal per dose. The effective amount is preferably about 1.0 to 2.0 mg/kg of the subject per dose. In certain embodiments, the effective amount is about 1.0 to 1.5 mg/kg; 1.5 to 2.0 mg/kg; 0.5 mg/kg; 1.0 mg/kg; 1.5 mg/kg; or 2.0 mg/kg.

The present disclosure contemplates inhibiting or reducing Nerve Growth Factor (NGF) or pro-Nerve Growth Factor (pro-NGF) activity in a mammal, or treating NGF or pro-NGF mediated pain in a mammal by administering a polysulfated polysaccharide or an acceptable salt thereof to the mammal in an effective amount in the range of about 1 mg to about 25 mg as a fixed dose. In certain embodiments, the effective amount is a fixed dose in the range between about 2 mg and about 24 mg; about 3 mg and about 23 mg; about 4 mg and about 22 mg; about 5 mg and about 21 mg; about 6 mg and about 20 mg; about 7 mg and about 19 mg; about 8 mg and about 18 mg; about 9 mg and about 17 mg; about 10 mg and about 16 mg; about 11 mg and about 15 mg; about 12 mg and about 14 mg. In certain embodiments, the effective amount is a fixed dose of about 1 mg, about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, about 21 mg, about 22 mg, about 23 mg, about 24 mg or about 25 mg.

In certain embodiments, the effective amount is a fixed dose of between about 25 mg and 4000 mg. In certain embodiments, the effective amount is a fixed dose of about 25 mg, 50 mg, 75 mg, 100 mg, 125 mg, 150 mg, 175 mg, 200 mg, 225 mg, 250 mg, 275 mg, or 300 mg. In certain embodiments, the effective amount is a fixed dose of about 350 mg, 400 mg, 450 mg, 500 mg, 550 mg, 600 mg, 650 mg, 700 mg, 750 mg, 800 mg, 850 mg, 900 mg, 950 mg, 1000 mg, 2000 mg, 3000 mg, or 4000 mg.

Preferably, the administering is by an injection. The administering is preferably by a sub-cutaneous (SC) injection. Preferably, the SC injection is slow SC injection. The administering is preferably by an intramuscular (IM) injection.

Preferably, administration to a human is by dosing in a treatment regimen once daily, twice weekly or thrice weekly. The administration to a human is preferably by dosing in a treatment regimen twice weekly. Preferably, the administration to a human is by dosing in a treatment regimen twice weekly with a minimum of three days and a maximum of four days between dosages. The administration to a human is preferably by dosing in a treatment regimen twice weekly for six weeks. Preferably, the total dose of polysulfated polysaccharide administered in the treatment regimen is about 200 to 4000 mg.

Thus, the dosage would be adjusted accordingly for heavier or lighter weighted individuals. The treatment regimen may be adapted according to the severity of the pain experienced by the subject. In some instances where a patient is experiencing high level pain, it is desirable to reach a therapeutic loading of the PPS as quickly as possible. This may necessitate, for example, the administration of about 1.0 mg/kg or more PPS daily until the pain is resolved.

When administration is by injection, this would normally be carried out in a clinical situation by a nurse/doctor. The person skilled in the art would understand that the key to successful treatment is to administer sufficient PPS to the subject to achieve an optimum therapeutic dose. Since it is known that PPS accumulates in connective tissues, loading can be achieved over time, eg daily doses of 1 mg PPS/kg over 4-5 days. It would be expected that for severe chronic cases the subject may require more than one course of treatment per year maybe twice or thrice per year.

From a safety point of view a lower dose range (1-2 mg PPS/kg or a fixed dose of about 25-50 mg) over a longer period and with decreased frequency of administration is preferred. This is because PPS is a known anticoagulant and the basal APT may be elevated with the higher dose (>3 mg PPS/kg or a fixed dose of about 150-200 mg) which could potentially encourage bleeding of any open wounds.

Whilst administration by injection is preferred, oral or topical formulations of PPS may be used as follow-up (maintenance dose) for the initial IM or SC PPS treatments. This would also be applicable to oral dosing. For administration by IV infusion, the lower doses of 0.5-1 mg PPS/kg daily are preferred.

The present disclosure also contemplates co-administration of other therapeutic agents with polysulfated polysaccharides, such as NGF-sequestering agents. When other therapeutic agents are employed in combination with the compounds of the present invention they may be used for example in amounts as noted in the Physician Desk Reference (PDR) or as otherwise determined by one of ordinary skill in the art.

It will be understood, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy. For example, it would be understood that large animals require larger doses. For illustration, a large animal like a horse may require a fixed dose of about 4000 mg.

The determination of the suitability of the treatment of the present disclosure may be assessed using patient reported outcome measurement instruments. Patient reported pain and/or functional outcomes may be used. These include the Numerical Rating Scale (NRS) for pain [17]; the Lysholm Knee Score for function [18]; Knee injury and Osteoarthritis Outcome Score (KOOS) [19] for pain, symptoms, function and quality of life; and the Oswestry Disability Index (also known as the Oswestry Low Back Pain Disability Questionnaire) for low back function [20].

Preferably, pain in the mammal is reduced after administration. Pain in the mammal is reduced as preferably determined by a rating scale. Preferably, the rating scale is the numerical rating scale (NRS).

Preferably, administration of the polysulfated polysaccharide or the acceptable salt thereof further maintains or improves mammal health. Preferably, administration of the polysulfated polysaccharide or the acceptable salt thereof further maintains mammal body weight. Preferably, administration of the polysulfated polysaccharide or the acceptable salt thereof further maintains or improves musculoskeletal integrity and/or function. Preferably, administration of the polysulfated polysaccharide or the acceptable salt thereof further maintains or improves skeletal integrity and/or function. Preferably, administration of the polysulfated polysaccharide or the acceptable salt thereof further maintains or improves the integrity and/or function of a joint or a bone. Preferably, administration of the polysulfated polysaccharide or the acceptable salt thereof further maintains or improves the integrity and/or function of bone.

Preferably, administration of the polysulfated polysaccharide or the acceptable salt thereof prevents cancer-induced bone fracture, wherein the mammal is suffering from bone cancer. Preferably, administration of the polysulfated polysaccharide or the acceptable salt thereof delays the time to cancer-induced bone fracture, wherein the mammal is from bone cancer. Preferably, administration of the polysulfated polysaccharide or the acceptable salt thereof prevents or ameliorates bone loss. Preferably, administration of the polysulfated polysaccharide or the acceptable salt thereof prevents or ameliorates dysregulation of mineral homeostasis. Preferably, the mineral homeostasis is calcium and/or phosphate homeostasis. Preferably, administration of the polysulfated polysaccharide or the acceptable salt thereof prevents or ameliorates nerve compression syndromes.

Preferably, function in the mammal is improved after treatment. The function in the mammal is preferably improved as determined by the Lysholm Knee Score.

Figure 4:
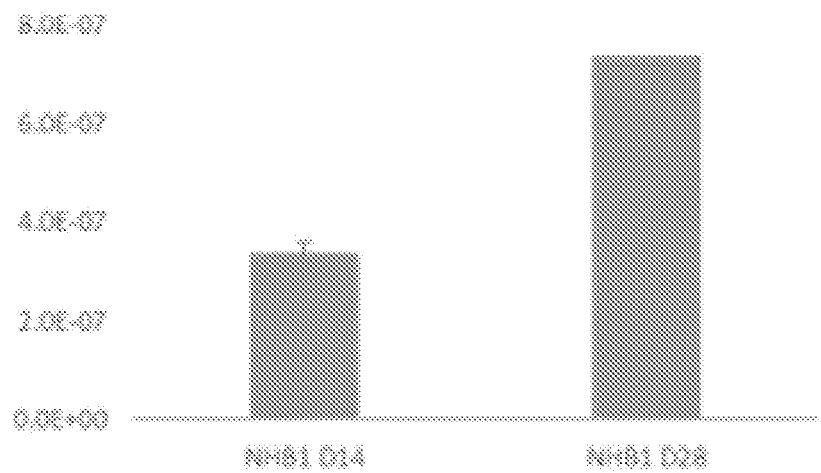
Figure 4:
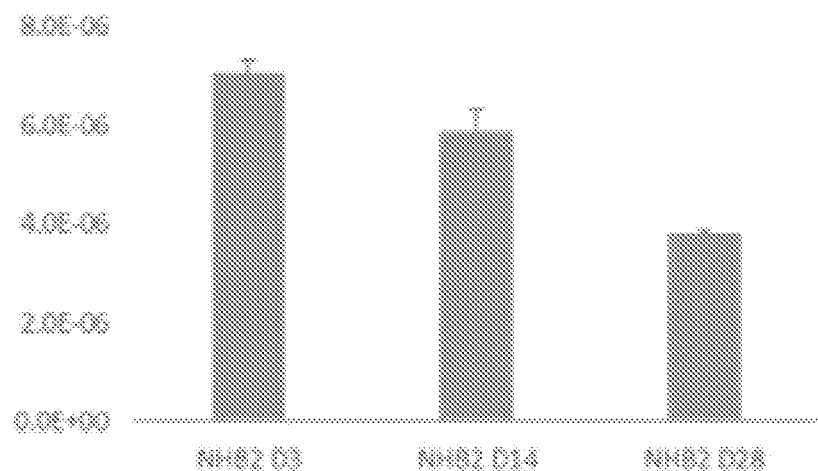
Figure 4:
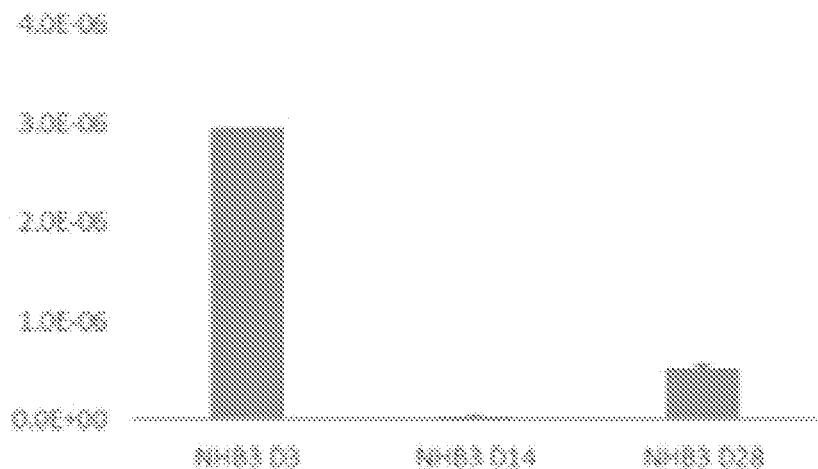

FIG. 4. Gene expression of osteoblast/osteocyte differentiation markers in KOA cultures from three donors (KOA1-3): SOST. A) KOA1-SOST:18S mRNA expression; B) KOA2-SOST:18S mRNA expression; and C) KOA3-SOST: 18S mRNA expression. Data are triplicate real-time RT-PCR reactions (mean+standard deviation (SD)) relative to the expression of 18S rRNA.

Figure 5:
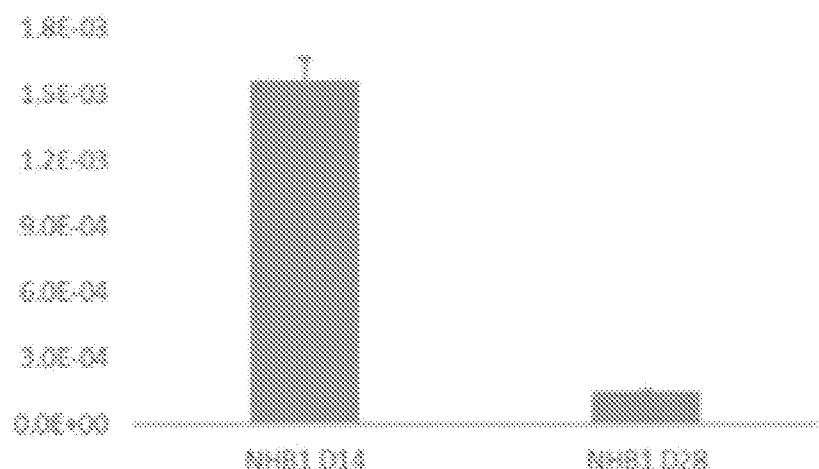
Figure 5:
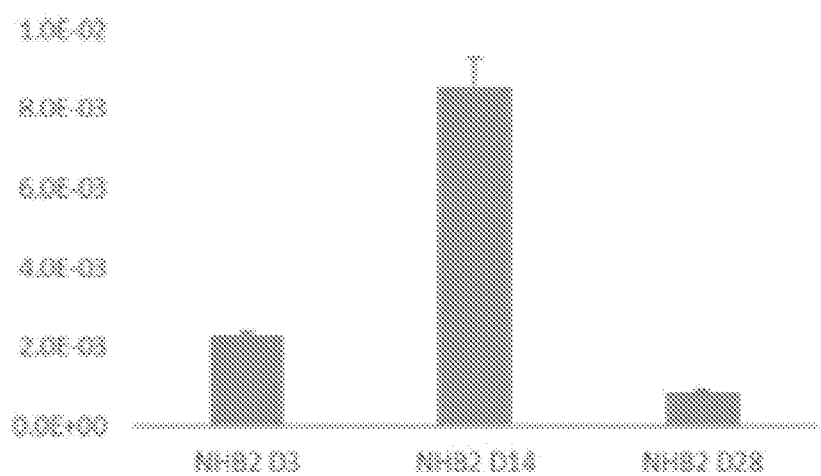
Figure 5:
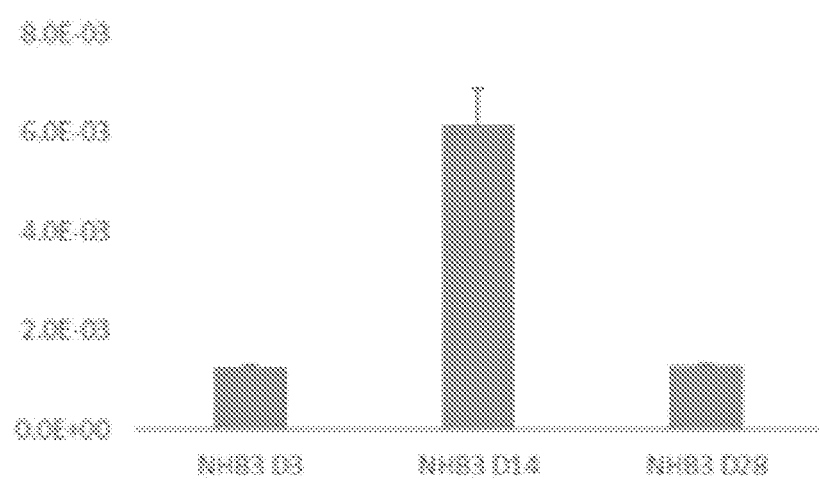

FIG. 5. Gene expression of osteoblast/osteocyte differentiation markers in KOA cultures from three donors (KOA1-3): OCN. A) KOA1-OCN:18S mRNA expression; B) KOA2-OCN:18S mRNA expression; and C) KOA3-OCN: 18S mRNA expression. Data are triplicate real-time RT-PCR reactions (mean+standard deviation (SD)) relative to the expression of 18S rRNA.

Figure 6:
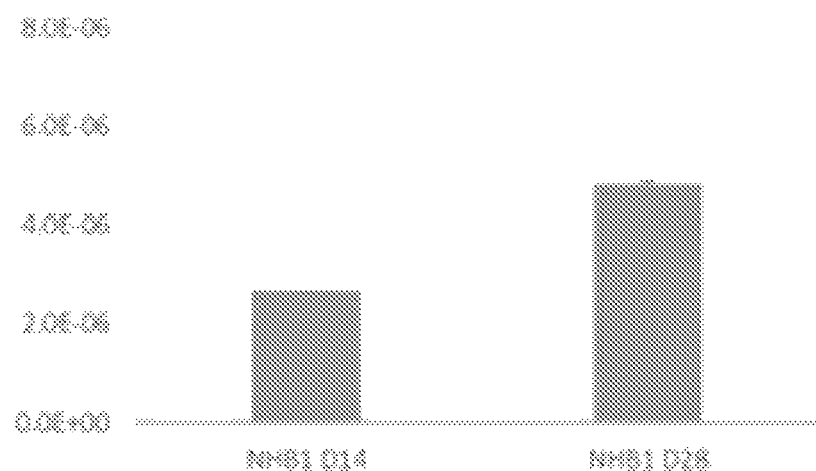
Figure 6:
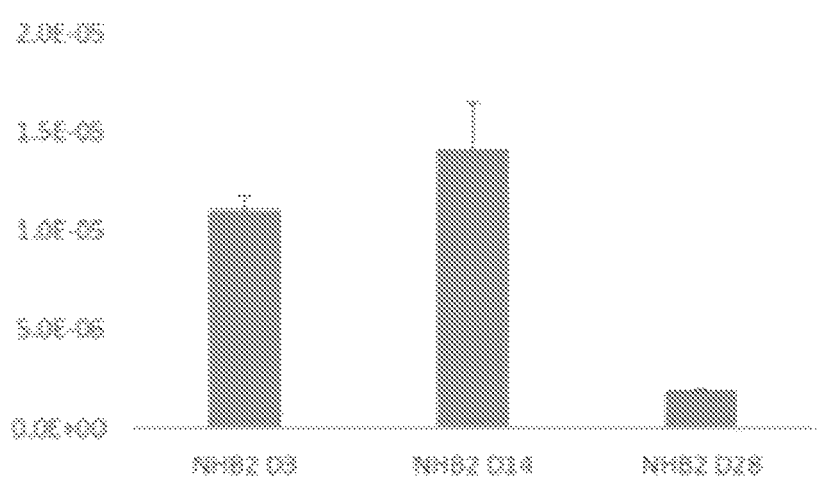
Figure 6:
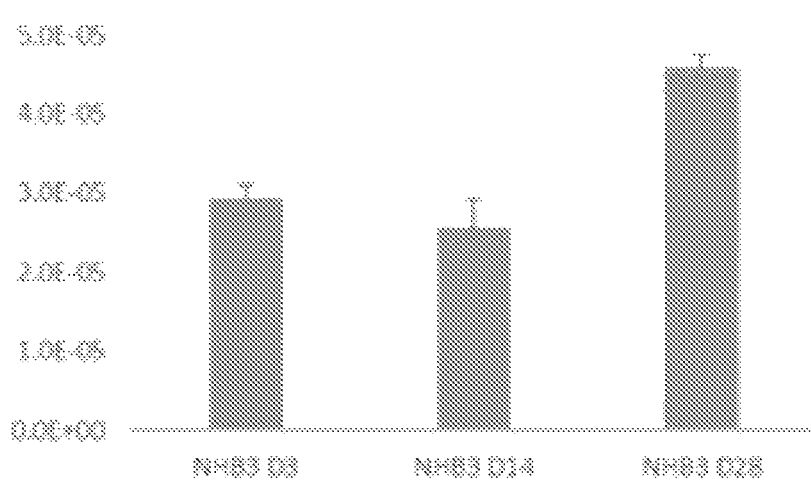

FIG. 6. Gene expression of osteoblast/osteocyte differentiation markers in KOA cultures from three donors (KOA1-3): RANKL. A) KOA1-RANKL:18S mRNA expression; B) KOA2-RANKL:18S mRNA expression; and C) KOA3-RANKL:18S mRNA expression. Data are triplicate real-time RT-PCR reactions (mean+standard deviation (SD)) relative to the expression of 18S rRNA.

Figure 7:
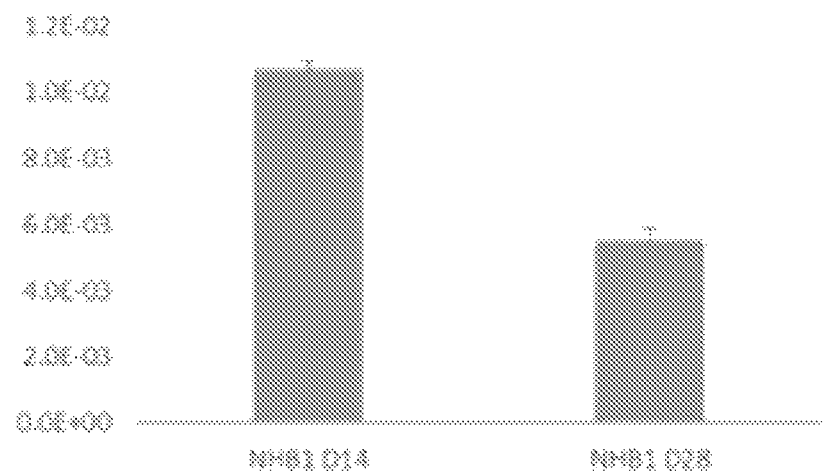
Figure 7:
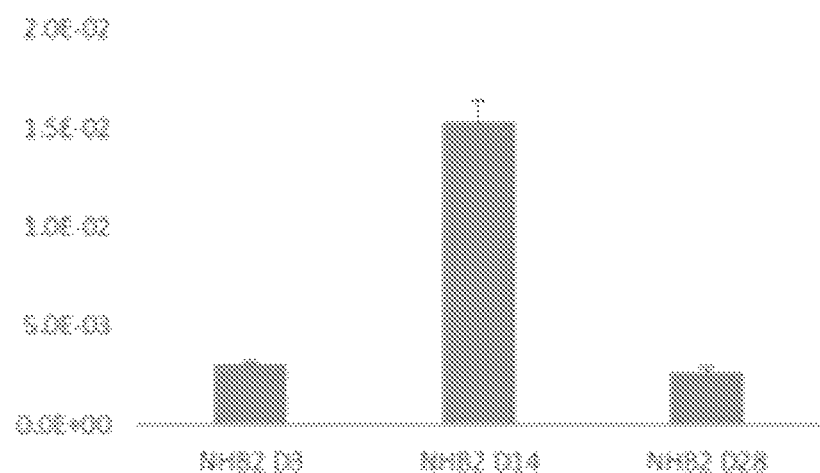
Figure 7:
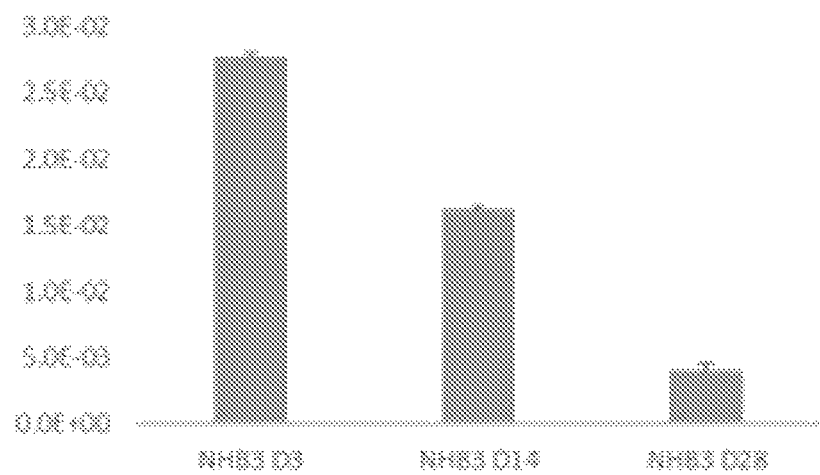

FIG. 7. Gene expression of osteoblast/osteocyte differentiation markers in KOA cultures from three donors (KOA1-3): OPG. A) KOA1-OPG:18S mRNA expression; B) KOA2-OPG:18S mRNA expression; and C) KOA3-OPG:18S mRNA expression. Data are triplicate real-time RT-PCR reactions (mean+standard deviation (SD)) relative to the expression of 18S rRNA.

Figure 8:
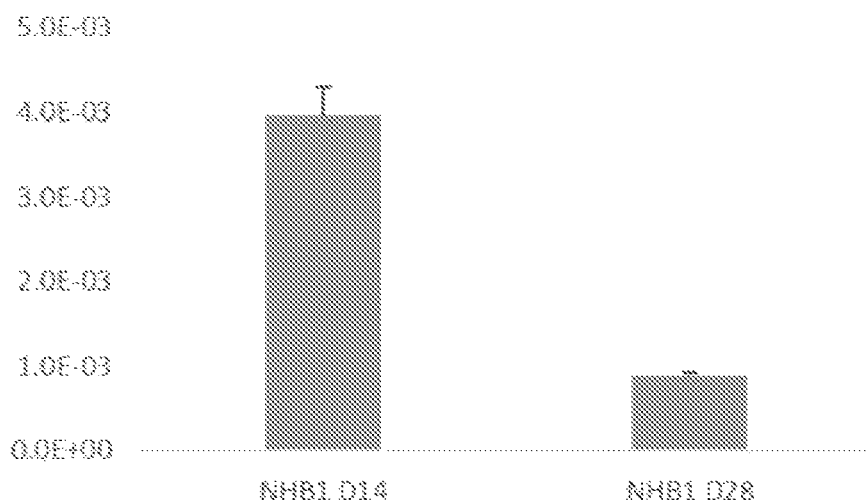
Figure 8:
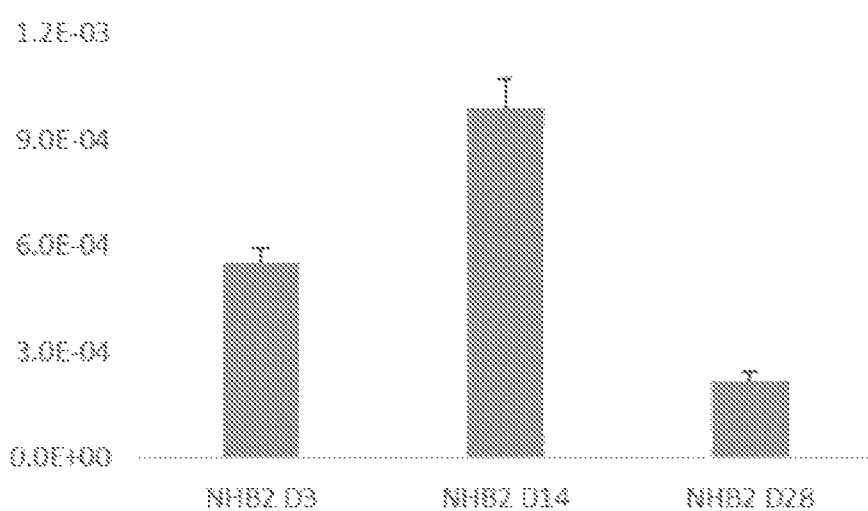
Figure 8:
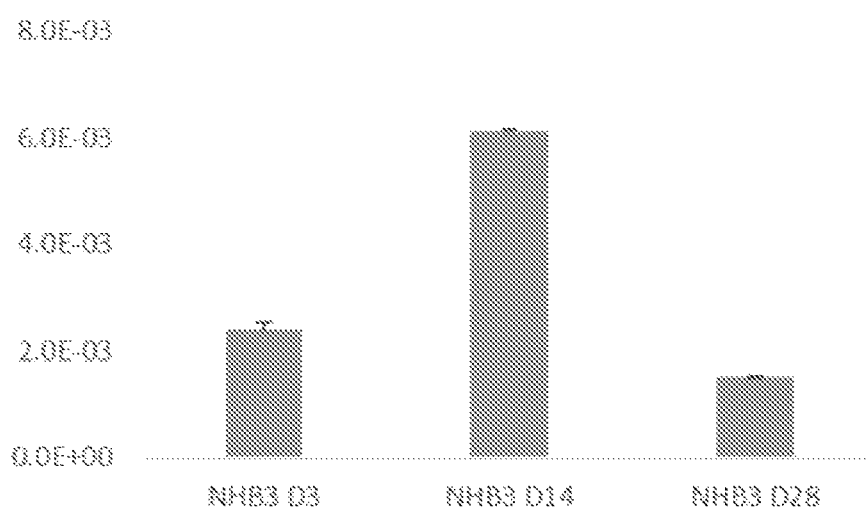

FIG. 8. NGF expression by human osteocytes. Relative NGF mRNA expression across differentiation of KOA cultures for the 3 donors analysed. Data are triplicate real-time RT-PCR reactions (mean+standard deviation (SD)) relative to the expression of 18S rRNA. A) KOA1-NGF:18S mRNA expression; B) KOA2-NGF:18S mRNA expression; and C) KOA3-NGF:18S mRNA expression.

Figure 9:
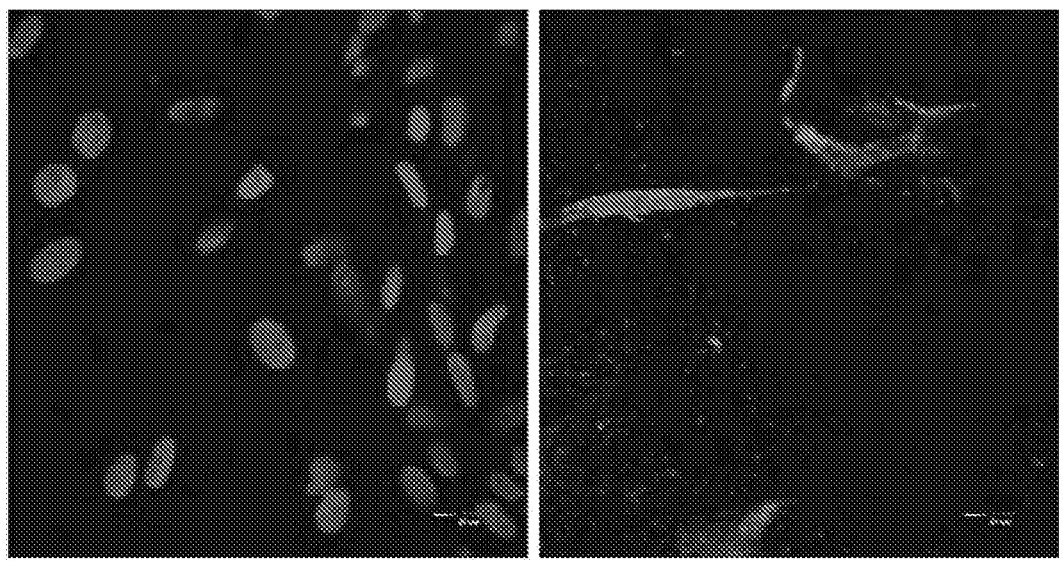

FIG. 9. Confocal microscopy images showing NGF protein expression (red) by freshly harvested human osteocytes (rhs) compared with isotype control IgG immunostain (lhs) *. Nuclei (blue) are stained with DAPI.

Figure 10:
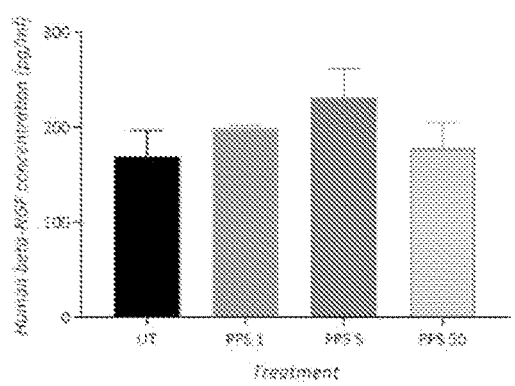
Figure 10:
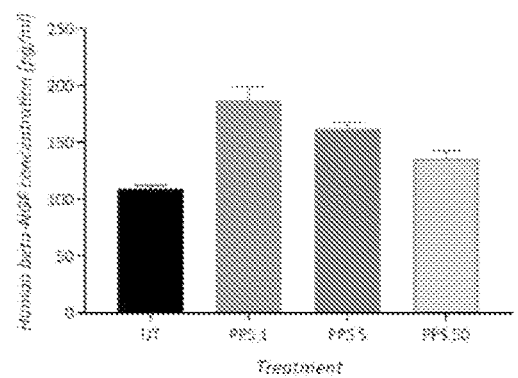
Figure 10:
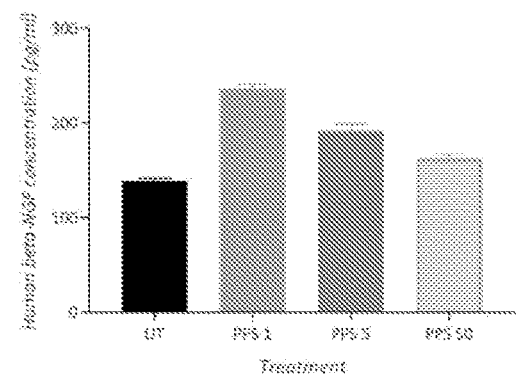
Figure 10:
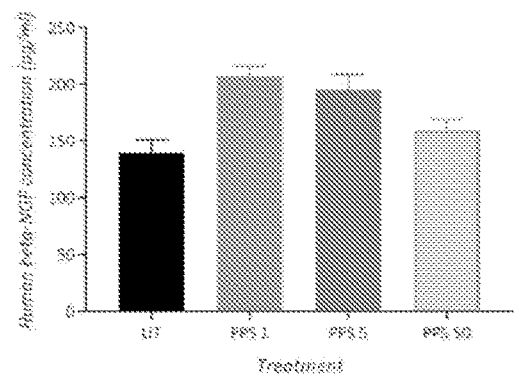

FIG. 10. Secreted levels of NGF protein, as determined by human NGF ELISA, in cultures of 28d differentiated NOF osteocyte-like cells either untreated (UT) for a further 72 h or pre-treated for the same period with PPS at 1, 5 and 50 µg/mL. Data are means of triplicate reactions+SD. A) ~NOF1; B) -NOF2; C) -NOF3; and D) NOF: All Donors.

Figure 11:
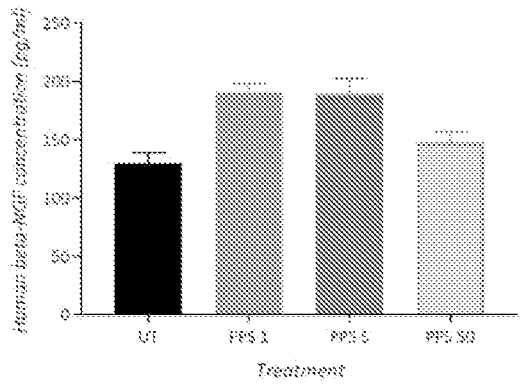
Figure 11:
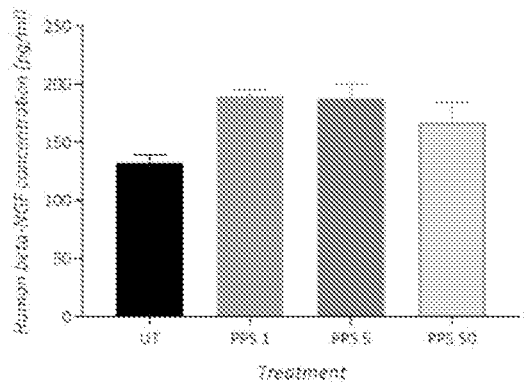
Figure 11:
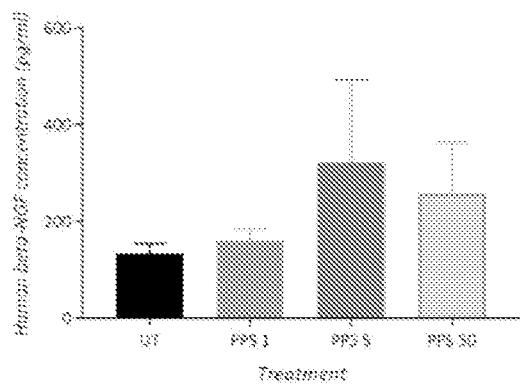
Figure 11:
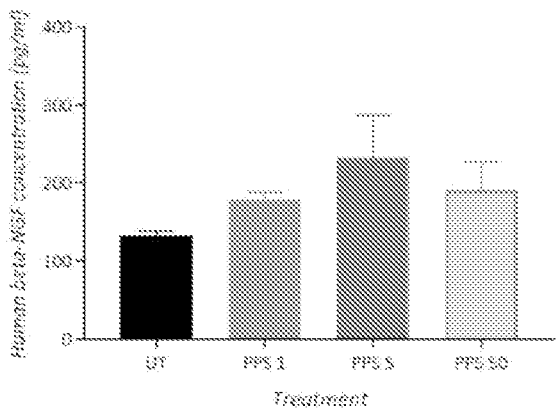

FIG. 11. Secreted levels of NGF protein, as determined by human NGF ELISA, in cultures of 28d differentiated KOA osteocyte-like cells either untreated (UT) for a further 72 h or pre-treated for the same period with PPS at 1, 5 and 50 µg/mL. Data are means of triplicate reactions+SD. A) -KOA1; B) -KOA2; C) -KOA3; and D) KOA: All Donors.

Figure 12:
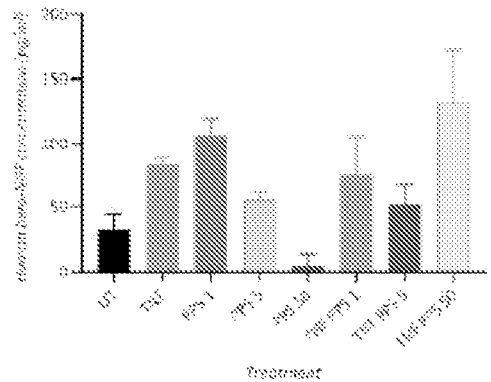
Figure 12:
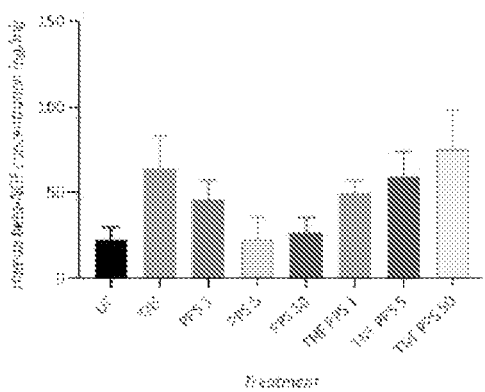
Figure 12:
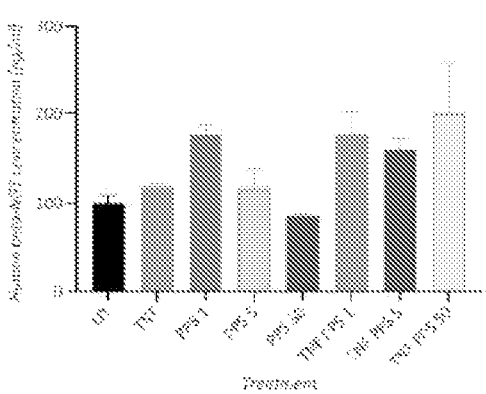
Figure 12:
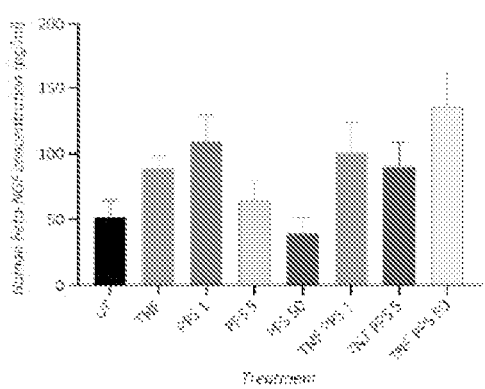

FIG. 12. Apparent levels of NGF secreted by NOF osteocyte-like cultures in response to combinations of rhTNF and PPS. Data are means+SD of supernatants harvested from triplicate wells. A) -NOF1; B) -NOF2; C) -NOF3; and D) NOF: All Donors.

Figure 13:
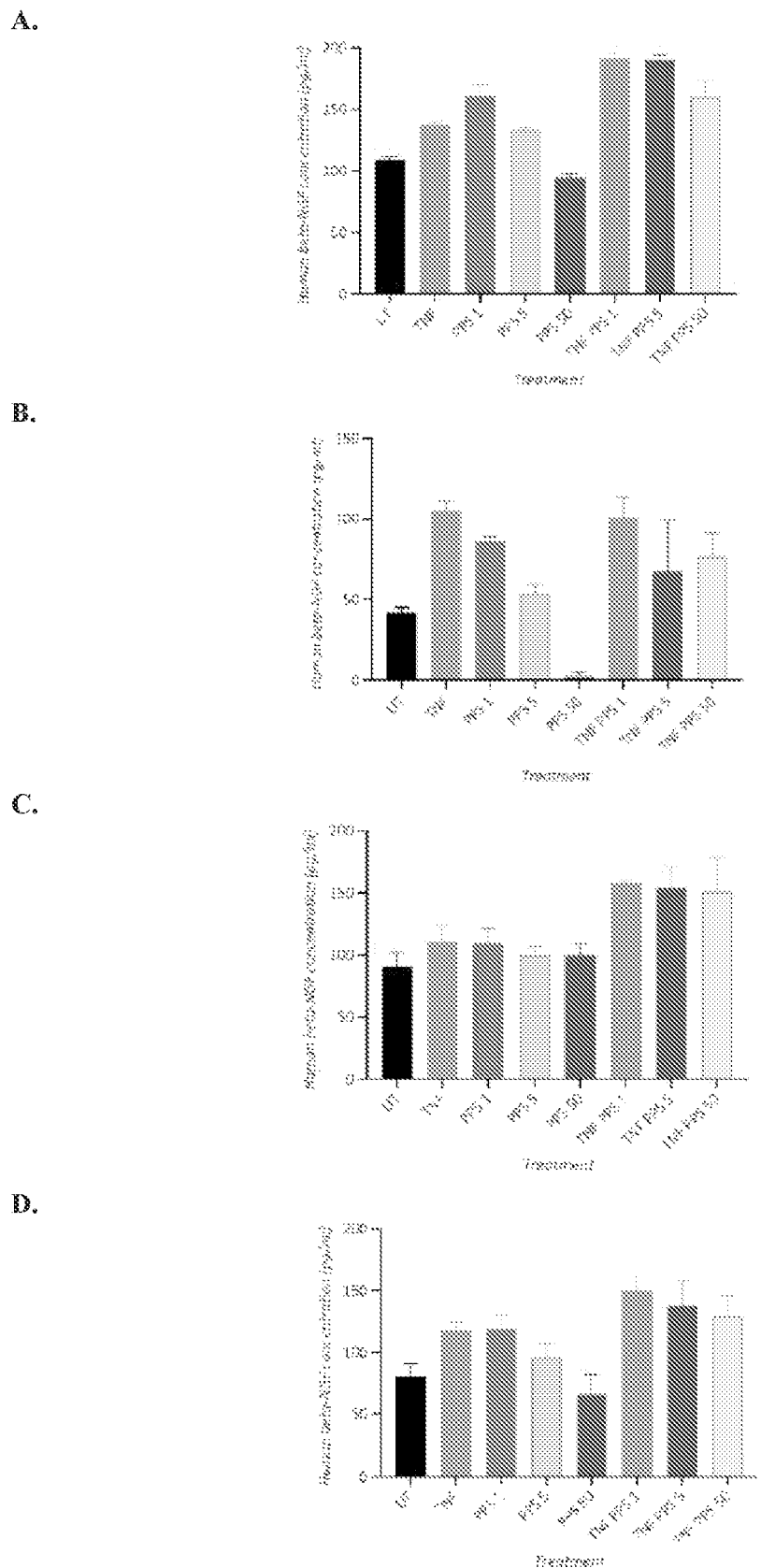

FIG. 13. Apparent levels of NGF secreted by KOA osteocyte-like cultures in response to combinations of rhTNF and PPS. Data are means+SD of supernatants harvested from triplicate wells. A) -KOA1; B) -KOA2; C) -KOA3; and D) KOA: All Donors.

Figure 14:
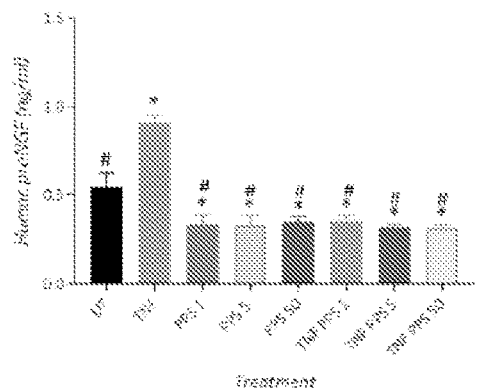
Figure 14:
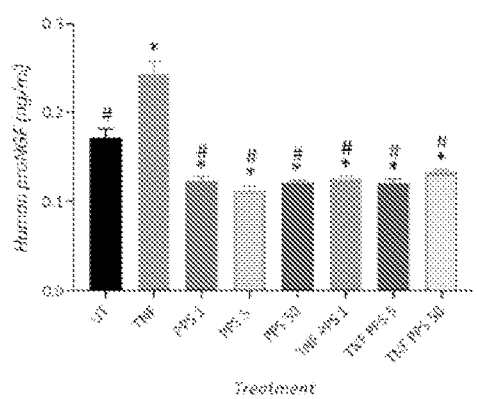
Figure 14:
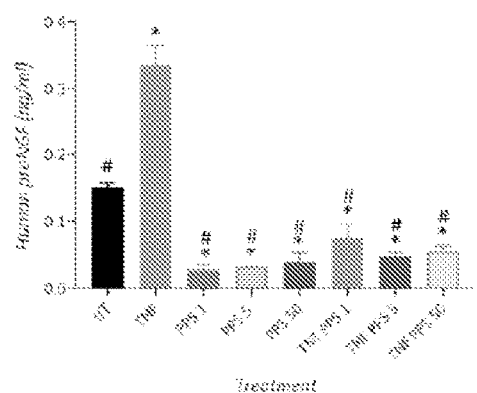
Figure 14:
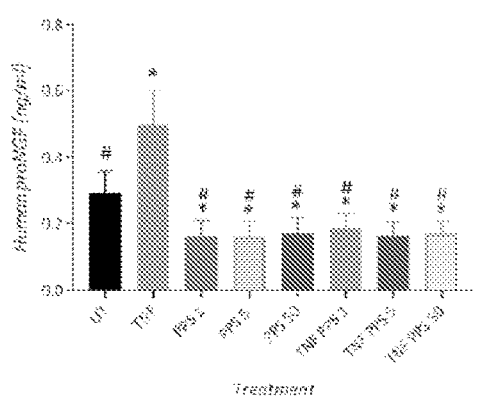

FIG. 14. Secretion of proNGF from cultures of NOF osteocyte-like cells treated with combinations of rhTNF and PPS. Data are means+SD of supernatants harvested from triplicate wells. Significant difference to untreated control (UT) is indicated by *($p<0.05$); significant difference to rhTNF treated cultures is indicated by #($p<0.05$). A) -NOF1; B) -NOF2; C) -NOF3; and D) NOF: All Donors.

Figure 15:
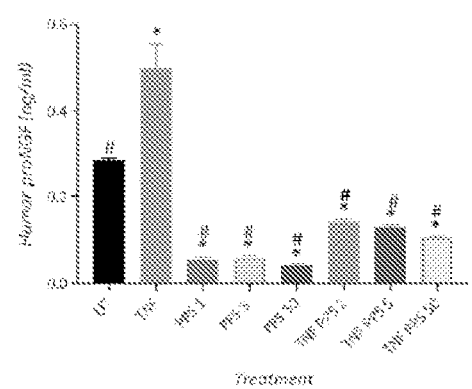
Figure 15:
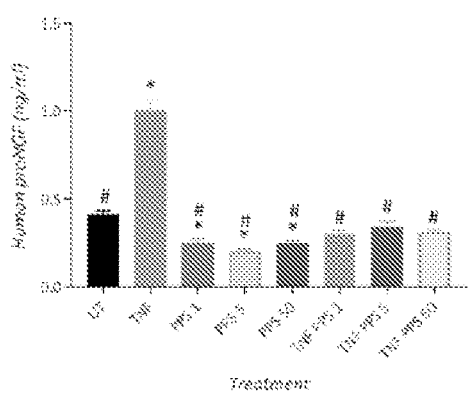
Figure 15:
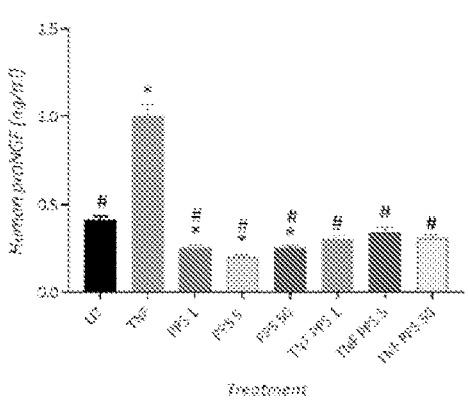
Figure 15:
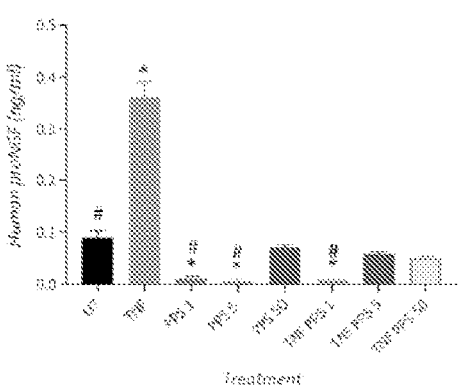

FIG. 15. Secretion of proNGF from cultures of NOF and KOA osteocyte-like cells treated with combinations of rhTNF and PPS. Data are means+SD of supernatants harvested from triplicate wells. Significant difference to untreated control (UT) is indicated by *($p<0.05$); significant difference to rhTNF treated cultures is indicated by #($p<0.05$). A) -KOA1; B) -KOA2; C) -KOA3; and D) KOA: All Donors.

Figure 16:
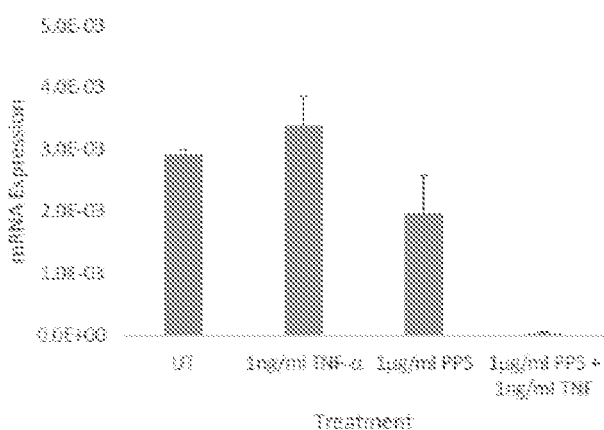
Figure 16:
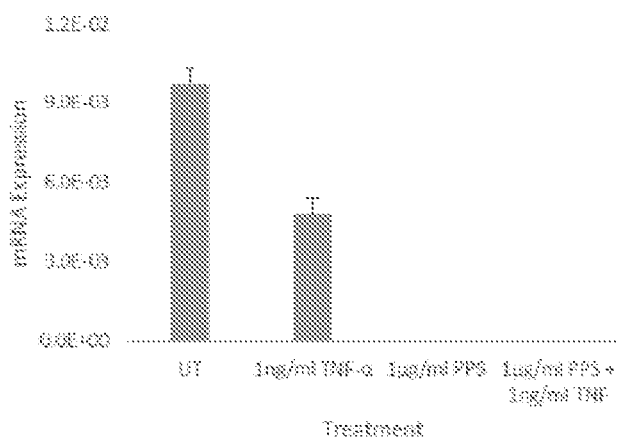

FIG. 16. Effects of combinations of rhTNF and PPS on gene expression in KOA osteocyte-like cultures. Real-time RT-PCR was performed for NGF mRNA. Data are mean+SD of triplicate real-time RT-PCR reactions relative to the expression of 18S rRNA. A) KOA1-NGFR:18S mRNA expression; B) KOA2-NGFR:18S mRNA expression.

Figure 17:
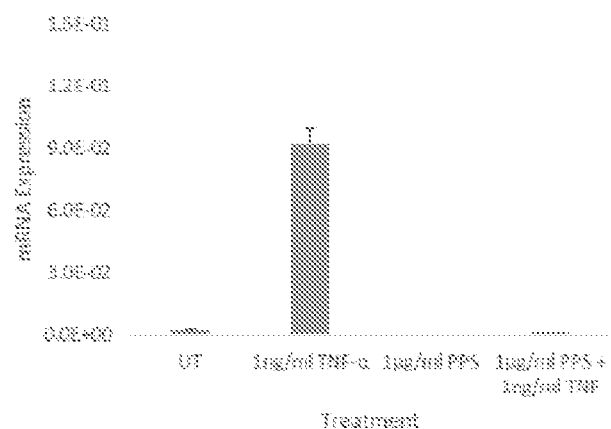
Figure 17:
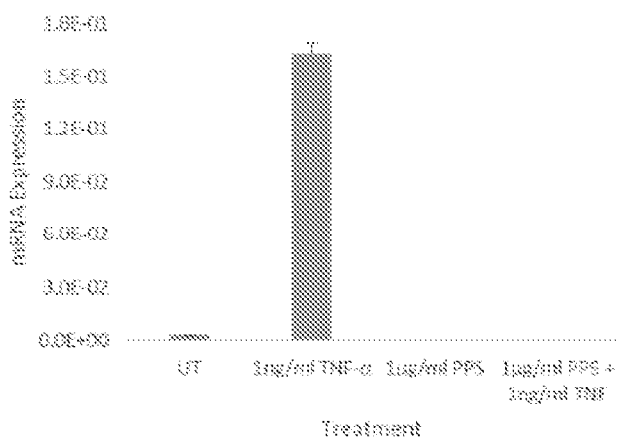

FIG. 17: Effects of combinations of rhTNF and PPS on gene expression in KOA osteocyte-like cultures. Real-time RT-PCR was performed for IL-6 mRNA. Data are mean+SD of triplicate real-time RT-PCR reactions relative to the expression of 18S rRNA. A) KOA1-IL6:18S mRNA expression; B) KOA2-IL6:18S mRNA expression.

Figure 18:
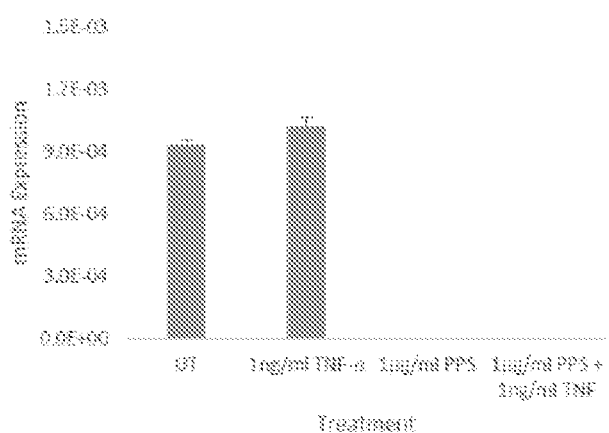
Figure 18:
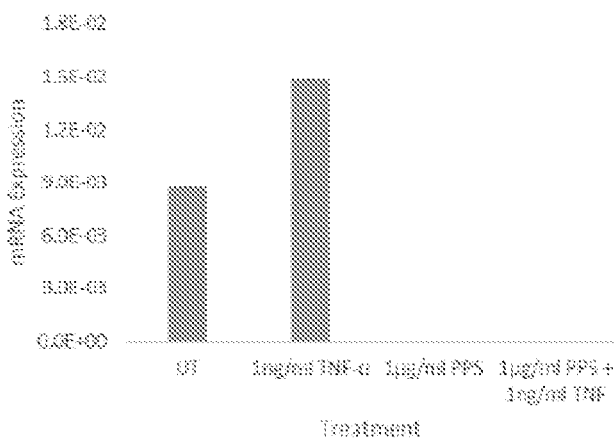

FIG. 18: Effects of combinations of rhTNF and PPS on gene expression in KOA osteocyte-like cultures. Real-time RT-PCR was performed for COX2 mRNA. Data are mean+SD of triplicate real-time RT-PCR reactions relative to the expression of 18S rRNA. A) KOA1-COX2:18S mRNA expression; B) KOA2-COX2:18S mRNA expression.

Figure 19:
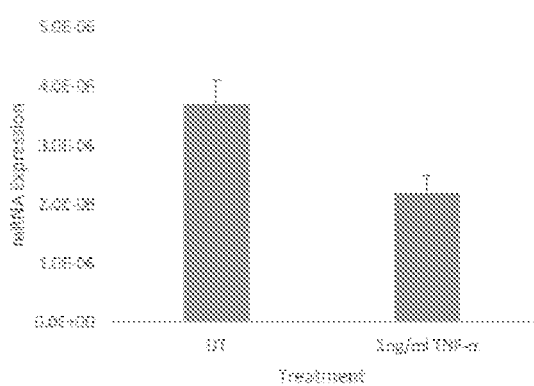
Figure 19:
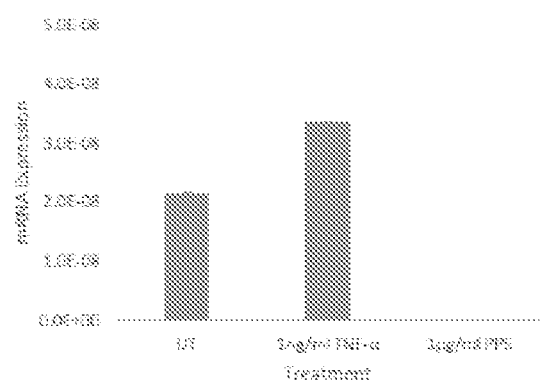
Figure 19:
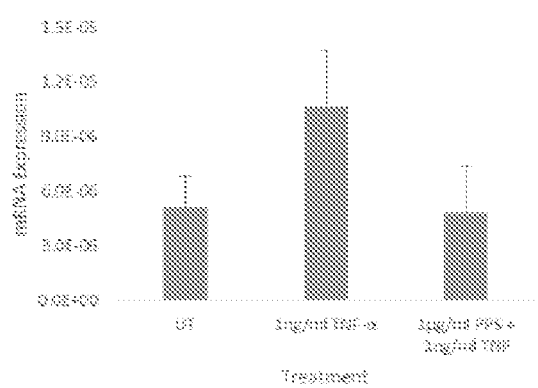
Figure 19:
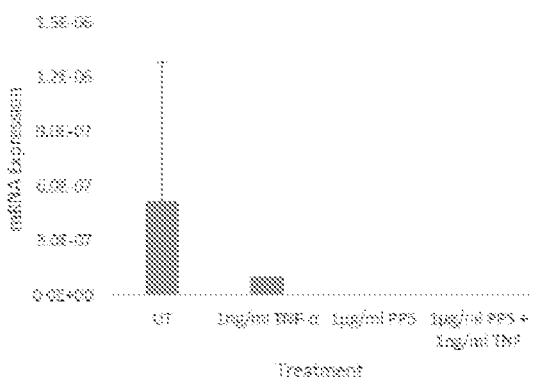

FIG. 19. Gene expression of NGF receptors in KOA1 and KOA2 osteocyte-like cultures. Real-time RT-PCR was performed for NGFR (P75NTR) and NTRKA (TrkA) mRNA. Data are mean+SD of triplicate real-time RT-PCR reactions relative to the expression of 18S rRNA. Note that in many cases, gene expression with a reliable melt-curve was undetectable or a PCR product was derived from only one or two of the triplicate reactions. A) KOA1-NGFR:18S mRNA expression; B) KOA1-NTRKA:18S mRNA expression; C) KOA2-NGFR:18S mRNA expression; and D) KOA2-NTRKA:18S mRNA expression.

Figure 20:
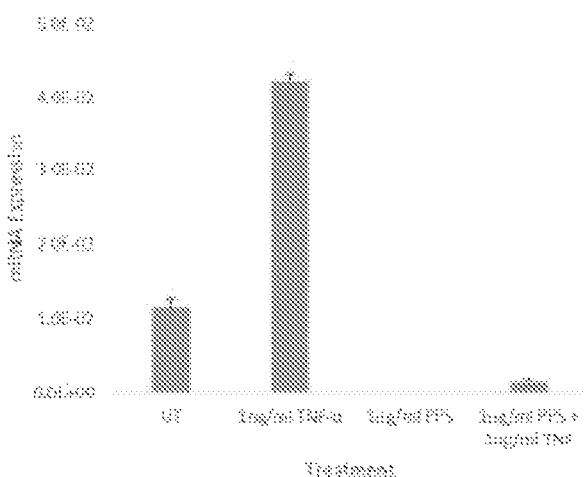
Figure 20:
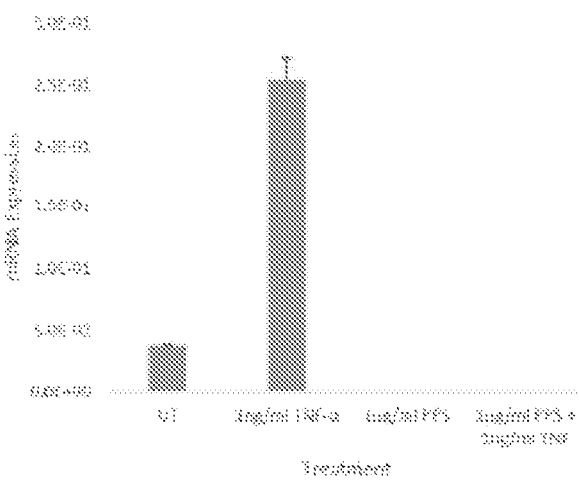

FIG. 20. The effect of PPS treatment on basal and TNFα-induced MMP13 expression in human KOA osteocyte-like cultures. Real-time RT-PCR analysis of MMP13 mRNA relative to the expression of 18S rRNA. Data are means+SD of triplicate real-time RT-PCR reactions. A) KOA1-MMP13:18S mRNA expression; and B) KOA2-MMP13:18S mRNA expression.

Figure 21:
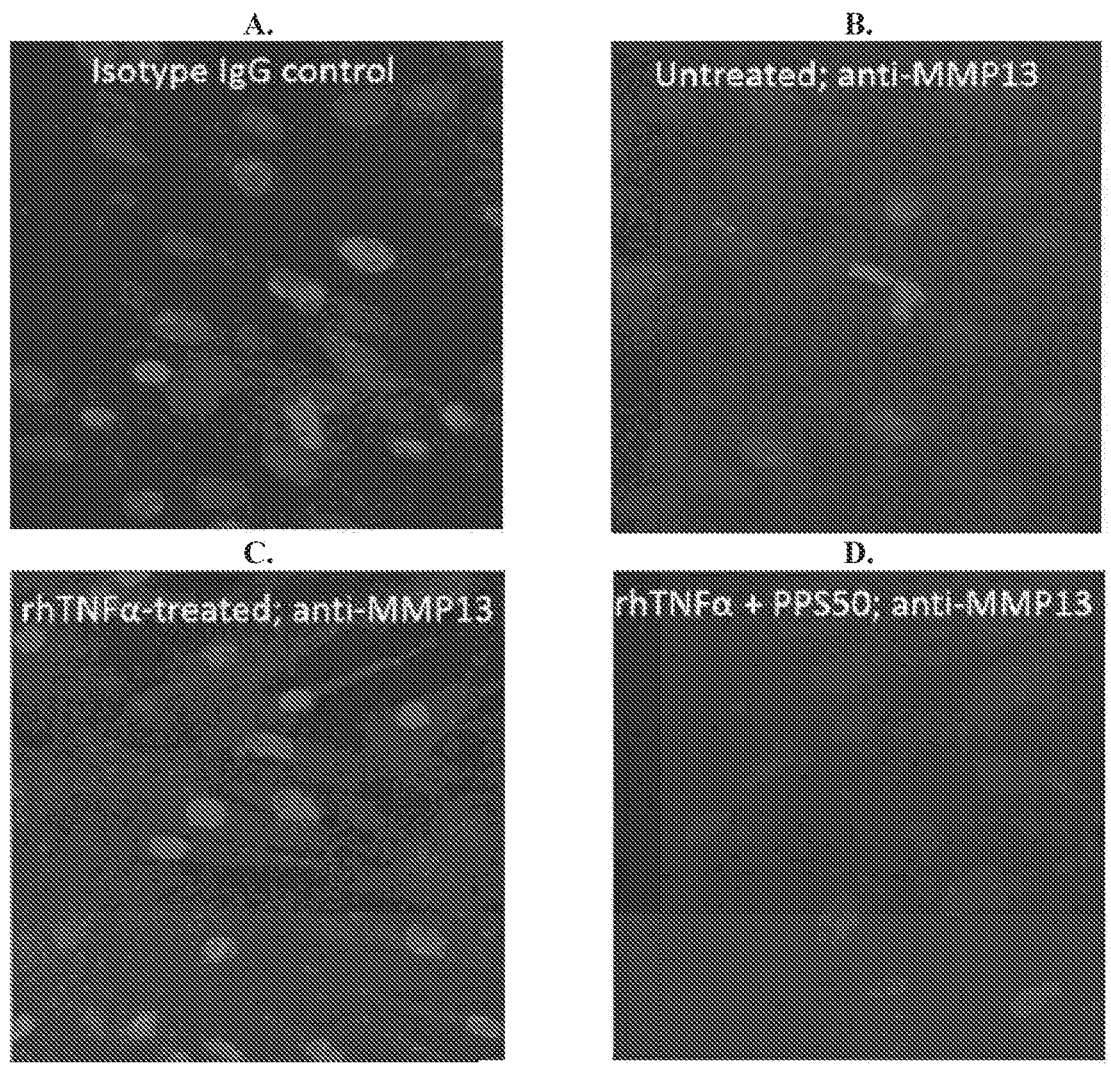

FIG. 21. The effect of PPS treatment on basal and TNFα-induced MMP13 expression in human KOA osteocyte-like cultures. Confocal microscopy imaging of immunostaining of KOA2 cells untreated stained with isotype control primary antibody or mouse anti-human anti-MMP13 antibody (top row), or treated with rhTNFα alone or rhTNFα+PPS (50 µg/mL) and stained for MMP13 (green staining). All nuclei are stained with DAPI (blue). A) Isotype IgG control; B) Untreated; anti-MMP13; C) rhTNF-α-treated; anti-MMP13; and D) rhTNFa+PPS50; anti-MMP13.

Figure 22:
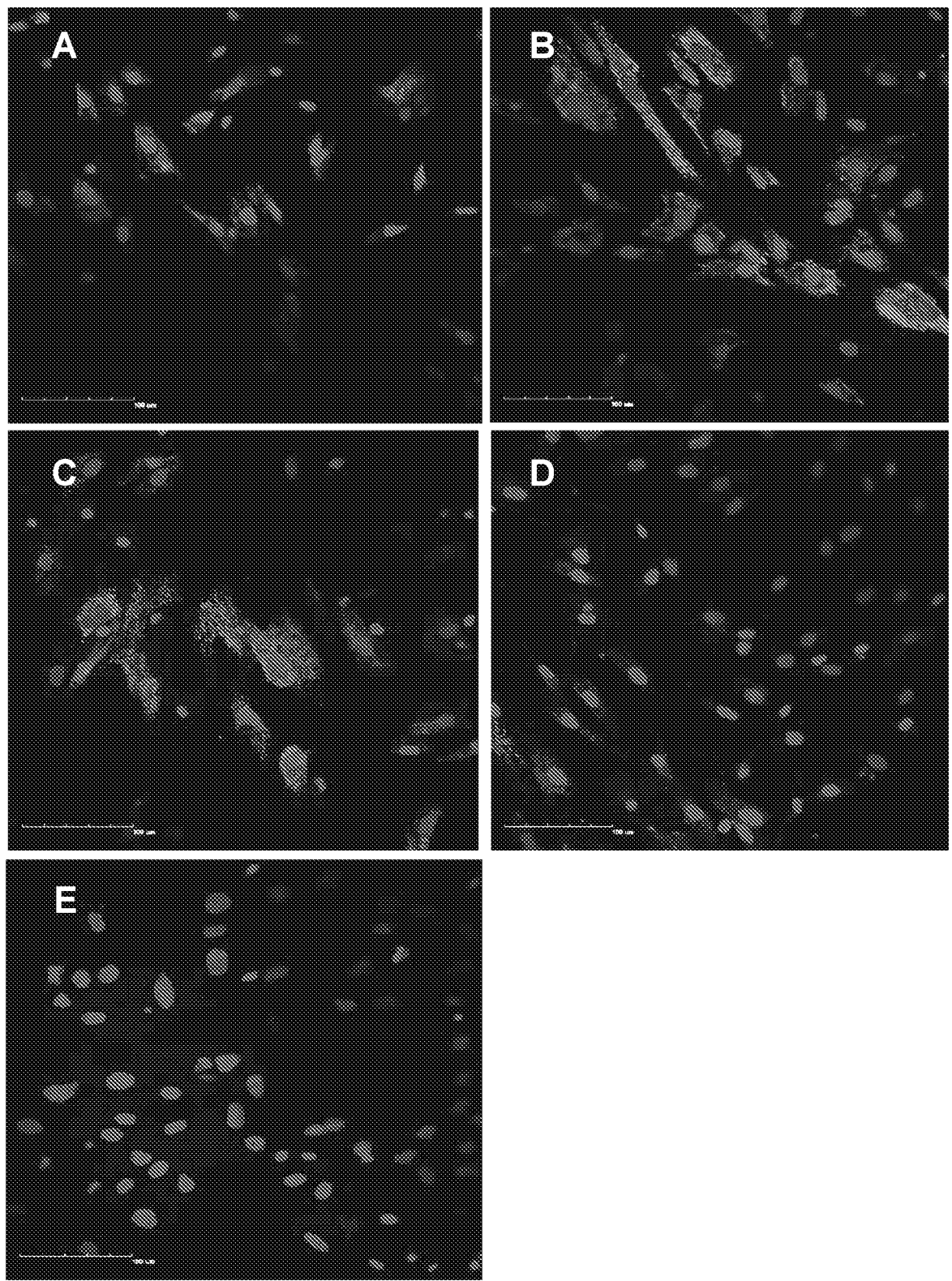

FIG. 22. NGF expression in isolated human osteocytes. Osteocyte-enriched fractions of sequential human trabecular bone digests were cultured for 24 h either untreated (A), treated with rhTNFα (B), PPS (0.5 µg/mL) (C) or a combination of both (D), and then examined by confocal microscopy for NGF immunoreactivity. Control cells were also immunostained using an isotype-matched negative control primary antibody (E). Images are representative of data obtained from two individual donors. Scale bars in each image represent 100 µm.

Figure 23:
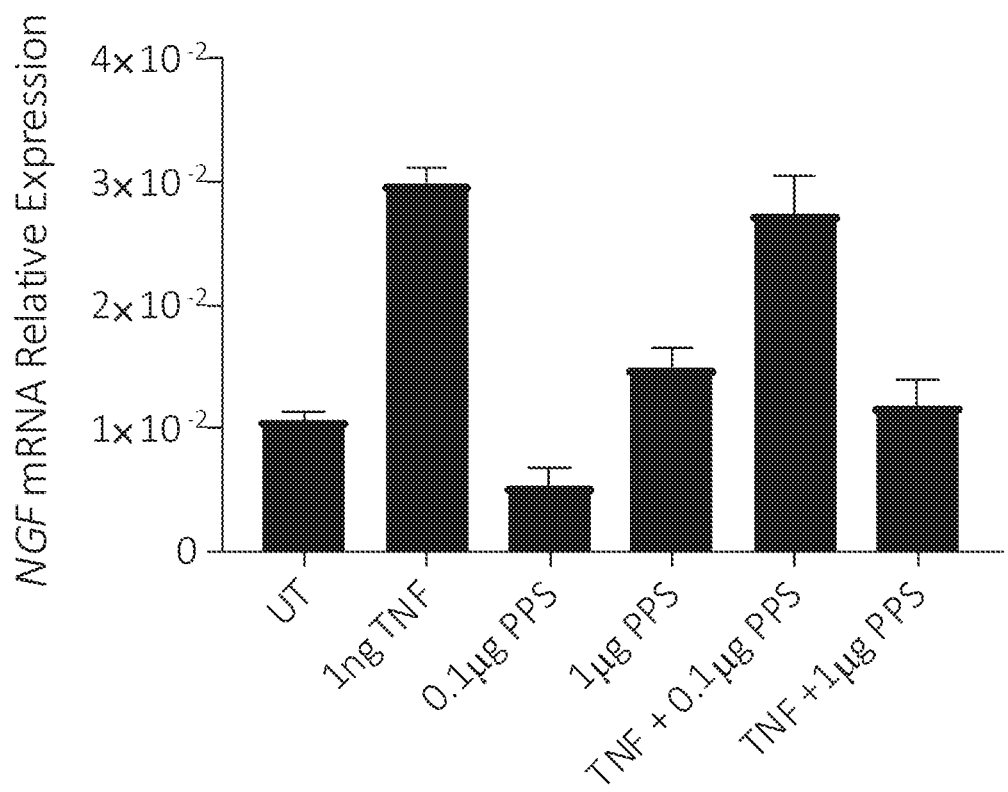

FIG. 23. Effects of combinations of rhTNF and PPS on NGF gene expression in osteocyte-like cultures. Human differentiated osteocyte-like cultures were either untreated or pretreated with PPS (0.1 or 1.0 µg/mL) for 24 h, then with or without rhTNFα (1 ng/mL) for a further 48 h, and then real-time RT-PCR was performed for NGF mRNA. Data are mean+SD of triplicate real-time RT-PCR reactions normalised to the mRNA expression of the housekeeping gene ACTB.

Figure 24:
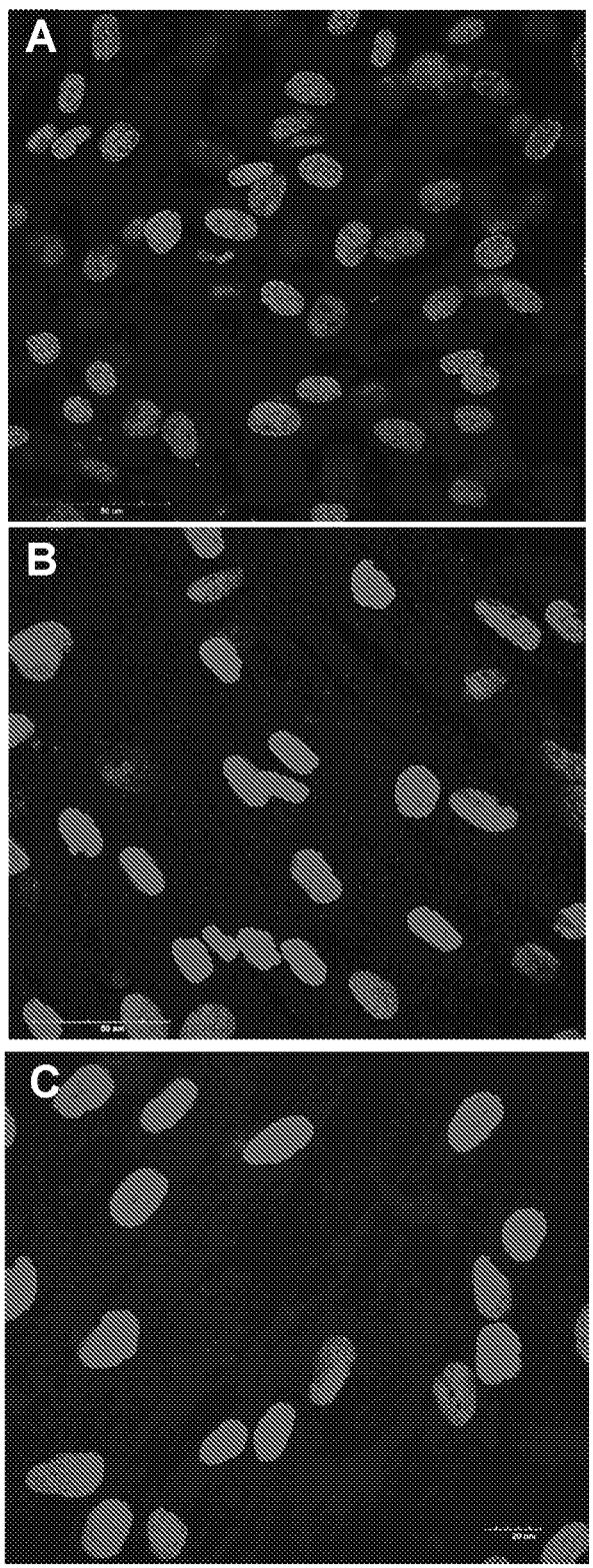

FIG. 24. Immunostaining of KOA-derived osteocytes for TrkA and P-75. Day 28 differentiated human primary osteocyte-like cultures were immunostained and examined by confocal microscopy, as described in Materials and Methods, for (A) TrkA (B) P-75 or were stained with an isotype control monoclonal antibody (C). Scale bars in each case represent 50 µm.

Figure 25:
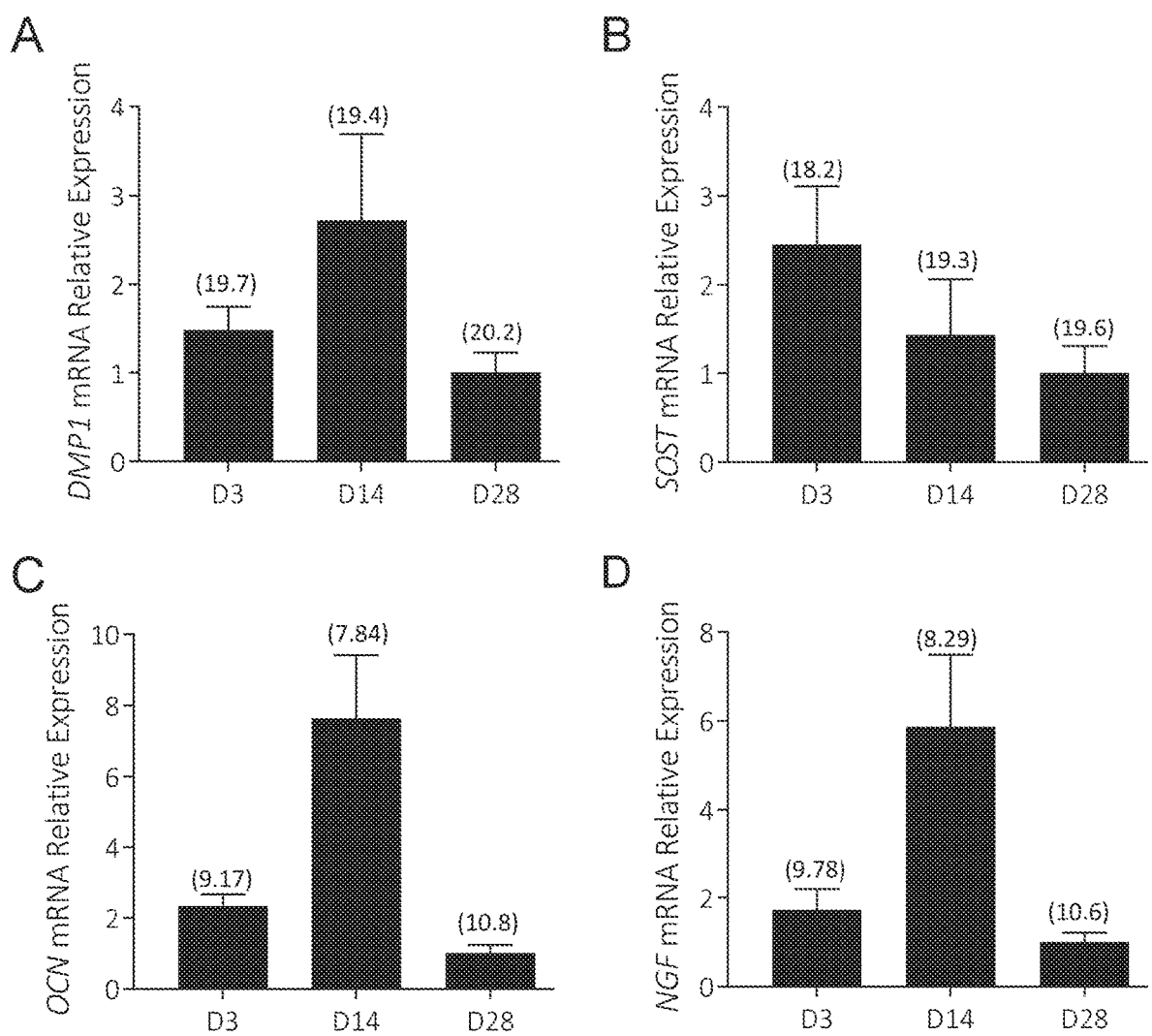

FIG. 25. Human differentiating KOA osteoblast/osteocyte cultures express NGF: Cells from 3 KOA patients were cultured under pro-osteogenic conditions for up to 28d, as described in Materials and Methods. Gene expression was measured by real-time RT-PCR at various timepoints for: A) DMP1; B) SOST; C) OCN; D) NGF. Data (means+standard error of the mean (SEM)) were normalised to the expression of 18S rRNA using the $2^{-(\Delta CT)}$ method and are shown relative to the expression of each gene at the end of the time course pooled from 3 donors' cells. The mean ΔCT for each timepoint is indicated in parentheses above each histogram.

Figure 26:
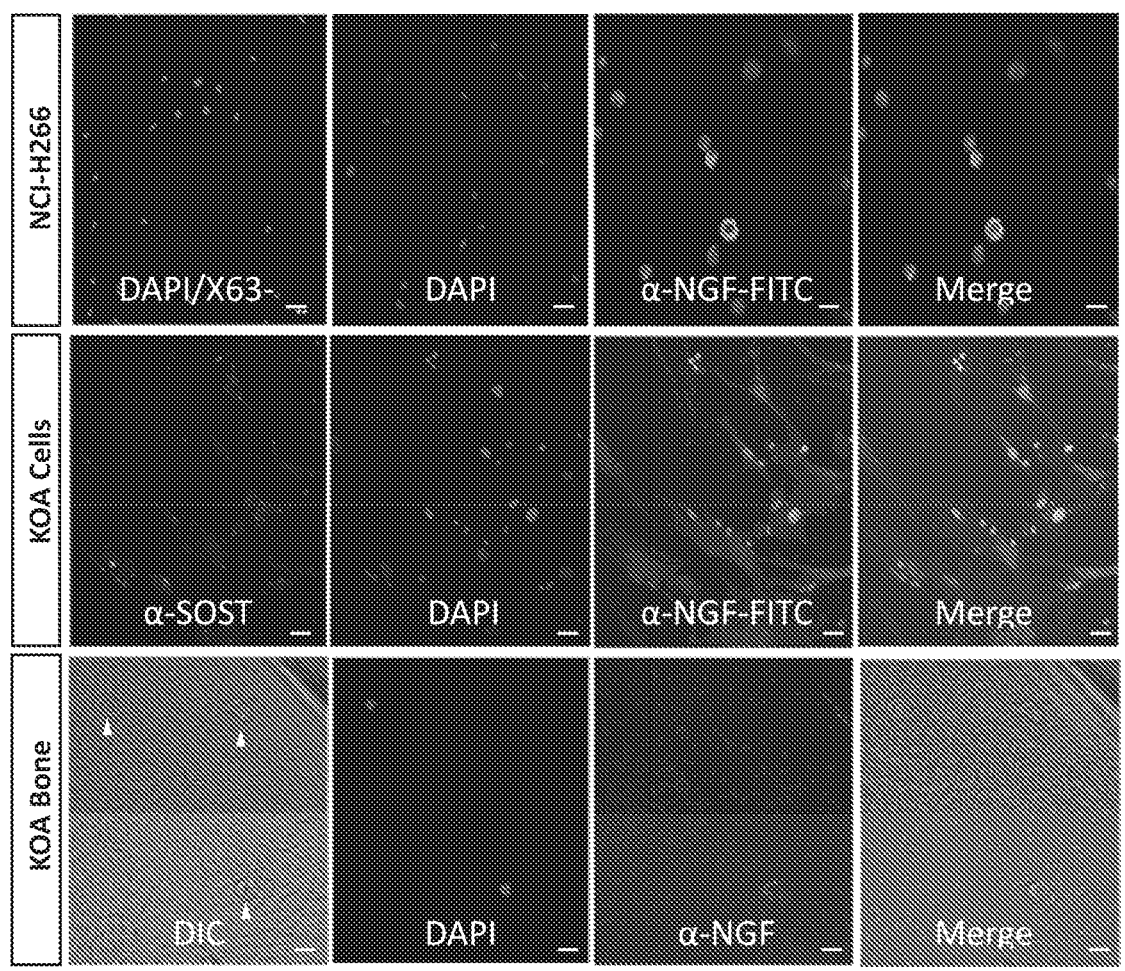

FIG. 26. NGF expression in isolated human osteocytes and in KOA bone. Directly conjugated α-NGF MAb was tested against NCI-H266 cells and compared against a directly conjugated negative control antibody, X-63 (upper row). Fractions IV-VI of a KOA bone digest were similarly stained for NGF, and staining compared against the expression of the osteocyte marker SOST/sclerostin (middle row). Dual staining revealed intracellular but not co-localised staining for both NGF and SOST in these cells. Specificity of staining was confirmed using negative control $IgG_1$ MAb. Finally, NGF positivity was evident in osteocytes (white arrows) in situ in decalcified KOA bone (bottom row), here using unconjugated α-NGF MAb, as described in Materials and Methods. Bone morphology is revealed by digital interference contrast (DIC). In all cases nuclei were visualised by DAPI stain (blue). Scale bars represent 50 µm.

Figure 27:
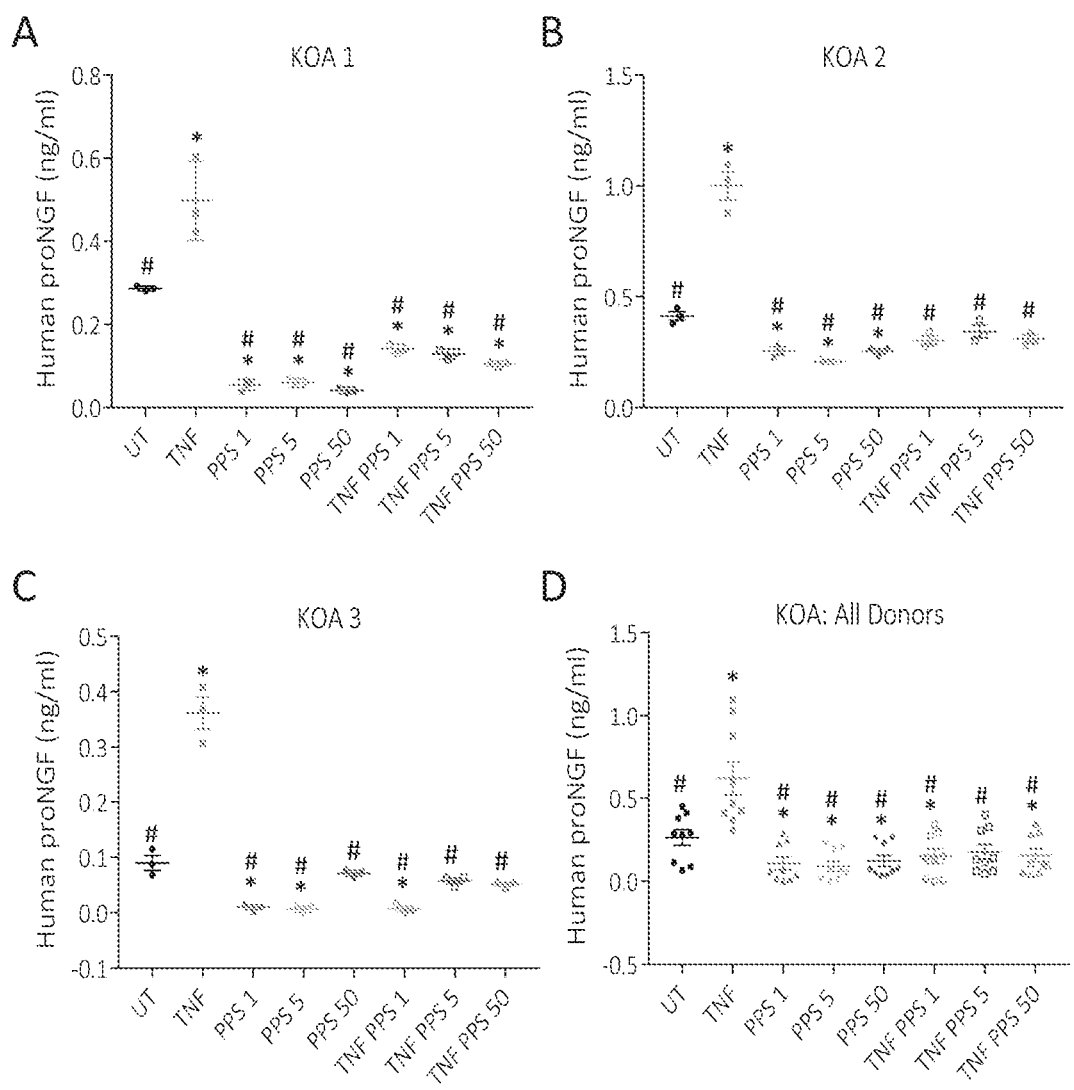

FIG. 27. Human osteocyte-like cells secrete proNGF. Secretion of proNGF was tested from cultures of KOA osteocyte-like cells treated with combinations of rhTNF and PPS. Data are means+SD of supernatants harvested from triplicate wells. Significant difference to untreated control (UT) is indicated by *($p<0.05$); significant difference to rhTNF treated cultures is indicated by #($p<0.05$).

Figure 28:
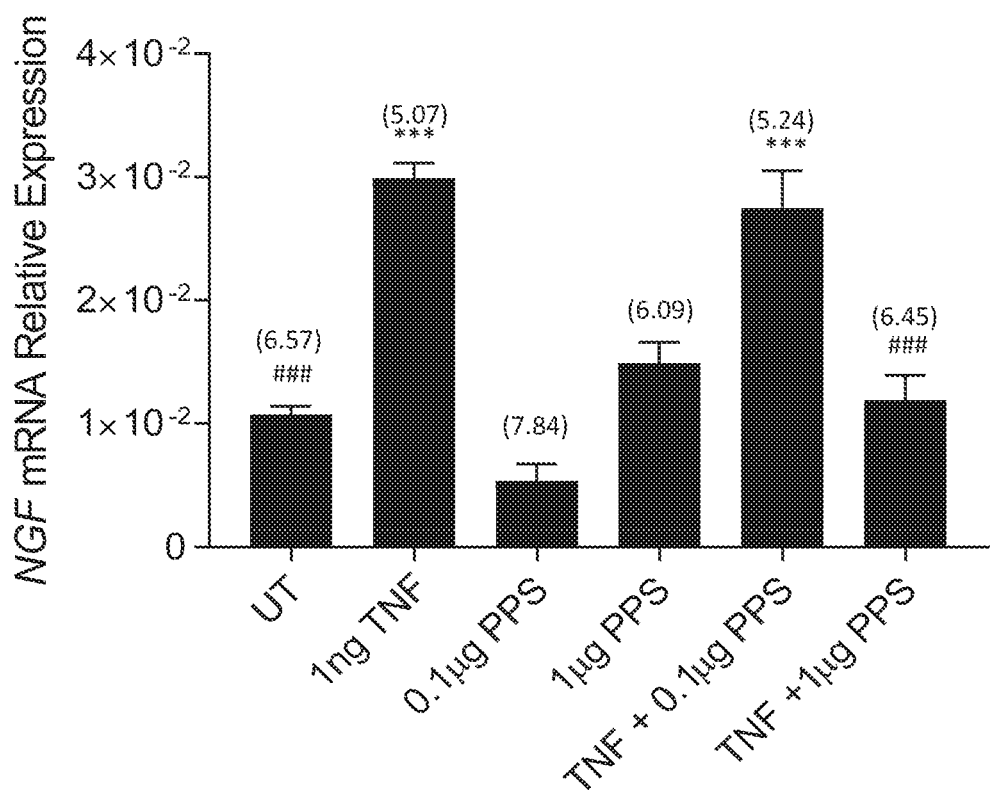

FIG. 28. Effects of combinations of rhTNF and PPS on NGF gene expression in osteocyte-like cultures. Human differentiated osteocyte-like cultures were either untreated or pretreated with PPS (0.1 or 1.0 µg/mL) for 24 h, then with or without rhTNFα (1 ng/mL) for a further 48 h, and then real-time RT-PCR was performed for NGF mRNA. Data are mean+SD of triplicate real-time RT-PCR reactions normalised to the mRNA expression of the housekeeping gene ACTB.

Figure 29:
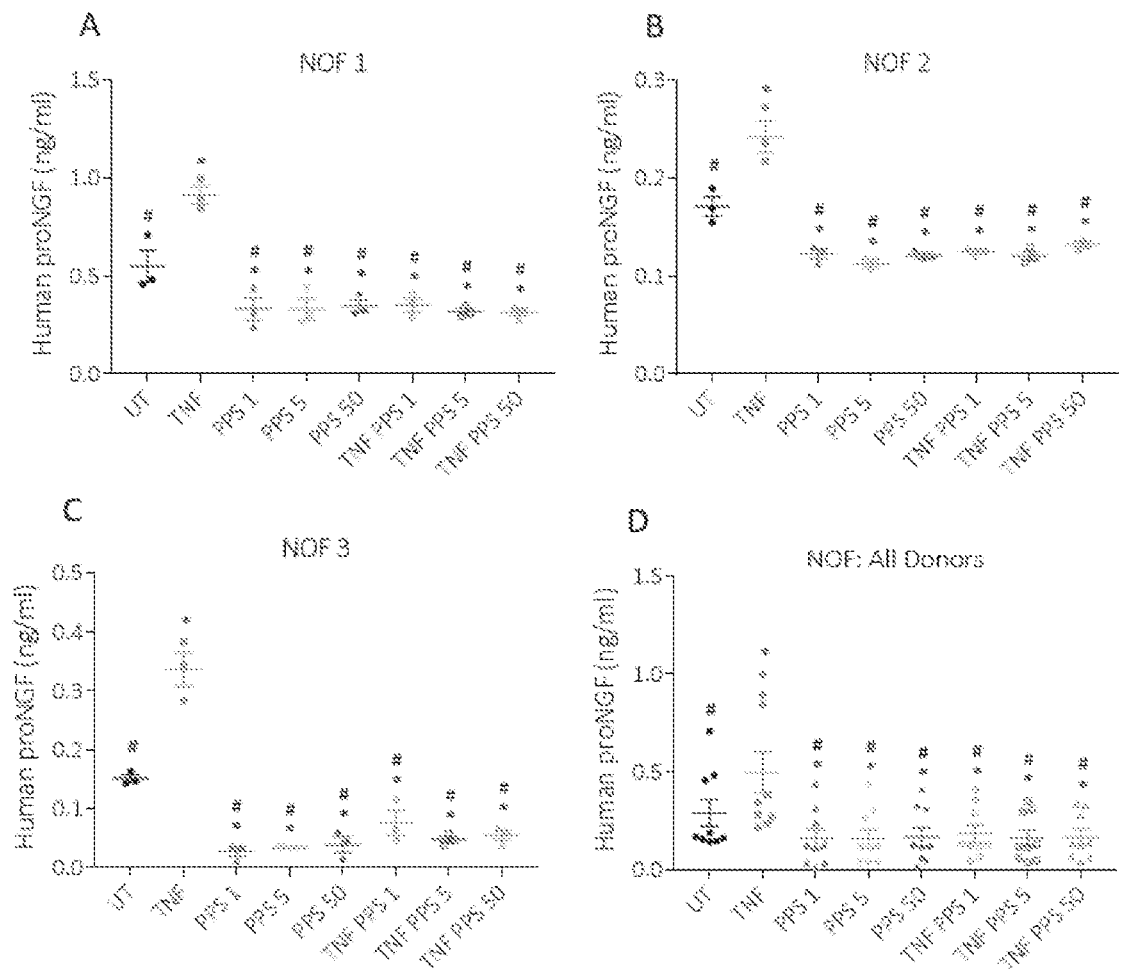

FIG. 29. Human NOF osteocyte-like cells secrete proNGF. Secretion of proNGF was tested from cultures of NOF osteocyte-like cells treated with combinations of rhTNF and PPS. Data are means+SD of supernatants harvested from triplicate wells. Significant difference to untreated control (UT) is indicated by *($p<0.05$); significant difference to rhTNF treated cultures is indicated by #($p<0.05$).

EXAMPLE EMBODIMENTS

1. A method of inhibiting or reducing Nerve Growth Factor (NGF) or pro-Nerve Growth Factor (pro-NGF) activity in a mammal, the method comprising the step of administering a polysulfated polysaccharide or an acceptable salt thereof, to the mammal.

2. The method according to embodiment 1, wherein the inhibiting or reducing of NGF activity treats pain in the mammal.

3. A method of treating pain mediated by Nerve Growth Factor (NGF) or pro-Nerve Growth Factor (pro-NGF), the method comprising the step of administering a polysulfated polysaccharide or an acceptable salt thereof, to a mammal in need of such treatment.

4. The method according to any one of embodiments 1 to 3, wherein the pain is musculoskeletal pain.

5. The method according to embodiment 4, wherein the musculoskeletal pain is non-malignant musculoskeletal pain.

6. The method according to embodiment 4, wherein the musculoskeletal pain is malignant musculoskeletal pain.

7. The method according to embodiment 4, wherein the musculoskeletal pain is skeletal pain.

8. The method according to embodiment 7, wherein the skeletal pain is non-malignant skeletal pain.

9. The method according to embodiment 8, wherein the skeletal pain is malignant skeletal pain.

10. The method according to any one of embodiments 7 to 9, wherein the skeletal pain is back pain.

11. The method according to embodiment 10, wherein the back pain is low back pain.

12. The method according to embodiment 7, wherein the skeletal pain is bone and/or joint pain.

13. The method according to embodiment 12, wherein the skeletal pain is joint pain. 14. The method according to embodiment 12, wherein the skeletal pain is bone pain.

15. The method according to embodiment 14, wherein the bone pain is non-malignant bone pain.

16. The method according to embodiment 15, wherein the non-malignant bone pain is pain associated with osteoporosis.

17. The method according to embodiment 15, wherein the non-malignant bone pain is pain associated with an arthritic condition.

18. The method according to embodiment 17, wherein the arthritic condition is selected from rheumatoid arthritis or osteoarthritis.

19. The method according to embodiment 18, wherein the arthritic condition is rheumatoid arthritis.

20. The method according to embodiment 18, wherein the arthritic condition is osteoarthritis.

21. The method according to embodiment 20, wherein the osteoarthritis is in an articulating joint selected from the group consisting of: an ankle, a hip, knee, shoulder, spine and wrist.

22. The method according to embodiment 21, wherein the osteoarthritis is in the hip.

23. The method according to embodiment 21, wherein the osteoarthritis is in the knee.

24. The method according to embodiment 21, wherein the osteoarthritis is in the spine (spondylosis).

25. The method according to embodiment 14, wherein the bone pain is malignant bone pain.

26. The method according to embodiment 25, wherein the malignant bone pain is pain associated with primary bone cancer.

27. The method according to embodiment 25, wherein the malignant bone pain is pain associated with secondary (metastatic) bone cancer.

28. The method according to any one of embodiments 1 to 3, wherein the pain is associated with a condition selected from the group consisting of: arthritis; osteoarthritis; rheumatoid arthritis; prostatitis; interstitial cystitis; abdominal pain; arthralgia; endometriosis; pancreatitis; chronic headaches; primary cancer; secondary (metastatic) cancer; back pain; bone injury or fracture; diabetic neuropathy; fibromyalgia; migraine; multiple myeloma bone disease; multiple sclerosis; osteoporosis, neuralgia; herpetic neuralgia; postherpetic neuralgia; neoplasm; sciatica; and visceral pain.

29. The method according to embodiment 28, wherein the pain is associated with a condition selected from the group consisting of: arthritis; osteoarthritis; rheumatoid arthritis; prostatitis; and interstitial cystitis.

30. The method according to embodiment 28, wherein the pain is associated with a condition selected from the group consisting of: abdominal pain; arthralgia; endometriosis; pancreatitis; chronic headaches; primary cancer; secondary (metastatic) cancer; back pain; bone injury or fracture; diabetic neuropathy; fibromyalgia; migraine; multiple myeloma bone disease; multiple sclerosis; osteoporosis, neuralgia; herpetic neuralgia; postherpetic neuralgia; neoplasm; sciatica; and visceral pain.

31. The method according to any one of embodiments 1 to 30, wherein the pain is selected from the group consisting of: acute pain; chronic pain; general pain and persistent pain.

32. A composition comprising a polysulfated polysaccharide or an acceptable salt thereof, and an acceptable excipient for inhibiting or reducing Nerve Growth Factor (NGF) or pro-Nerve Growth Factor (pro-NGF) activity in a mammal.

33. A composition comprising a polysulfated polysaccharide or an acceptable salt thereof, and an acceptable excipient for use in inhibiting or reducing Nerve Growth Factor (NGF) or pro-Nerve Growth Factor (pro-NGF) activity in a mammal.

34. The composition according to embodiment 32 or embodiment 33, wherein the inhibiting or reducing treats pain in the mammal.

35. A composition comprising a polysulfated polysaccharide or an acceptable salt thereof, and an acceptable excipient for treating pain mediated by Nerve Growth Factor (NGF) or pro-Nerve Growth Factor (pro-NGF) in a mammal.

36. A composition comprising a polysulfated polysaccharide or an acceptable salt thereof, and an acceptable excipient for use in treating pain mediated by Nerve Growth Factor (NGF) or pro-Nerve Growth Factor (pro-NGF) in a mammal.

37. The composition according to any one of embodiments 32 to 36, wherein the pain is musculoskeletal pain.

38. The composition according to embodiment 37, wherein the musculoskeletal pain is non-malignant musculoskeletal pain.

39. The composition according to embodiment 37, wherein the musculoskeletal pain is malignant musculoskeletal pain.

40. The composition according to embodiment 37, wherein the musculoskeletal pain is skeletal pain.

41. The composition according to embodiment 40, wherein the skeletal pain is non-malignant skeletal pain.

42. The composition according to embodiment 40, wherein the skeletal pain is malignant skeletal pain.

43. The composition according to any one of embodiments 40 to 42, wherein the skeletal pain is back pain.

44. The composition according to embodiment 43, wherein the back pain is low back pain.

45. The composition according to embodiment 40, wherein the skeletal pain is bone and/or joint pain.

46. The composition according to embodiment 45, wherein the skeletal pain is joint pain.

47. The composition according to embodiment 45, wherein the skeletal pain is bone pain.

48. The composition according to embodiment 47, wherein the bone pain is non-malignant bone pain.

49. The composition according to embodiment 48, wherein the non-malignant bone pain is pain associated with osteoporosis.

50. The composition according to embodiment 48, wherein the non-malignant bone pain is pain associated with an arthritic condition.

51. The composition according to embodiment 50, wherein the arthritic condition is selected from rheumatoid arthritis or osteoarthritis.

52. The composition according to embodiment 51, wherein the arthritic condition is rheumatoid arthritis.

53. The composition according to embodiment 51, wherein the arthritic condition is osteoarthritis.

54. The composition according to embodiment 53, wherein the osteoarthritis is in an articulating joint selected from the group consisting of: an ankle, a hip, knee, shoulder, spine and wrist.

55. The composition according to embodiment 54, wherein the osteoarthritis is in the hip.

56. The composition according to embodiment 54, wherein the osteoarthritis is in the knee.

57. The composition according to embodiment 54, wherein the osteoarthritis is in the spine (spondylosis).

58. The composition according to embodiment 47, wherein the bone pain is malignant bone pain.

59. The composition according to embodiment 58, wherein the malignant bone pain is pain associated with primary bone cancer.

60. The composition according to embodiment 58, wherein the malignant bone pain is pain associated with secondary (metastatic) bone cancer.

61. The composition according to any one of embodiments 32 to 36, wherein the pain is associated with a condition selected from the group consisting of: arthritis; osteoarthritis; rheumatoid arthritis; prostatitis; interstitial cystitis; abdominal pain; arthralgia; endometriosis; pancreatitis; chronic headaches; primary cancer; secondary (metastatic) cancer; back pain; bone injury or fracture; diabetic neuropathy; fibromyalgia; migraine; multiple myeloma bone disease; multiple sclerosis; osteoporosis, neuralgia; herpetic neuralgia; postherpetic neuralgia; neoplasm; sciatica; and visceral pain.

62. The composition according to embodiment 61, wherein the pain is associated with a condition selected from the group consisting of: arthritis; osteoarthritis; rheumatoid arthritis; prostatitis; and interstitial cystitis.

63. The composition according to embodiment 61, wherein the pain is associated with a condition selected from the group consisting of: abdominal pain; arthralgia; endometriosis; pancreatitis; chronic headaches; primary cancer; secondary (metastatic) cancer; back pain; bone injury or fracture; diabetic neuropathy; fibromyalgia; migraine; multiple myeloma bone disease; multiple sclerosis; osteoporosis, neuralgia; herpetic neuralgia; postherpetic neuralgia; neoplasm; sciatica; and visceral pain.

64. The composition according to any one of embodiments 32 to 63, wherein the pain is selected from the group consisting of: acute pain; chronic pain; general pain and persistent pain.

65. The composition according to any one of embodiments 32 to 36, wherein the pain is selected from the group consisting of: a nociceptive pain condition; a neuropathic pain condition; an acute pain condition; a chronic pain condition; general pain condition; persistent pain condition; non-malignant pain condition; malignant pain condition; chronic pain condition; general pain condition and persistent pain condition.

66. Use of a polysulfated polysaccharide or an acceptable salt thereof, in inhibiting or reducing Nerve Growth Factor (NGF) or pro-Nerve Growth Factor (pro-NGF) activity in a mammal.

67. Use of a polysulfated polysaccharide or an acceptable salt thereof, in the manufacture of a medicament for inhibiting or reducing Nerve Growth Factor (NGF) or pro-Nerve Growth Factor (pro-NGF) activity in a mammal.

68. The use according to embodiment 66 or embodiment 67, wherein the inhibiting or reducing treats pain in the mammal.

69. Use of a polysulfated polysaccharide or an acceptable salt thereof, in treating pain mediated by Nerve Growth Factor (NGF) or pro-Nerve Growth Factor (pro-NGF) in a mammal.

70. Use of a polysulfated polysaccharide or an acceptable salt thereof, in the manufacture of a medicament for treating pain mediated by Nerve Growth Factor (NGF) or pro-Nerve Growth Factor (pro-NGF) in a mammal.

71. The use according to any one of embodiments 66 to 70, wherein the pain is musculoskeletal pain.

72. The use according to embodiment 71, wherein the musculoskeletal pain is non-malignant musculoskeletal pain.

73. The use according to embodiment 71, wherein the musculoskeletal pain is malignant musculoskeletal pain.

74. The use according to embodiment 71, wherein the musculoskeletal pain is skeletal pain.

75. The use according to embodiment 74, wherein the skeletal pain is non-malignant skeletal pain.

76. The use according to embodiment 74, wherein the skeletal pain is malignant skeletal pain.

77. The use according to any one of embodiments 74 to 76, wherein the skeletal pain is back pain.

78. The use according to embodiment 77, wherein the back pain is low back pain.

79. The use according to embodiment 74, wherein the skeletal pain is bone and/or joint pain.

80. The use according to embodiment 79, wherein the skeletal pain is joint pain.

81. The use according to embodiment 79, wherein the skeletal pain is bone pain.

82. The use according to embodiment 81, wherein the bone pain is non-malignant bone pain.

83. The use according to embodiment 82, wherein the non-malignant bone pain is pain associated with osteoporosis.

84. The use according to embodiment 82, wherein the non-malignant bone pain is pain associated with an arthritic condition.

85. The use according to embodiment 84, wherein the arthritic condition is selected from rheumatoid arthritis or osteoarthritis.

86. The use according to embodiment 85, wherein the arthritic condition is rheumatoid arthritis.

87. The use according to embodiment 85, wherein the arthritic condition is osteoarthritis.

88. The use according to embodiment 87, wherein the osteoarthritis is in an articulating joint selected from the group consisting of: an ankle, a hip, knee, shoulder, spine and wrist.

89. The use according to embodiment 88, wherein the osteoarthritis is in the hip.

90. The use according to embodiment 88, wherein the osteoarthritis is in the knee.

91. The use according to embodiment 88, wherein the osteoarthritis is in the spine (spondylosis).

92. The use according to embodiment 81, wherein the bone pain is malignant bone pain.

93. The use according to embodiment 92, wherein the malignant bone pain is pain associated with primary bone cancer.

94. The use according to embodiment 92, wherein the malignant bone pain is pain associated with secondary (metastatic) bone cancer.

95. The use according to any one of embodiments 66 to 70, wherein the pain is associated with a condition selected from the group consisting of: arthritis; osteoarthritis; rheumatoid arthritis; prostatitis; interstitial cystitis; abdominal pain; arthralgia; endometriosis; pancreatitis; chronic headaches; primary cancer; secondary (metastatic) cancer; back pain; bone injury or fracture; diabetic neuropathy; fibromyalgia; migraine; multiple myeloma bone disease; multiple sclerosis; osteoporosis, neuralgia; herpetic neuralgia; postherpetic neuralgia; neoplasm; sciatica; and visceral pain.

96. The use according to embodiment 95, wherein the pain is associated with a condition selected from the group consisting of: arthritis; osteoarthritis; rheumatoid arthritis; prostatitis; and interstitial cystitis.

97. The use according to embodiment 95, wherein the pain is associated with a condition selected from the group consisting of: abdominal pain; arthralgia; endometriosis; pancreatitis; chronic headaches; primary cancer; secondary (metastatic) cancer; back pain; bone injury or fracture; diabetic neuropathy; fibromyalgia; migraine; multiple myeloma bone disease; multiple sclerosis; osteoporosis, neuralgia; herpetic neuralgia; postherpetic neuralgia; neoplasm; sciatica; and visceral pain.

98. The use according to any one of embodiments 66 to 97, wherein the pain is selected from the group consisting of: acute pain; chronic pain; general pain and persistent pain.

99. The the use according to any one of embodiments 66 to 70, wherein the pain is selected from the group consisting of: a nociceptive pain condition; a neuropathic pain condition; an acute pain condition; a chronic pain condition; general pain condition; persistent pain condition; non-malignant pain condition; malignant pain condition; chronic pain condition; general pain condition and persistent pain condition.

100. A method, a composition or a use according to any one of embodiments 1 to 99, wherein the polysulfated polysaccharide is selected from the group consisting of high molecular weight heparin, low molecular weight heparins, the heparan sulfates, pentosan polysulfate, chondroitin polysulfate, chitosan polysulfate, dermatan polysulfate sulodexide, dextran sulfate, polysulfated inulin, sulfated lactobionic acid amide, sulfated bis-aldonic acid amide, sucrose octasulfate, fucoidan-1, fucoidan-2, sulfated beta-cyclodextrin, sulfated gamma-cyclodextrin and small sulfated compounds including, but are not limited to, inositol hexasulfate.

101. The method, the composition or the use according to embodiment 100, wherein the polysulfated polysaccharide is selected from the group consisting of high molecular weight heparin, low molecular weight heparins, pentosan polysulfate (PPS), chondroitin polysulfate and chitosan polysulfate.

102. The method, the composition or the use according to embodiment 101, wherein the pentosan polysulfate (PPS) is selected from the group consisting of: the sodium salt of pentosan polysulfate (NaPPS), the magnesium salt of pentosan polysulfate (MgPPS), the calcium salt of pentosan polysulfate (CaPPS), and the zinc salt of pentosan polysulfate (ZnPPS).

103. The method, the composition or the use according to embodiment 102, wherein the pentosan polysulfate (PPS) is sodium pentosan polysulfate (NaPPS).

104. The method, the composition or the use according to any one of embodiments 1 to 103, wherein the inhibiting or reducing, or treating is by administering through an intraventricular route, intracisternal route or intrathecal route, an injection by the intra-muscular (IM) or sub-cutaneous (SC) routes, intra-venously (IV), intra-articularly (IA), peri-articularly, topically, via suppositories or orally.

105. The method, the composition or the use according to any one of embodiments 1 to 104, wherein the inhibiting or reducing, or treating is by administering the polysulfated polysaccharide or the acceptable salt thereof to the mammal in an effective amount of about 1 to 2 mg/kg of the mammal per dose.

106. The method, the composition or the use according to any one of embodiments 1 to 105, wherein the inhibiting or reducing, or treating is by administering the polysulfated polysaccharide or the acceptable salt thereof to the mammal in an effective amount of about 2 mg/kg of the mammal per dose.

107. The method, the composition or the use according to any one of embodiments 104 to 106, wherein the administering is by an injection.

108. The method, the composition or the use according to embodiment 107, wherein the administering is by sub-cutaneous (SC) injection.

109. The method, the composition or the use according to embodiment 108, wherein the SC injection is slow SC injection.

110. The method, the composition or the use according to any one of embodiments 104 to 109, wherein administration to a human is by dosing in a treatment regimen once daily, twice weekly or thrice weekly.

111. The method, the composition or the use according to embodiment 110, wherein administration to a human is by dosing in a treatment regimen twice weekly.

112. The method, the composition or the use according to embodiment 111, wherein administration to a human is by dosing in a treatment regimen twice weekly with a minimum of three days and a maximum of four days between dosages.

113. The method, the composition or the use according to embodiment 111 or embodiment 112, wherein administration to a human is by dosing in a treatment regimen twice weekly for six weeks.

114. The method, the composition or the use according to embodiment 113, wherein the total dose of polysulfated polysaccharide administered in the treatment regimen is about 200 to 4000 mg.

115. The method, the composition or the use according to any one of embodiments 1 to 113, wherein the inhibiting or reducing, or treating is by administering the polysulfated polysaccharide or the acceptable salt thereof to the mammal in an effective amount in the range of about 10 ng to about 1000 ng as a fixed dose.

116. The method, the composition or the use according to embodiment 1 to 113, wherein the inhibiting or reducing, or treating is by administering the polysulfated polysaccharide or the acceptable salt thereof to the mammal in an effective amount in the range of about 1014 to about 1000 jig as a fixed dose.

117. The method, the composition or the use according to embodiment 115 or embodiment 116, wherein the inhibiting or reducing, or treating is by administering the polysulfated polysaccharide or the acceptable salt thereof by an intraventricular, intracisternal or intrathecal route.

118. The method, the composition or the use according to any one of embodiments 104 to 113, wherein the inhibiting or reducing, or treating is by administering the polysulfated polysaccharide or the acceptable salt thereof to the mammal in an effective amount in the range of about 1 mg to about 25 mg as a fixed dose.

119. The method, the composition or the use according to any one of embodiments 1 to 118, wherein pain in the mammal is reduced after administration.

120. The method, the composition or the use according to embodiment 119, wherein pain in the mammal is reduced as determined by a rating scale.

121. The method, the composition or the use according to embodiment 120, wherein the rating scale is the numerical rating scale (NRS).

122. The method, the composition or the use according to any one of embodiments 1 to 121, wherein administration of the polysulfated polysaccharide or the acceptable salt thereof further maintains or improves mammal health.

123. The method, the composition or the use according to any one of embodiments 1 to 122, wherein administration of the polysulfated polysaccharide or the acceptable salt thereof further maintains mammal body weight.

124. The method, the composition or the use according to any one of embodiments 1 to 123, wherein administration of the polysulfated polysaccharide or the acceptable salt thereof further maintains or improves musculoskeletal integrity and/or function.

125. The method, the composition or the use according to embodiment 124, wherein administration of the polysulfated polysaccharide or the acceptable salt thereof further maintains or improves skeletal integrity and/or function.

126. The method, the composition or the use according to embodiment 125, wherein administration of the polysulfated polysaccharide or the acceptable salt thereof further maintains or improves the integrity and/or function of a joint or a bone.

127. The method, the composition or the use according to embodiment 126, wherein administration of the polysulfated polysaccharide or the acceptable salt thereof further maintains or improves the integrity and/or function of bone.

128. The method, the composition or the use according to any one of embodiments 1 to 127, wherein administration of the polysulfated polysaccharide or the acceptable salt thereof prevents cancer-induced bone fracture, wherein the mammal is suffering from bone cancer.

129. The method, the composition or the use according to embodiment 128, wherein administration of the polysulfated polysaccharide or the acceptable salt thereof delays the time to cancer-induced bone fracture, wherein the mammal is suffering from bone cancer.

130. The method, the composition or the use according to any ine of embodiments 1 to 127, wherein administration of the polysulfated polysaccharide or the acceptable salt thereof prevents or ameliorates bone loss.

131. The method, the composition or the use according to any one of embodiments 1 to 130, wherein administration of the polysulfated polysaccharide or the acceptable salt thereof prevents or ameliorates dysregulation of mineral homeostasis.

132. The method, the composition or the use according to embodiment 131, wherein the mineral homeostasis is calcium and/or phosphate homeostasis.

133. The method, the composition or the use according to any one of embodiments 1 to 132, wherein administration of the polysulfated polysaccharide or the acceptable salt thereof prevents or ameliorates nerve compression syndromes.

134. The method, the composition or the use according to any one of embodiments 1 to 133, wherein function in the mammal is improved after administration.

135. The method, the composition or the use according to embodiment 134, wherein the function in the mammal is improved as determined by the Lysholm Knee Score described herein.

Examples

Example Study 1: Effect of Sodium Pentosan Polysulfate (NaPPS) on the Human Osteocyte Response to Inflammatory Mediators A preliminary study to examine the possibility that PPS exerts an effect on pain mediators is described. The study also looks at the possibility that PPS exerts an effect on pain mediators through the osteocyte.

Introduction to Study

Osteoarthritis of the Knee (KOA) is a common and painful condition, which is primarily managed by the prescription of analgesics to control pain. The aetiology of KOA is incompletely understood but is known to be associated with the increased expression of proinflammatory mediators, including tumour necrosis factor alpha (TNFα) and interleukin 1-beta (IL-1β) [21]. These are thought to stimulate the localised production of cartilage-degrading enzymes, such as matrix metallopeptidase (MMP) family member-13 (MMP-13). Ultimately, total knee arthroplasty (TKA) is performed to replace the diseased joint with a prosthetic total knee replacement. Patient reported pain is the major indicator for TKA [22].

Bone is an innervated tissue, with bone sensory neurons deriving solely from the dorsal root ganglion of the spinal cord [23]. The secreted neurotropic protein beta-Nerve Growth Factor (NGF) is a major contributor to pain in a number of chronic conditions, including KOA [24-26]. Furthermore, NGF expression is known to be induced by both TNFα and IL-1β in an experimental mouse model of osteoarthritis [27]. NGF binds to at least two receptors expressed by neurons, tropomyosin receptor kinase A (TrkA) and the pan-neurotropin receptor p75/NTR, where it can have diverse biological effects, either promoting neuronal growth or causing neuron apoptosis, depending on whether the neuron also expresses the co-receptor, sortilin [28]. A neutralising antibody treatment that targets NGF, Tanezumab®, has yielded promising results in the treatment of pain associated with KOA [21, 24-26], consistent with NGF being both a key readout and a mediator of pain for this condition. NGF is first translated as a pro-protein form (proNGF), which is post-translationally processed (proteolytically cleaved) to the mature form by the action of furin or furin-like pro-protein convertases [28]. Currently, the accurate detection of soluble NGF levels using commercially available enzyme linked immunosorbent assays (ELISAs) is problematic due to the influence on readouts of proNGF; if present, proNGF interferes with the readouts of a number of commercially available ELISA kits in an unpredictable fashion, in terms of both the magnitude and the direction (increase or decrease) of the effect [29]. It is therefore necessary to defer quantative assessment to the levels of proNGF.

Pentosan Polysulfate (PPS) Sodium is an FDA-approved drug for the treatment of interstitial cystitis and bladder pain syndrome, with an excellent safety profile [30]. It is currently being tested for its efficacy as a treatment for KOA with promising results [31]. The mode of action of PPS appears to be multi-factorial, and includes replenishment of the glycosaminoglycan (GAG) layer in the case of its effect in interstitial cystitis, as well as effects on intracellular signalling, in particular the nuclear factor kappa-B (NFκB) [32], and the IL-1β-iNOS [33] pathways in chondrocytes. Importantly, KOA is a disease of the entire joint, with changes to the sub-chondral bone, as well as to the synovium and cartilage [21]. The contribution of each tissue to disease progression and to the associated pain is incompletely understood. In advanced KOA, there is nearly complete degradation of the cartilage with a paucity of healthy chondrocytes remaining. This suggests that mediators of pain may derive to a significant extent from the underlying sub-chondral bone. The most numerous cell type in hard bone tissue is the osteocyte, and these cells are increasingly recognised as the key controlling cell type in many local and systemic physiological processes [34, 35]. In conditions associated with osteoarthritis, the osteocyte is involved in the inflammatory, osteolytic response to implant-derived wear particles [36] and also elicits impressive pro-inflammatory responses to bacteria in the condition of periprosthetic joint infection [37].

Study Hypotheses

We hypothesised that osteocytes are capable of producing NGF in the inflammatory milieu of the subchondral bone in KOA and that PPS may act by inhibiting this production.

To test this hypothesis, we examined the effects of PPS on the responses of human primary osteocyte-like cultures, differentiated from the proximal tibiae of patients suffering from advanced KOA and undergoing TKA. Treatment with recombinant TNFα was used as the proinflammatory stimulus, and the effects on the relative expression of a number of genes, including NGF was examined. NGF and proNGF protein levels were also measured by respective ELISAs.

We show, for the first time that human osteocytes are capable of producing NGF, suggesting that they potentially contribute to localised pain responses. We also show that PPS suppresses NGF mRNA transcription and proNGF secretion by osteocytes and reverses the stimulatory effects of TNFα on these processes. Together, our findings suggest a hitherto unknown role for osteocytes in the pain response and a mechanism for the pain benefit in KOA patients taking PPS.

Materials and Methods

Ethical Statement

All studies with human patient derived material were covered by pre-existing ethics committee approval by the Human Research Ethics Committee of the Royal Adelaide Hospital (Approval No. 130114). All donor material was obtained with written informed patient consent.

Study Design
Donors and Cells

In order to maximise the clinical relevance of the findings from this study, the effects of PPS were to be tested on osteocyte-like cultures [36, 38-42] derived by differentiation in vitro for a period of 28 days from cells isolated from the subchondral bone of the proximal tibia of three patients with advanced knee OA who underwent total knee arthroplasty (TKA) surgery (KOA: Group 1). As a comparator group, cells isolated from the proximal femur of three patients who underwent total hip arthroplasty (THA) for neck of femur fracture (NOF: Group 2), were similarly differentiated and tested. The gender of all donors was female, and group were age matched, with the mean age of KOA being 77.0±8.5 years and that of the NOF group being 77.7±5.5 years (p=0.91).

Cryopreserved cells from each donor (all at passage 0 or 1) were thawed and cultured for 10d in T75 cm² tissue culture flasks. Once confluent, cells were removed by collagenase/dispase digestion, washed by centrifugation, counted and adjusted to $5\times10^5$ cells/mL. Cells were then seeded into either 12-well tissue culture trays or into 8-well chamber slides, at $1\times10^5$ and $2\times10^4$ cells/well, respectively. After 24 h, media were replaced with osteogenic differentiation medium, consisting of αMEM, 5% v/v foetal calf serum (FCS), 1.8 mM potassium dihydrogen phosphate ($KH_2PO_4$), 100 µM Ascorbate-2-phosphate (As2P), 10 mM HEPES, $10^{-8}$ M Dexamethasone and 0.2 mM L-Glutamine. During the differentiation process, samples were collected at days 3, 14 and 28 in Trizol reagent for total RNA preparation and gene expression analysis (see below). Cultures seeded into chamber slides were examined for in vitro mineralisation using the Alizarin Red staining technique, as previously described [41].

PPS and TNFα Treatment

PPS was manufactured by bene pharmaChem GmbH & Co. KG, Geretstried, Germany. This was dissolved in sterile PBS as a stock solution at 1.0 mg/mL. Differentiated cells were either untreated or pre-treated with final concentrations of PPS at 1, 5 or 50 µg/mL in culture medium for 72 h. The tested doses of PPS were based on the effective and maximally active levels published in a previous study [43]. Media were then replaced with the same concentrations of PPS with or without the addition of recombinant human (rh) TNFα (1 ng/mL) and then cultured for a further 48 h. Culture supernatants were collected and total RNA and cDNA prepared, as described below. This generated 8 conditions (Untreated, TNF, PPS1, PPS5, PPS50, TNF+PPS1, TNF+PPS5, TNF+PPS50) from 6 donors.

Total RNA Production and Real-Time RT-PCR Analysis

Total RNA was prepared from Trizol lysates, according to the manufacturer's instructions, with the exception that due to evidence for PPS interference in the generation of assayable cDNA, RNA precipitates were washed 3 times in 75% ethanol instead of the usual single wash step, in an attempt to remove residual PPS. RNA preparations were tested for yield and purity using a Nanodrop microvolume spectrophotometer (Thermo Fisher). One microgram of RNA from each sample was reverse transcribed using a Superscript™ II kit (Thermo Fisher), as per manufacturer's instructions. Real-time RT-PCR was performed for genes including Nerve Growth Factor (NGF), its receptors NTRK1 (TRKA) and NGFR (P75NTR), MMP13, Cyclooxygenase-2 (COX-2), Interleukin-6 (IL-6) RANKL, OPG, OCN, DMP1 and SOST, relative to housekeeping gene (18S, ACTB) expression. Oligonucleotide primer sequences for each of these are shown in Table 1.

TABLE 1

Human mRNA-specific oligonucleotide primer sequences.

| Gene | Forward Primer Sequence | Reverse Primer Sequence |
| --- | --- | --- |
| 18S [36]* | 5'-ggaattcccgagtaagtgcg-3' (SEQ ID NO: 1) | 5'-gcctcactaaaccatccaa-3' (SEQ ID NO: 2) |
| Beta Actin [36] | 5'-cgcgagaagatgacccagatc-3' (SEQ ID NO: 3) | 5'-tcaccggagtccatcacg-3' (SEQ ID NO: 4) |
| COX-2 | 5'-ggagaaaactgctcaacaccg-3' (SEQ ID NO: 5) | 5'-tattcacaacgttccaaaatccc-3' (SEQ ID NO: 6) |
| DMP1 [36] | 5'-gatcagcatcctgctcatgtt-3' (SEQ ID NO: 7) | 5'-agccaaatgacccttccattc-3' (SEQ ID NO: 8) |
| IL-6 | 5'-tcagccctgagaaaggagac-3' (SEQ ID NO: 9) | 5'-tctcctcattgaatccagattg-3' (SEQ ID NO: 10) |
| MMP13 [36] | 5'-ggatccagtctctctatggt-3' (SEQ ID NO: 11) | 5'-ggcatcaagggataaggaag-3' (SEQ ID NO: 12) |
| NGF [44] | 5'-cacactgaggtgcatagcgt-3' (SEQ ID NO: 13) | 5'-tgatgaccgcttgctcctgt-3' (SEQ ID NO: 14) |
| NGFR/TRKA [45] | 5'-cctggacagcgtgacgttc-3' (SEQ ID NO: 15) | 5'-cccagtcgtctcatcctggt-3' (SEQ ID NO: 16) |
| P75NTR [45] | 5'-cctggacagcgtgacgttc-3' (SEQ ID NO: 17) | 5'-cccagtcgtctcatcctggt-3' (SEQ ID NO: 18) |
| OCN [36] | 5'-atgagagccctcacactcctcg-3' (SEQ ID NO: 19) | 5'-gtcagccaactcgtcacagtcc-3' (SEQ ID NO: 20) |
| OPG [36] | 5'-gctcacaagaacagactttccag-3' (SEQ ID NO: 21) | 5'-ctgttttcacagaggtcaatatctt-3' (SEQ ID NO: 22) |

TABLE 1-continued

Human mRNA-specific oligonucleotide primer sequences.

| Gene | Forward Primer Sequence | Reverse Primer Sequence |
| --- | --- | --- |
| RANKL [36] | 5'-ccaagatctccaacatgact-3' (SEQ ID NO: 23) | 5'-tacaccattagttgaagatact-3' (SEQ ID NO: 24) |
| SOST [36] | 5'-accggagctggagaacaaca-3' (SEQ ID NO: 25) | 5'-gctgtactcggacacgtctt-3' (SEQ ID NO: 26) |

*Published references to primer pairs are indicated next to gene names; all primer pairs were designed and/or validated in-house.

ELISA Analysis

Figure 1:
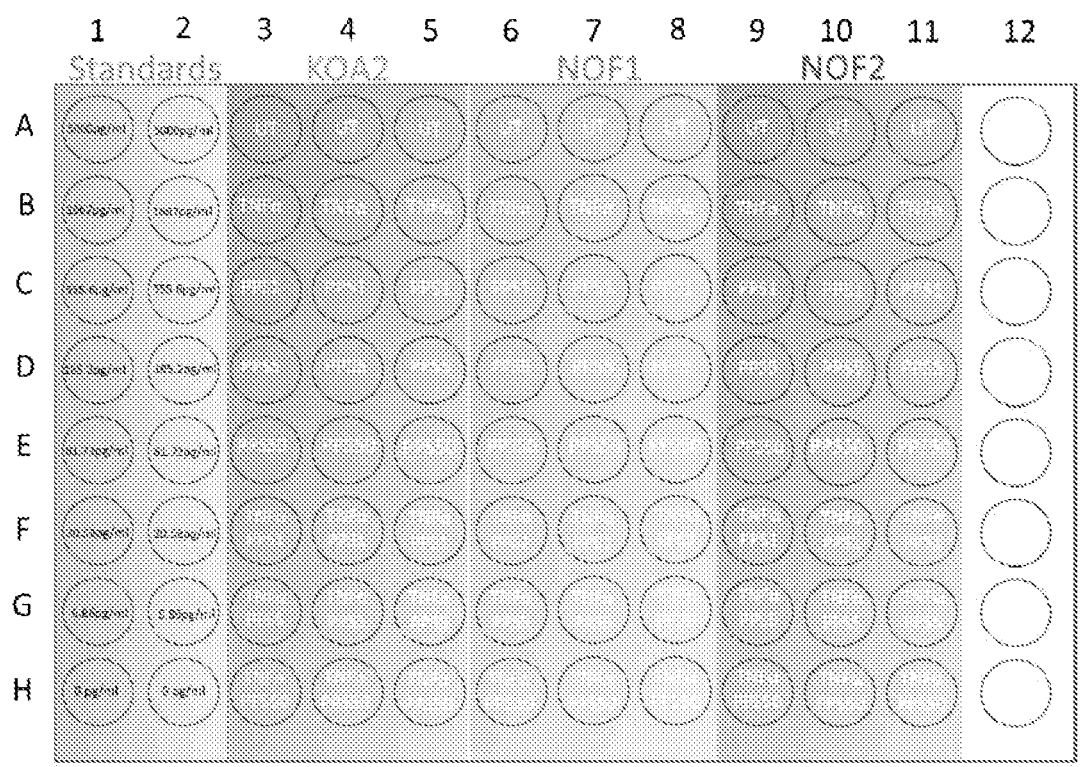
FIG. 1. An example of an NGF/proNGF ELISA plate layout.

Culture supernatants, which were stored frozen (−80° C.) until use, whereupon they were thawed at 4° C., and assayed by ELISA for human NGF (Cat. No: EHNGF; Thermo Fisher Scientific) or proNGF (Cat. No: BEK-2226-2P; Biosensis) protein levels, as per the manufacturers' instructions. A schematic of the general plate layout is shown in FIG. 1.

Immunostaining

Cell seeded in 8-well chamber slides and differentiated for 28 days or freshly digested from bone were either untreated or treated with rhTNFα (1 ng/mL), PPS (50 µg/mL; 'PPS50') or PPS50+rhTNFα. Following differentiation, medium was removed and all wells rinsed with PBS (pH 7.4, Gibco) a total of three times. Cells were then fixed with 100 µL of Histochoice (Sigma-Aldrich) tissue fixative for 1 hour at room temperature. After fixation, wells were rinsed twice with distilled H2O and stored at 4° C. until staining. Cells were blocked with 50 µL of blocking buffer (5% v/v normal rabbit serum in 1×PBS) for 20 minutes at room temperature in a humid chamber. Cells were then rinsed with wash buffer (0.1% v/v normal rabbit serum in PBS) three times. Cells were stained with either mouse monoclonal IgG1 anti-human NGF (25623; Thermo Fisher Scientific), anti-human NGFR (2F1C2; Thermo Fisher Scientific), or anti-human TrkA (6B2; Thermo Fisher Scientific), or anti-human SOST (MAb 220902.11; R&D Systems, Minneapolis, MN, USA) primary antibodies and their respective IgG1 isotype controls (MAb 1B5). Primary antibodies and IgG control were diluted between 1:50 and 1:400. Cells were incubated with primary antibody for 40 minutes at 4° C. For unconjugated MAbs, chamber slides were then rinsed 3× with wash buffer and 50 µL of rabbit α-mouse Alexa-fluor secondary antibody (1:2000 dilution), also containing nuclear DAPI stain (1:2000 dilution; diamidino-2-phenylindole; Thermo Fisher) was added to the wells. Following a 1 hour incubation at room temperature, secondary antibody was removed and the wells were washed three times with wash buffer. Finally, FluoroBrite DMEM (Life Technologies) was added to each well to image using confocal microscopy (FV3000 Confocal Microscope, Olympus Lifescience; Adelaide Microscopy).

For double-labelling purposes, anti-NGF was directly conjugated to fluorescein isothiocyanate (FITC; Sigma Chemical Co., St. Louis, MO, USA). For this MAb 25623 was first dialysed against carbonate/bicarbonate buffer (1 L; pH 9.6) at 4° C. overnight. FITC was dissolved to 1 mg/mL in anhydrous DMSO. 15 µL, FITC solution was added to 100 µg anti-NGF and the tube mixed on a rotator for 2 h at room temperature. Unbound FITC was removed using size-exclusion chromatography on a Sephadex G-column (Pharmacia Biotech, Piscataway, NJ, USA). The absorbance of 0.5 mL fractions at 280 nm and 492 nm was determined using a NanoDrop One spectrophotometer (Thermo Fisher Scientific) and the concentration of FITC-conjugated antibody determined by the formula: concentration (mg/mL)=$A_{280}$−($A_{492}$×0.35)/1.4. To remove aggregates, the antibody solution was centrifuged at 16,400 RCF for 15 minutes prior to use. As a positive control for immunostaining, the small cell lung carcinoma cell line NCI-H266 (ATCC, Masassas, VA, USA) was identified to be NGF-expressing using the Harmonizome database [Rouillard A D, Gundersen G W, Fernandez N F, Wang Z, Monteiro C D, McDermott M G, Ma'ayan A]. For these assays, FITC-conjugated X-63 MAb (Biosensis, Thebarton, SA, Australia) was used as a negative control; direct conjugates were incubated for 40 min, aspirated and the wells washed three times, as above.

Bone isolated from KOA patients was fixed, decalcified, embedded and sectioned, as described [37]. Bone sections (5 µm) were first heated at 60° C. for 15 min to melt excess paraffin and then dewaxed. For antigen retrieval, slides were then incubated in 10% formic acid in distilled water for 10 min, rinsed in PBS and then immunostained, as above.

Human Primary Osteocyte Isolation from Fresh Bone

For some experiments, freshly obtained human patient bone was used as a source of primary osteocytes, as described [46], for the purpose of immunostaining.

Data and Statistical Analysis:

ELISA data were inputted into GraphPad Prism software (GraphPad Prism, La Jolla, CA, USA) and analysed by two-way analysis of variance (ANOVA), with Holm-Sidak's multiple comparison post-hoc tests. Values for $p<0.05$ were considered statistically significant.

Results and Discussion

NGF Expression by Cultured Osteocytes

Figure 2:
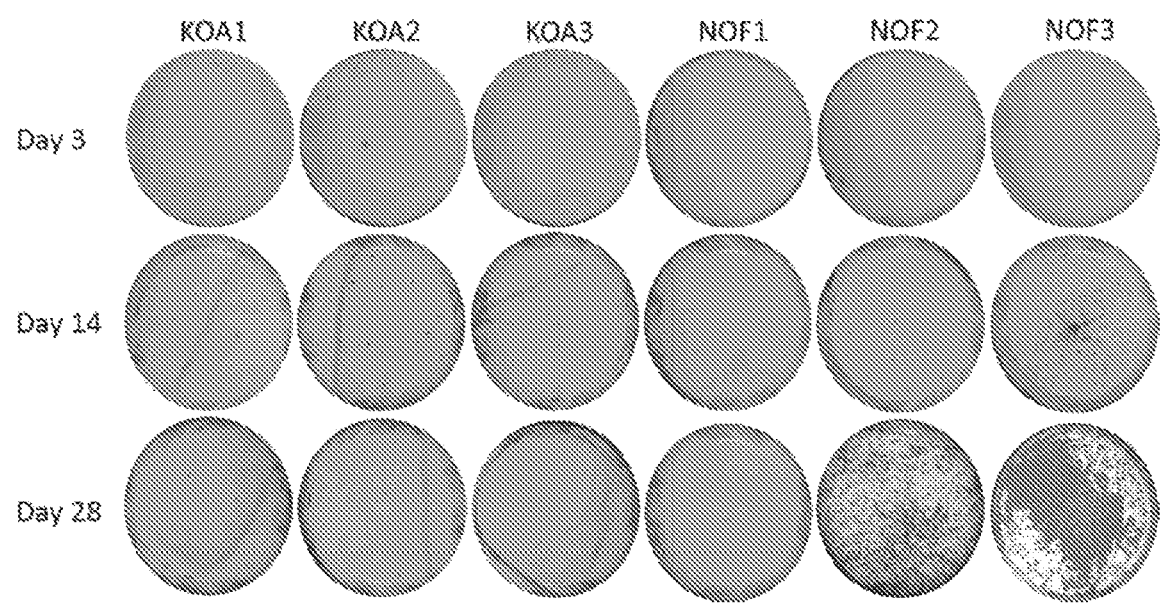
FIG. 2. Representative Alizarin Red stains of differentiating KOA and NOF osteoblast/osteocyte-like cultures.
Figure 3:
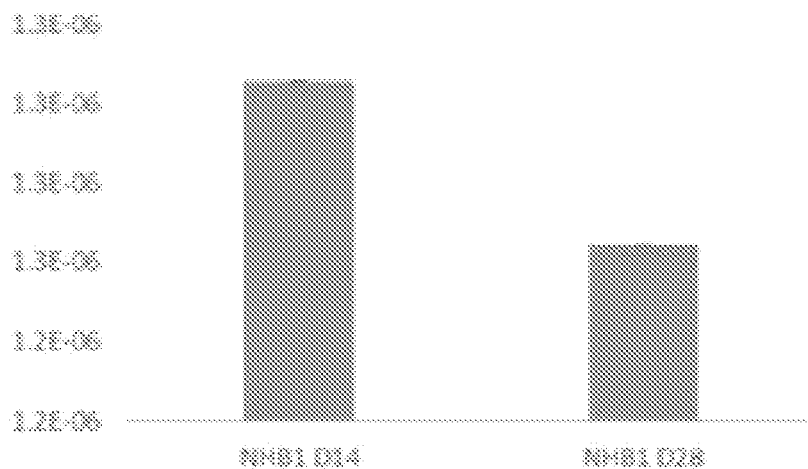
FIG. 3. Gene expression of osteoblast/osteocyte differentiation markers in KOA cultures from three donors (KOA1-3): DMP1. A) KOA1-DMP1:18S mRNA expression; B) KOA2-DMP1:18S mRNA expression; and C) KOA3-DMP1 mRNA expression. Data are triplicate real-time RT-PCR reactions (mean+standard deviation (SD)) relative to the expression of 18S rRNA.
Figure 3:
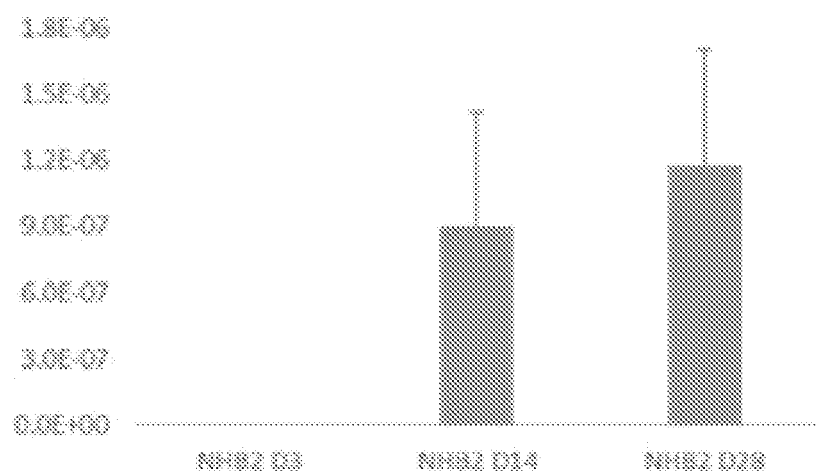
Figure 3:
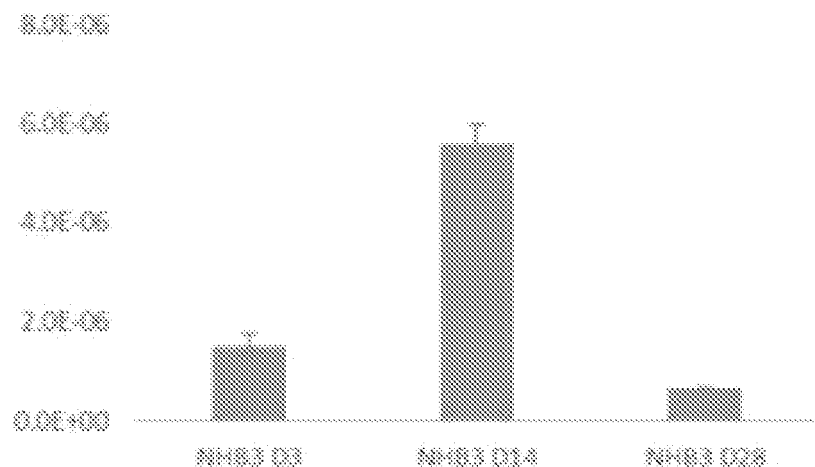

Human primary osteoblasts isolated from the subchondral bone of patients undergoing TKA for osteoarthritis of the knee (KOA) or THA for neck of femur fracture (NOF) were cultured under differentiating conditions for a period of 28d [35-40, 47]. Overall the NOF cultures mineralised to a significantly greater extent than KOA donors, as assayed by Alizarin Red staining, consistent with previous unpublished observations (FIG. 2). The reason for this could relate either to the site harvested (proximal femur for NOF and subchondral proximal tibia for KOA), or more likely, to the dysregulated mineralisation evident in differentiating osteoblasts form patients with osteoarthritis, as we have previously reported for cells isolated from the proximal femur [41]. All donors' cells displayed strong characteristics of pre-osteocytes/osteocytes by day 14, and in 2 cases by day 3, expressing appreciable mRNA for DMP1, SOST and OCN. In 2/3 cases, DMP1, SOST and OCN mRNA expression declined from the D14 level by D28, consistent with the acquisition of a mature osteocyte-like phenotype associated with loss of organelles and a decrease in the overall metabolic level [35, 48]. All donors' cultures also expressed mRNA coding for the osteoclastogenesis-related genes, RANKL and OPG (FIG. 3 to FIG. 7), also consistent with an osteocyte-like phenotype [35]. The expression of NGF mRNA was relatively abundant in these cultures from all donors' cells tested and mirrored that of the differentiation markers above, peaking at day 14 and declining by day 28 (KOA2 in FIG. 8). Furthermore, all donors' cells secreted appreciable full-length NGF protein detected in the supernatant: KOA 111.9±48.8 pg/ml; NOF 85.0±60.3 pg/ml.

In further work, all KOA donors' cells displayed strong characteristics of pre-osteocytes/osteocytes by day 3, expressing appreciable mRNA for DMP1, SOST and OCN (FIG. 25A-C). DMP1 and SOST mRNAs were expressed to a similar level overall based on delta-cycle threshold (ΔCT) values, while OCN mRNA was more abundantly expressed. The expression of DMP1 and OCN increased by D14 and then declined by D28, consistent with the acquisition of a mature osteocyte-like phenotype associated with loss of organelles and a decrease in the overall metabolic level [35, 48]. The expression of NGF mRNA was relatively abundant in these cultures, similar to that of OCN, from all donors' cells tested and mirrored that of the differentiation markers above, peaking at day 14 and declining by day 28 (FIG. 1D). Furthermore, all KOA donors' cells secreted appreciable full-length NGF protein detected in the supernatant (111.9±48.8 pg/ml).

Importantly, all three donors' cells expressed abundant mRNA encoding NGF (FIG. 8), consistent with human osteocytes being a source of NGF protein and being potentially able to contribute to the pain response in knee osteoarthritis. In order to test this further, osteocytes were digested from the bone of an additional donor according to our published protocol [46]. Immunostaining revealed strong positivity for cytoplasmic NGF protein (FIG. 9). It is though that this is the first report of osteocyte expression of NGF.

Effect of PPS Pre-Treatment on the Secretion of NGF

Human osteocyte-like cultures derived from KOA or NOF osteoblasts were either untreated (control) or pre-treated for 72 h with differing concentrations of PPS (1, 5 or 50 μg/mL). Supernatants were tested for mature NGF protein secretion by ELISA. All donors' cells tested expressed detectable secreted NOR Interestingly, the secreted levels increased in response to PPS treatments (FIG. 10 and FIG. 11)

Effect of PPS on TNF Induced NGF and proNGF Secretion

To examine further the effects of PPS on NGF expression, osteocyte-like cultures derived from three KOA and three NOF donor osteoblasts were treated after 3 days pre-treatment with differing concentrations of PPS, with rhTNFα in the absence or presence of the pre-treatment concentration of PPS. Supernatants were collected 48 h following treatment and subjected to ELISA analysis, as described in Materials and Methods. A study by Malerba and colleagues [29] demonstrated that the presence of the immature proprotein form of NGF, proNGF, together with mature NGF in an experimental sample, imparted false readings in many commercially-available ELISAs for NGF, and these effects were to an unpredictable magnitude and direction. Therefore, in this study proNGF levels were also measured in the treated supernatants, as described in Materials and Methods.

As was observed for mature protein, basal proNGF was detectable in all donor cell culture supernatants (FIG. 14 and FIG. 15 and FIG. 27). Recombinant human TNFα treatment, including for both KOA and NOF cell cultures, significantly increased the levels of proNGF, consistent with the induction of NGF expression in response to this pro-inflammatory stimulus in an osteoarthritic setting [27, 49]. PPS strongly suppressed basal proNGF secretion in all donors' cells assayed and at all of the PPS concentrations tested. Important from a therapeutic viewpoint, PPS also strongly reversed the effect of rhTNF on proNGF secretion (FIG. 14 and FIG. 15) in both KOA and NOF cultures and FIG. 27, again at all concentrations tested.

The concentrations of PPS chosen were based on those reported previously [43]. A study by Dawes et al in 1986 reported plasma concentrations of PPS of approximately 1-3 μg/ml in volunteers injected subcutaneously with PPS, supportive that the effective doses used here have clinical relevance. However, the lack of a dose response in our assays can be considered a study limitation. Strikingly similar findings were made for NOF cells (FIG. 29), suggesting that NGF expression and its regulation by PPS may be a common feature of osteocytes between skeletal sites and pathologies.

Effect of PPS on TNF Induced Gene Expression

Following three days of pre-treatment of osteocyte-like cultures with PPS and a further 48 h treatment period, total RNA was isolated for the purposes of analysing gene expression using real-time RT-PCR. While the quality of the RNA isolated from all cultures appeared to be high, as adjudged by Nanodrop micro-spectrophotometry showing the ratio of absorbance at 260 nm/280 nm generally being between 1.9 and 2.0, there was a consistent inability to generate complementary DNA (cDNA) from any samples exposed to 5 or 50 μg/mL PPS, except in one or two samples. This was evidence by all untreated and TNF-treated samples from all six donors yielding assayable housekeeping gene (18S, BACT) expression but strongly decreased or absent housekeeping gene expression in the general presence of PPS. This was despite increased attempts at removing potentially contaminating PPS by repetitive washing of the RNA pellet. We concluded that PPS contamination of the precipitated RNA, due likely to its five-carbon sugar-like structural similarity to RNA leading to co-precipitation, was inhibiting the reverse transcription of RNA into cDNA. Such inhibitory activity by PPS of various reverse transcriptases has previously been documented [30-32]. However, following repeated washing of RNA pellets prior to reverse transcription, as stated above, did produce cDNA from two of the three KOA donors' cultures from untreated, TNFα-treated, PPS (1 μg/mL) and TNFα+PPS (1 μg/mL) treated cultures, and these were analysed by real-time RT-PCR. Results are shown in FIG. 16 to FIG. 18.

Of most interest was the effect of PPS on NGF mRNA expression. Human osteocyte-like cultures expressed measurable NGF mRNA (FIG. 16). In the presence of TNFα, one donor's (KOA1) expression level was unchanged while in the second donor (KOA2) it was decreased. It should be noted that 48 h after TNFα exposure is a relatively late time point, as many genes would be expected to be stimulated within minutes or hours of exposure and commonly decrease thereafter; ideally a time course of the rhTNFα-treated cells would be of interest to examine. Importantly, PPS alone or in combination with rhTNFα, strongly suppressed NGF mRNA levels (FIG. 16).

To further examine whether the effects of PPS on NGF/proNGF expression were at the transcriptional level, additional work was undertaken in probing NGF mRNA expression using real-time RT-PCR (FIG. 28). Exposure to TNFα increased the relative expression of NGF mRNA levels. However, PPS at 1 mg/mL significantly reduced NGF expression in the presence of TNFα, suggesting This finding is consistent with the protein expression data and supports the hypothesis that PPS reverses the effects of proinflammatory mediators in KOA on the expression of mediators of pain. The expression by osteocytes of two of the known receptors for NGF was also examined by RT-PCR as well as immunohistochemistry. The expression of the high affinity receptor tropomyosin receptor kinase A (TrkA) was not detectable by RT-PCR in either KOA1 or KOA2 (FIG. 19), consistent with a complete lack of signal by immunostaining/confocal microscopy (FIG. 24). The lack of expression of TrkA by human osteocytes is consistent with the findings of Castaneda-Corral et al., who reported that only neurons expressed detectable levels of this protein in mouse bone [53]. Very low levels of the NGF receptor P75NTR mRNA were however detected, although there was sporadic detection across the samples tested; as for TRKA (FIG. 19), no detectable immunostaining for this molecule was observed (FIG. 24). These observations support the concept that NGF expression by osteocytes acts in a paracrine manner in the bone, with the most likely target cell being bone sensory neurons.

Interestingly, PPS also inhibited the effect of rhTNFα on IL-6 mRNA expression (FIG. 17); IL-6 transcription and secretion are key readouts of TNF-induced NFκB signalling [54]. Furthermore, rhTNFα induced COX2 mRNA expression (FIG. 18). COX2 is the enzyme responsible for prostaglandin E2 ($PGE_2$) expression, an important pro-inflammatory mediator involved in bone destruction, and is a target for several non-steroidal anti-inflammatory drugs (NSAIDs), with purported efficacy for the relief of OA-associated pain [55]. PPS alone and in combination with rhTNFα, completely inhibited COX2 mRNA expression.

These findings suggest that PPS inhibits multiple downstream pro-inflammatory effects of TNFα, and are consistent with a previous report that PPS acts as a transcriptional inhibitor of intracellular signalling pathways elicited by TNFα/TNF receptor signalling [32].

In terms of the mechanisms of the cartilage destruction associated with KOA, it was also of interest to examine the expression of MMP13, a key enzyme produced by osteocytes in the regulation of bone quality [56], and one associated with cartilage destruction in OA [57]. PPS has been implicated as an inhibitor of MMP13 expression in response to IL-1β, although this has not been unequivocally demonstrated [33]. In this study, rhTNFα induced MMP13 mRNA expression in KOA donor osteocyte-like cultures, an effect that was strongly inhibited by PPS treatment (FIG. 20). This was confirmed at the protein level by immunostaining (FIG. 21). This provides preliminary mechanistic data to support the concept that PPS is protective of cartilage breakdown in KOA, by virtue of its effects in sub-chondral bone osteocytes.

CONCLUSIONS

This study shows that PPS may be used in inhibiting or reducing NGF or pro-NGF activity. Further, the study shows for the first time the effects of PPS on human primary osteocytes isolated from the subchondral bone in patients with osteoarthritis of the knee. It also the first demonstration of the production and secretion of NGF/proNGF by this cell type, implicating osteocytes in the pain response in pathological conditions including, but not necessarily exclusively, KOA. PPS inhibited basal and TNFα-induced levels of proNGF secretion and TNF α-induced NGF mRNA expression. PPS also inhibited TNFα-induced levels of the collagenase MMP-13. Together, this provides evidence that PPS may act at multiple levels to suppress the release of NGF and potentially other pain mediators in the subchondral bone, to ameliorate pain associated with knee osteoarthritis.

Example Study 2: Effects of Combinations of rhTNF and PPS on NGF Gene Expression in Human Osteocyte-Like Cultures A follow up study to examine the possibility that PPS exerts an effect on NGF/proNGF expression at the transcriptional level is described.

Materials and Methods

The methodology for this study is the same as that for Example 1, with the addition of the below.

Isolation of Human Osteocytes

For some experiments, osteocytes were isolated directly from human bone samples, according to published protocol [46]. Briefly, bone obtained from TKA was rinsed vigorously in sterile PBS and then subjected to six serial digestions of collagenase/dispase/EDTA, with intervening recovery of released cells by centrifugation and washing in PBS. The cells obtained from digests 4-6, corresponding to an osteocyte-enriched fraction [46] were pooled, washed twice further by centrifugation and resuspension in PBS and then seeded into 8-well glass bottomed chamber slides. After allowing cells to recover for 72 h, they were either immunostained or pretreated with PPS and then treated with combinations of PPS and rhTNFα, as indicated.

Results and Discussion

NGF Expression by Freshly Isolated Human Osteocytes

NGF expression was also tested in cells directly digested from human KOA bone. As shown in FIG. 22, numerous cells in the 'osteocyte-enriched' fractions of sequential bone digests [46] stained brightly for NGF expression. This is the first report to our knowledge of NGF expression by human osteocytes. NGF expression was qualitatively upregulated in these cells by exposure to TNF-α, which was downregulated by coincubation with PPS.

Effect of PPS on TNFα-Induced NGF mRNA Expression

To examine whether the effects of PPS on NGF/proNGF expression were at the transcriptional level, we also examined NGF mRNA expression using real-time RT-PCR (FIG. 23). Exposure to TNFα increased the relative expression of NGF mRNA. PPS at both 0.1 and 1 µg/mL had no apparent effect on basal NGF mRNA levels. However, PPS at 1 µg/mL significantly reduced NGF expression in the presence of TNFα, suggesting that at least some of the effect of PPS on osteocytes is at the transcriptional level. This is consistent with a previous report that PPS acts as a transcriptional inhibitor of intracellular signalling pathways elicited by TNFα/TNF receptor signalling [32]. It supports the hypothesis that PPS reverses the effects of proinflammatory mediators in KOA on the expression of mediators of pain.

Conclusions for Example 2

This study shows the effects of PPS on the responses of human primary osteocyte-like cultures, differentiated from the proximal tibiae of patients suffering from advanced KOA and undergoing TKA. Treatment with recombinant TNFα was used as the proinflammatory stimulus, and the effects on the relative expression of NGF mRNA was examined. ProNGF protein levels were also determined.

We show once again that human osteocytes are capable of producing NGF, suggesting that they potentially contribute to localised pain responses. We also show that PPS suppresses NGF mRNA transcription and proNGF secretion by osteocytes and reverses the stimulatory effects of TNFα on these processes. Together, our findings suggest a hitherto unknown role for osteocytes in the pain response and a mechanism for the pain benefit in KOA patients taking PPS.

Example Study 3: NGF Expression by Freshly Isolated Human Osteocytes and in Human Bone This study follows on from Example Study 2 and presents further work in characterising NGF expression.
Materials and Methods The methodology for this study is the same as that for Example 2.
Results and Discussion To examine NGF protein expression, we optimised staining of a directly conjugated anti-NGF antibody to NCI-H266 cells (FIG. 26, top row). NGF expression was also tested in cells obtained by sequential digestion from human KOA bone. It has been published previously that fractions IV-VI obtained using this method are enriched for mature osteocytes [46]. As shown in FIG. 26 (middle row), numerous cells in the osteocyte-enriched fractions stained brightly for NGF expression and co-stained for the osteocyte marker SOST/sclerostin. Furthermore, osteocyte expression of NGF was evident in stained sections of human KOA subchondral bone (FIG. 26 bottom row). Together with the observations in differentiated cultures above, this is the first report to our knowledge of NGF expression by human osteocytes. A previous study using a fluorescence reporter system to identify NGF expression in mouse bone, reported osteoblast but not osteocyte expression of NGF in response to mechanical loading of the ulna [23]. It is possible that the reporter system used lacked the sensitivity to detect low levels of NGF, or that the difference observed is due to interspecies, relative age, skeletal site, stimulus (mechanical rather than pro-inflammatory), as well as the influence of osteoarthritis on osteocyte expression.

As mentioned above in Example Study 2, in an attempt to examine regulation of NGF protein expression in freshly isolated KOA osteocyte-like cells, they were treated with either rhTNF-α, PPS or a combination of these. NGF immunostaining was detected in all cases although cells exposed to rhTNF-α alone and PPS alone had qualitatively greater NGF expression than control, and cells treated with a combination of rhTNF-α and PPS showed qualitatively less staining (FIG. 22).

Due to the unpredictable yields of osteocytes from individual patients' bone, it is technically difficult to achieve identical and sufficient numbers of resulting adherent viable cells between wells for quantitative assessment of treatments. Furthermore, since NGF is a secreted protein, it is difficult to interpret intracellular levels. Therefore the quantitative regulation of NGF secretion into the supernatants of differentiated cultures of osteocyte-like cells was studied.

In conclusion, it is demonstrated herein that PPS may be used in inhibiting or reducing NGF or pro-NGF activity. Further, the effects of PPS on human primary osteocytes isolated from the subchondral bone in patients with osteoarthritis of the knee are demonstrated for the first time herein. Disclosed herein is also the first demonstration of the production and secretion of NGF/proNGF by this cell type, implicating osteocytes in the pain response in pathological conditions including, but not necessarily exclusively, KOA. PPS inhibited basal and TNFα-induced levels of proNGF secretion and TNF α-induced NGF mRNA expression. PPS also inhibited TNFα-induced levels of the collagenase MMP-13. Together, this provides evidence that PPS may act at multiple levels to suppress the release of NGF and potentially other pain mediators in the subchondral bone, to ameliorate pain associated with knee osteoarthritis.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

REFERENCES

1. Chang D S, Hsu E, Hottinger D G, Cohen S P. Anti-nerve growth factor in pain management: current evidence. *J. Pain Res.* 2016 Jun. 8; 9:373-83.

1A. Giovengo S L, Russell I J, Larson A A. Increased concentrations of nerve growth factor in cerebrospinal fluid of patients with fibromyalgia. *J Rheumatol.* 1999 July; 26(7):1564-9.

1B. Giudice L C. Clinical practice. Endometriosis. *N Engl J Med.* 2010 Jun. 24; 362(25):2389-98. doi: 10.1056/NEJMcp1000274.

1C. Monteleone F, Nicoletti C G, Stampanoni Bassi M, Iezzi E, Buttari F, Furlan R, Finardi A, Marfia G A, Centonze D, Mori F. Nerve growth factor is elevated in the CSF of patients with multiple sclerosis and central neuropathic pain. *J Neuroimmunol.* 2018 Jan. 15; 314:89-93. doi: 10.1016/j.jneuroim.2017.11.012. Epub 2017 Nov. 20.

2. Miller R E, Malfait A-M, Block, J A. Current Status of Nerve Growth Factor Antibodies for the Treatment of Osteoarthritis Pain. *Clin. Exp Rheumatol.* 2017; 35 (Suppl 107): 85-87.

3. Batemen D, Kennedy J. Non-steroidal anti-inflammatory drugs and elderly patients. British Medical Journal. 1995; 310:817-8.

4. Brandt K D. Should nonsteroidal anti-inflammatory drugs be used to treat osteoarthritis? Rheumatic diseases clinics of North America. 1993; 19(1):29-44.

5. O'Mahony D. Prevention of corticosteroid-induced osteoporosis and fractures. Journal of Clinical Pharmacy and Therapeutics. 1999; 24(2):83-5.

6. Miyata N, Kumagai K, Osaki M, Murata M, Tomita M, Hozumi A, et al. Pentosan reduces osteonecrosis of femoral head in SHRSP. Clinical and experimental hypertension (New York, N Y: 1993). 2010; 32(8):511-6.

7. McCaffrey G, Thompson M L, Majuta L, Fealk M N, Chartier S, Longo G, Mantyh, P W. NGF blockade at early times during bone cancer development attenuates bone destruction and increases limb use. *Cancer Res.* 2014; Dec. 1; 74(23): 7014-7023.

8. Scully M F, Weerasinghe K M, Ellis V, Djazaeri B, Kakkar V V. Anticoagulant and antiheparin activities of a pentosan polysulphate. Thrombosis Research 1983; 31(1):87-97.

9. Krupinski K, Breddin H K, Casu B. Anticoagulant and antithrombotic effects of chemically modified heparins and pentosan polysulfate. Haemostasis 1990; 20(2):81-92.

10. Shanmugam M, Mody K H. Heparinoid-active sulphated polysaccharides from marine algae as potential blood anticoagulant agents. Current Science 2000; 79(12):1672-1683.

11. Vongchan P, Sajomsang W, Kasinrerk W, Subyen D, Kongrawelert P. Anticoagulant activities of the chitosan polysulfate synthesized from marine crab shell by semi-heterogeneous conditions. Science Asia 2003; 29:115-120.

12. Vinazzer H. Prevention of recurrence of cerebrovascular thromboses. A randomized comparative study acetylsalicylic acid and sodium pentosan polysulfate. Fortschr Med 1987; 105(5):79-85.
13. Losonczy H, David M, Nagy I. Effect of pentosan polysulfate on activated partial thromboplastin time, thrombin time, euglobulin clot lysis and tissue-type plasminogen activator and plasminogen activator inhibitor activities in patients with thromboembolic disease. Semin Thromb Hemost 1991; 17(4):394-8.
14. WO 2008/144836. Sulphated xylans for treatment or prophylaxis of respiratory diseases.
15. WO 2002/41901. Treatment of osteoporosis.
16. WO 2012/103588. Treatment of bone marrow (oedema) with polysulfated polysaccharides.
17. Hjermstad M J, Fayers P M, Haugen D F, Caraceni A, Hanks G W, Loge J H, et al. Studies comparing Numerical Rating Scales, Verbal Rating Scales, and Visual Analogue Scales for assessment of pain intensity in adults: a systematic literature review. Journal of pain and symptom management. 2011; 41(6):1073-93.
18. Briggs K K, Kocher M S, Rodkey W G, Steadman J R. Reliability, validity, and responsiveness of the Lysholm knee score and Tegner activity scale for patients with meniscal injury of the knee. The Journal of bone and joint surgery American volume. 2006; 88(4):698-705.
19. Roos E M, Lohmander L S. Knee injury and Osteoarthritis Outcome Score (KOOS): from joint injury to osteoarthritis. Health Qual Life Outcomes 2003; 1:64.
20. Fairbank J C T and Pynsent P B (2000) The Owestery Disability Index. Spine, 25(22):2940-2953.
21. Chevalier X, Eymard F, Richette P. Biologic agents in osteoarthritis: hopes and disappointments. Nat Rev Rheumatol 2013; 9: 400-10.
22. Ayers D C, Li W, Harrold L, Allison J, Franklin P D. Preoperative pain and function profiles reflect consistent TKA patient selection among U S surgeons. Clin Orthop Relat Res 2015; 473: 76-81.
23. Tomlinson R E, Li Z, Li Z, Minichiello L, Riddle R C, Venkatesan A, Clemens T L. NGF-TrkA signaling in sensory nerves is required for skeletal adaptation to mechanical loads in mice. Proc Natl Acad Sci USA 2017; 114: E3632-E3641.
24. Lane N E, Schnitzer T J, Birbara C A, Mokhtarani M, Shelton D L, Smith M D, Brown M T. Tanezumab for the treatment of pain from osteoarthritis of the knee. N Engl J Med 2010; 363: 1521-31.
25. Schnitzer T J, Ekman E F, Spierings E L, Greenberg H S, Smith M D, Brown M T, West C R, Verburg K M. Efficacy and safety of tanezumab monotherapy or combined with non-steroidal anti-inflammatory drugs in the treatment of knee or hip osteoarthritis pain. Ann Rheum Dis 2015; 74: 1202-11.
26. Ekman E F, Gimbel J S, Bello A E, Smith M D, Keller D S, Annis K M, Brown M T, West C R, Verburg K M. Efficacy and safety of intravenous tanezumab for the symptomatic treatment of osteoarthritis: 2 randomized controlled trials versus naproxen. J Rheumatol 2014; 41: 2249-59.
27. Takano S, Uchida K, Miyagi M, Inoue G, Fujimaki H, Aikawa J, Iwase D, Minatani A, Iwabuchi K, Takaso M. Nerve Growth Factor Regulation by TNF-alpha and IL-1beta in Synovial Macrophages and Fibroblasts in Osteoarthritic Mice. J Immunol Res 2016; 2016: 5706359.
28. Bradshaw R A, Pundavela J, Biarc J, Chalkley R J, Burlingame A L, Hondermarck H. NGF and ProNGF: Regulation of neuronal and neoplastic responses through receptor signaling. Adv Biol Regul 2015; 58: 16-27.
29. Malerba F, Paoletti F, Cattaneo A. NGF and proNGF Reciprocal Interference in Immunoassays: Open Questions, Criticalities, and Ways Forward. Front Mol Neurosci 2016; 9: 63.
30. Giusto L L, Zahner P M, Shoskes D A. An evaluation of the pharmacotherapy for interstitial cystitis. Expert Opin Pharmacother 2018; 19: 1097-1108.
31. Sampson M J, Kabbani M, Krishnan R, Nganga M, Theodoulou A, Krishnan J. Improved clinical outcome measures of knee pain and function with concurrent resolution of subchondral Bone Marrow Edema Lesion and joint effusion in an osteoarthritic patient following Pentosan Polysulphate Sodium treatment: a case report. BMC Musculoskelet Disord 2017; 18: 396.
32. Sunaga T, Oh N, Hosoya K, Takagi S, Okumura M. Inhibitory effects of pentosan polysulfate sodium on MAP-kinase pathway and N F-kappaB nuclear translocation in canine chondrocytes in vitro. J Vet Med Sci 2012; 74: 707-11.
33. Bwalya E C, Kim S, Fang J, Wijekoon H M S, Hosoya K, Okumura M. Pentosan polysulfate inhibits IL-1beta-induced iNOS, c-Jun and HIF-1alpha upregulation in canine articular chondrocytes. PLoS One 2017; 12: e0177144.
34. Atkins G J, Findlay D M. Osteocyte regulation of bone mineral: a little give and take. Osteoporos Int 2012; 23: 2067-79.
35. Prideaux M, Findlay D M, Atkins G J. Osteocytes: The master cells in bone remodelling. Curr Opin Pharmacol 2016; 28: 24-30.
36. Ormsby R T, Cantley M, Kogawa M, Solomon L B, Haynes D R, Findlay D M, Atkins G J. Evidence that osteocyte perilacunar remodelling contributes to polyethylene wear particle induced osteolysis. Acta Biomater 2016; 33: 242-51.
37. Yang D, Wijenayaka A R, Solomon L B, Pederson S M, Findlay D M, Kidd S P, Atkins G J. Novel Insights into Staphylococcus aureus Deep Bone Infections: the Involvement of Osteocytes. MBio 2018; 9.
38. Atkins G J, Rowe P S, Lim H P, Welldon K J, Ormsby R, Wijenayaka A R, Zelenchuk L, Evdokiou A, Findlay D M. Sclerostin is a locally acting regulator of late-osteoblast/preosteocyte differentiation and regulates mineralization through a MEPE-ASARM-dependent mechanism. J Bone Miner Res 2011; 26: 1425-36.
39. Atkins G J, Welldon K J, Wijenayaka A R, Bonewald L F, Findlay D M. Vitamin K promotes mineralization, osteoblast-to-osteocyte transition, and an anticatabolic phenotype by {gamma}-carboxylation-dependent and -independent mechanisms. Am J Physiol Cell Physiol 2009; 297: C1358-67.
40. Kogawa M, Wijenayaka A R, Ormsby R T, Thomas G P, Anderson P H, Bonewald L F, Findlay D M, Atkins G J. Sclerostin Regulates Release of Bone Mineral by Osteocytes by Induction of Carbonic Anhydrase 2. J Bone Miner Res 2013; 28: 2436-2448.
41. Kumarasinghe D D, Sullivan T, Kuliwaba J S, Fazzalari N L, Atkins G J. Evidence for the dysregulated expression of TWIST1, TFIβ1 and SMAD3 in differentiating osteoblasts from primary hip osteoarthritis patients. Osteoarthritis & Cartilage 2012; 20: 1357-1366.
42. Wijenayaka A R, Kogawa M, Lim H P, Bonewald L F, Findlay D M, Atkins G J. Sclerostin Stimulates Osteocyte Support of Osteoclast Activity by a RANKL-Dependent Pathway. PLoS One 2011; 6: e25900.

43. Ghosh P, Wu J, Shimmon S, Zannettino A C, Gronthos S, Itescu S. Pentosan polysulfate promotes proliferation and chondrogenic differentiation of adult human bone marrow-derived mesenchymal precursor cells. Arthritis Res Ther 2010; 12: R28.
44. Iannone F, De Bari C, Dell'Accio F, Covelli M, Patella V, Lo Bianco G, Lapadula G. Increased expression of nerve growth factor (NGF) and high affinity NGF receptor (p140 TrkA) in human osteoarthritic chondrocytes. Rheumatology (Oxford) 2002; 41: 1413-8.
45. Zhang J, Wang L S, Ye S L, Luo P, Wang B L. Blockage of tropomyosin receptor kinase a (TrkA) enhances chemo-sensitivity in breast cancer cells and inhibits metastasis in vivo. Int J Clin Exp Med 2015; 8: 634-41.
46. Prideaux M, Schutz C, Wijenayaka A R, Findlay D M, Campbell D G, Solomon L B, Atkins G J. Isolation of osteocytes from human trabecular bone. Bone 2016; 88: 64-72.
47. Atkins G J, Welldon K J, Halbout P, Findlay D M. Strontium ranelate treatment of human primary osteoblasts promotes an osteocyte-like phenotype while eliciting an osteoprotegerin response. Osteoporos Int 2009; 20: 653-64.
48. Bonewald L F. The amazing osteocyte. J Bone Miner Res 2011; 26: 229-38.
49. Manni L, Aloe L. Role of IL-1 beta and TNF-alpha in the regulation of NGF in experimentally induced arthritis in mice. Rheumatol Int 1998; 18: 97-102.
50. Anand R, Nayyar S, Galvin T A, Merril C R, Bigelow L B. Sodium pentosan polysulfate (PPS), an anti-HIV agent also exhibits synergism with AZT, lymphoproliferative activity, and virus enhancement. AIDS Res Hum Retroviruses 1990; 6: 679-89.
51. Baba M, Nakajima M, Schols D, Pauwels R, Balzarini J, De Clercq E. Pentosan polysulfate, a sulfated oligosaccharide, is a potent and selective anti-HIV agent in vitro. Antiviral Res 1988; 9: 335-43.
52. Sydow G, Klocking H P. Effect of pentosan polysulfate (SP 54) on the reverse transcriptase activity of several retroviruses. Biomed Biochim Acta 1987; 46: 527-30.
53. Castaneda-Corral G, Jimenez-Andrade J M, Bloom A P, Taylor R N, Mantyh W G, Kaczmarska M J, Ghilardi J R, Mantyh P W. The majority of myelinated and unmyelinated sensory nerve fibers that innervate bone express the tropomyosin receptor kinase A. Neuroscience 2011; 178: 196-207.
54. Vanden Berghe W, Vermeulen L, De Wilde G, De Bosscher K, Boone E, Haegeman G. Signal transduction by tumor necrosis factor and gene regulation of the inflammatory cytokine interleukin-6. Biochem Pharmacol 2000; 60: 1185-95.
55. van Walsem A, Pandhi S, Nixon R M, Guyot P, Karabis A, Moore R A. Relative benefit-risk comparing diclofenac to other traditional non-steroidal anti-inflammatory drugs and cyclooxygenase-2 inhibitors in patients with osteoarthritis or rheumatoid arthritis: a network meta-analysis. Arthritis Res Ther 2015; 17: 66.
56. Tang S Y, Herber R P, Ho S P, Alliston T. Matrix metalloproteinase-13 is required for osteocytic perilacunar remodeling and maintains bone fracture resistance. J Bone Miner Res 2012; 27: 1936-50.
57. Li H, Wang D, Yuan Y, Min J. New insights on the MMP-13 regulatory network in the pathogenesis of early osteoarthritis. Arthritis Res Ther 2017; 19: 248.
Rouillard A D, Gundersen G W, Fernandez N F, Wang Z, Monteiro C D, McDermott M G, Ma'ayan A. The harmonizome: a collection of processed datasets gathered to serve and mine knowledge about genes and proteins. LID—10.1093/database/baw100 [doi] LID—baw100 [pii] (1758-0463 (Electronic)).
Dawes J, Prowse C V, Pepper D S. Absorption of heparin, LMW heparin and SP54 after subcutaneous injection, assessed by competitive binding assay. Thrombosis Research. 1986; 44 (0049-3848 (Print)): 683-93.

The invention claimed is:

1. A method of treating malignant bone pain not associated with bone marrow edema in a mammal by inhibiting or reducing Nerve Growth Factor (NGF) or pro-Nerve Growth Factor (pro-NGF) activity in the mammal, the method comprising the step of administering an effective amount of a salt of pentosan polysulfate formulated as a composition for administration by intra-muscular (IM) or sub-cutaneous (SC) routes, an intraventricular route, intracisternal route or intrathecal route, intra-venously (IV), intra-articularly (IA), peri-articularly, topically or via suppositories to the mammal so as to treat pain in the mammal.

2. The method or use according to claim 1, wherein the malignant bone pain is pain associated with primary bone cancer or pain associated with secondary (metastatic) bone cancer.

3. The method according to claim 1, wherein the pentosan polysulfate (PPS) salt is selected from the group consisting of: the sodium salt of pentosan polysulfate (NaPPS), the magnesium salt of pentosan polysulfate (MgPPS), the calcium salt of pentosan polysulfate (CaPPS), and the zinc salt of pentosan polysulfate (ZnPPS).

4. The method according to claim 3, wherein the pentosan polysulfate (PPS) salt is sodium pentosan polysulfate (NaPPS).

5. The method according to claim 4, wherein the NaPPS is administered to the mammal is in an effective amount of about 1 mg/kg to about 2 mg/kg of the mammal per dose.

6. The method according to claim 5, wherein administration to the mammal is by dosing in a treatment regimen once daily, twice weekly or thrice weekly.

7. The method according to claim 6, wherein the total dose of polysulfated polysaccharide administered in the treatment regimen is about 200 to 4000 mg.

* * * * *

SEQUENCE LISTING

<160> NUMBER OF SEQ ID NOS: 26

<210> SEQ ID NO 1
<211> LENGTH: 20
<212> TYPE: DNA
<213> ORGANISM: Homo sapiens

<400> SEQUENCE: 1
ggaattcccg agtaagtgcg                                                    20

<210> SEQ ID NO 2
<211> LENGTH: 19
<212> TYPE: DNA
<213> ORGANISM: Homo sapiens

<400> SEQUENCE: 2
gcctcactaa accatccaa                                                     19

<210> SEQ ID NO 3
<211> LENGTH: 21
<212> TYPE: DNA
<213> ORGANISM: Homo sapiens

<400> SEQUENCE: 3
cgcgagaaga tgacccagat c                                                  21

```
<210> SEQ ID NO 4
<211> LENGTH: 18
<212> TYPE: DNA
<213> ORGANISM: Homo sapiens

<400> SEQUENCE: 4
tcaccggagt ccatcacg                                          18

<210> SEQ ID NO 5
<211> LENGTH: 21
<212> TYPE: DNA
<213> ORGANISM: Homo sapiens

<400> SEQUENCE: 5
ggagaaaact gctcaacacc g                                      21

<210> SEQ ID NO 6
<211> LENGTH: 23
<212> TYPE: DNA
<213> ORGANISM: Homo sapiens

<400> SEQUENCE: 6
tattcacaac gttccaaaat ccc                                    23

<210> SEQ ID NO 7
<211> LENGTH: 21
<212> TYPE: DNA
<213> ORGANISM: Homo sapiens

<400> SEQUENCE: 7
gatcagcatc ctgctcatgt t                                      21

<210> SEQ ID NO 8
<211> LENGTH: 21
<212> TYPE: DNA
<213> ORGANISM: Homo sapiens

<400> SEQUENCE: 8
agccaaatga cccttccatt c                                      21

<210> SEQ ID NO 9
<211> LENGTH: 20
<212> TYPE: DNA
<213> ORGANISM: Homo sapiens

<400> SEQUENCE: 9
tcagccctga gaaaggagac                                        20

<210> SEQ ID NO 10
<211> LENGTH: 22
<212> TYPE: DNA
<213> ORGANISM: Homo sapiens

<400> SEQUENCE: 10
tctcctcatt gaatccagat tg                                     22

<210> SEQ ID NO 11
<211> LENGTH: 20
<212> TYPE: DNA
<213> ORGANISM: Homo sapiens

<400> SEQUENCE: 11
ggatccagtc tctctatggt                                        20
```

<210> SEQ ID NO 12
<211> LENGTH: 20
<212> TYPE: DNA
<213> ORGANISM: Homo sapiens

<400> SEQUENCE: 12
ggcatcaagg gataaggaag                                               20

<210> SEQ ID NO 13
<211> LENGTH: 20
<212> TYPE: DNA
<213> ORGANISM: Homo sapiens

<400> SEQUENCE: 13
cacactgagg tgcatagcgt                                               20

<210> SEQ ID NO 14
<211> LENGTH: 20
<212> TYPE: DNA
<213> ORGANISM: Homo sapiens

<400> SEQUENCE: 14
tgatgaccgc ttgctcctgt                                               20

<210> SEQ ID NO 15
<211> LENGTH: 19
<212> TYPE: DNA
<213> ORGANISM: Homo sapiens

<400> SEQUENCE: 15
cctggacagc gtgacgttc                                                19

<210> SEQ ID NO 16
<211> LENGTH: 20
<212> TYPE: DNA
<213> ORGANISM: Homo sapiens

<400> SEQUENCE: 16
cccagtcgtc tcatcctggt                                               20

<210> SEQ ID NO 17
<211> LENGTH: 19
<212> TYPE: DNA
<213> ORGANISM: Homo sapiens

<400> SEQUENCE: 17
cctggacagc gtgacgttc                                                19

<210> SEQ ID NO 18
<211> LENGTH: 20
<212> TYPE: DNA
<213> ORGANISM: Homo sapiens

<400> SEQUENCE: 18
cccagtcgtc tcatcctggt                                               20

<210> SEQ ID NO 19
<211> LENGTH: 22
<212> TYPE: DNA
<213> ORGANISM: Homo sapiens

<400> SEQUENCE: 19

```
atgagagccc tcacactcct cg                                              22

<210> SEQ ID NO 20
<211> LENGTH: 22
<212> TYPE: DNA
<213> ORGANISM: Homo sapiens

<400> SEQUENCE: 20
gtcagccaac tcgtcacagt cc                                              22

<210> SEQ ID NO 21
<211> LENGTH: 23
<212> TYPE: DNA
<213> ORGANISM: Homo sapiens

<400> SEQUENCE: 21
gctcacaaga acagactttc cag                                             23

<210> SEQ ID NO 22
<211> LENGTH: 25
<212> TYPE: DNA
<213> ORGANISM: Homo sapiens

<400> SEQUENCE: 22
ctgttttcac agaggtcaat atctt                                           25

<210> SEQ ID NO 23
<211> LENGTH: 20
<212> TYPE: DNA
<213> ORGANISM: Homo sapiens

<400> SEQUENCE: 23
ccaagatctc caacatgact                                                 20

<210> SEQ ID NO 24
<211> LENGTH: 22
<212> TYPE: DNA
<213> ORGANISM: Homo sapiens

<400> SEQUENCE: 24
tacaccatta gttgaagata ct                                              22

<210> SEQ ID NO 25
<211> LENGTH: 20
<212> TYPE: DNA
<213> ORGANISM: Homo sapiens

<400> SEQUENCE: 25
accggagctg gagaacaaca                                                 20

<210> SEQ ID NO 26
<211> LENGTH: 20
<212> TYPE: DNA
<213> ORGANISM: Homo sapiens

<400> SEQUENCE: 26
gctgtactcg gacacgtctt                                                 20
```